(12) United States Patent
Brunicardi et al.

(10) Patent No.: US 10,813,909 B2
(45) Date of Patent: Oct. 27, 2020

(54) TRIPLE DRUG COMBINATION (METFORMIN, SIMVASTATIN, DIGOXIN) FOR TARGETED TREATMENT OF PANCREATIC CANCER

(71) Applicant: THE REGENTS OF THE UNIVERSITY OF CALIFORNIA, Oakland, CA (US)

(72) Inventors: Francis C. Brunicardi, Pacific Palisades, CA (US); Robbi L. Sanchez, Pacific Palisades, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/302,587

(22) PCT Filed: May 19, 2017

(86) PCT No.: PCT/US2017/335120
§ 371 (c)(1),
(2) Date: Nov. 16, 2018

(87) PCT Pub. No.: WO2018/044369
PCT Pub. Date: Mar. 8, 2018

(65) Prior Publication Data
US 2019/0358193 A1    Nov. 28, 2019

Related U.S. Application Data

(60) Provisional application No. 62/338,655, filed on May 19, 2016.

(51) Int. Cl.
  A61K 31/155    (2006.01)
  A61K 31/337    (2006.01)
  A61K 31/7048   (2006.01)
  A61K 31/351    (2006.01)
  A61K 31/7068   (2006.01)

(52) U.S. Cl.
  CPC .......... A61K 31/351 (2013.01); A61K 31/155 (2013.01); A61K 31/337 (2013.01); A61K 31/7048 (2013.01); A61K 31/7068 (2013.01)

(58) Field of Classification Search
  None
  See application file for complete search history.

(56) References Cited

U.S. PATENT DOCUMENTS

2007/0281940 A1* 12/2007 Dugi .................. A61K 31/4184
                                                    514/248
2011/0034378 A1    2/2011 Dutt et al.
2011/0053862 A1    3/2011 Xie et al.
2012/0220664 A1    8/2012 Struhl et al.
2013/0115188 A1    5/2013 Fritsche et al.
2016/0030352 A1    2/2016 Lim et al.

FOREIGN PATENT DOCUMENTS

WO    2013/188452        12/2013
WO    2015/170248        11/2015
WO    WO-2015170248 A1 *  11/2015  ........... A61K 31/472

OTHER PUBLICATIONS

Holmes, Breast Cancer Research 2012, 14:216. (Year: 2012).*
PCT International Publication No. WO2018/044369 dated Mar. 8, 2018 with International Search Report, PCT/US2017/033512.
PCT Notification of Transmittal of International Search Report and Written Opinion dated Feb. 23, 2018, PCT/US2017/033512.
PCT Notification of Transmittal of International Search Report and Written Opinion dated Mar. 5, 2018, PCT/US2017/033512.
Gou, et al., "Low Concentrations of Metformin Selectively Inhibit CD133+ Cell Proliferation in Pancreatic Cancer and Have Anticancer Action," PLoS One, May 8, 2013, vol. 8, issue 5, e63969, pp. 1-9.
Hwang et al., "Apoptotic induction by simvastatin in human lung cancer A549 cells via Akt signaling dependent down-regulation of survivin," Investigational New Drugs, May 10, 2010, vol. 28, issue 5, pp. 945-952.
Zhang W.Z., "A Study on Effects of Digoxin on Proliferation and Apoptosis in Human Malignant Lymphoma Cell Lines and Its Mechanism," Dissertation, Hebei Medical University, Jan. 2011, pp. 1-51.
Zhang et al., "Inhibitory effects of metformin at low concentration on epithelial-mesenchymal transition of CD44+ CD117+ ovarian cancer stem cells," Stem Cell Research & Therapy, Dec. 30, 2015, vol. 6, pp. 1-12.
Ebner et al: "The Use of Transporter Probe Drug Cocktails for the Assessment of Transporter-Based Drug-Drug nteractions in a Clinical Setting-Proposal of a Four Component Transporter Cocktail", Journal of Jharmaceutical Sciences, vol. 104, No. 9, Sep. 1, 2015 (Sep. 1, 2015), pp. 3220-3228.
Supplementary European Search Report dated Oct. 30, 2019 for EP Application No. 17847118.1.

* cited by examiner

Primary Examiner — Layla D Berry
(74) Attorney, Agent, or Firm — Gates & Cooper LLP

(57) ABSTRACT

A combination of three well-known and FDA approved compounds has been discovered to significantly suppress the proliferation of pancreatic cancer cells in clinically relevant models of pancreatic cancer. Embodiments of the invention include compositions of matter comprising a combination of agents such as metformin, simvastatin, and digoxin as well as methods of treating cancers using such agents. Illustrative methods include combining a population of pancreatic cancer cells with amounts of metformin, simvastatin, and digoxin sufficient to inhibit expression of BIRC5 protein in the population of pancreatic cancer cells, thereby inhibiting the growth of the population of pancreatic cancer cells.

10 Claims, 49 Drawing Sheets
Specification includes a Sequence Listing.

Published Data demonstrate that BIRC5 (survivin) inhibits apoptosis via inhibition of Caspase 9 and Effector caspases. SMAC (Diablo) inhibits BIRC5 (survivin)

FIG. 47A
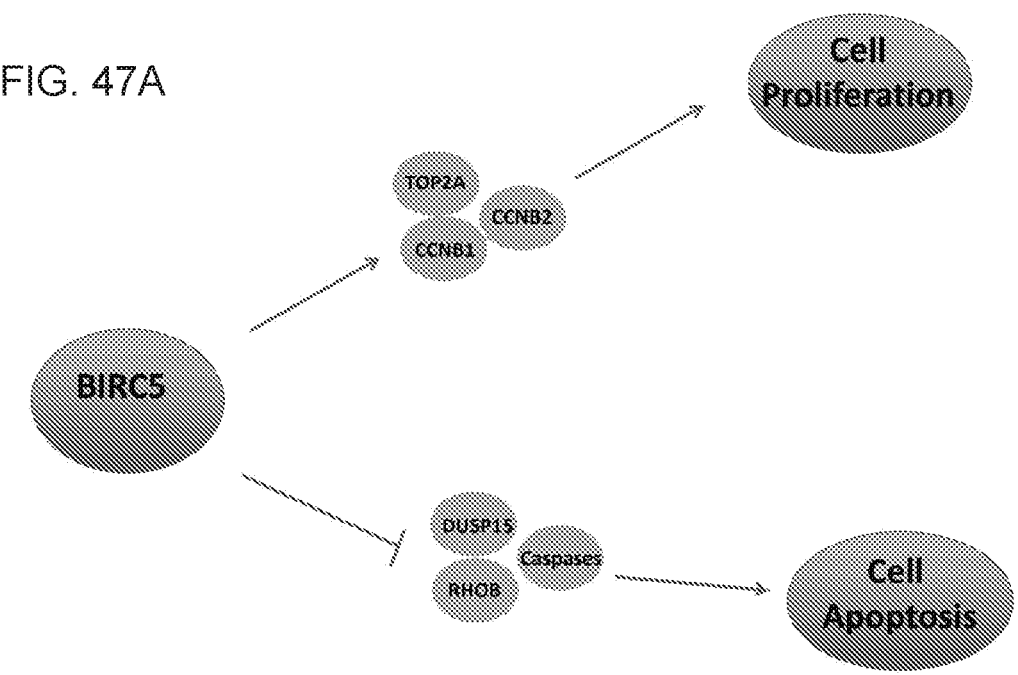
FIG. 47B
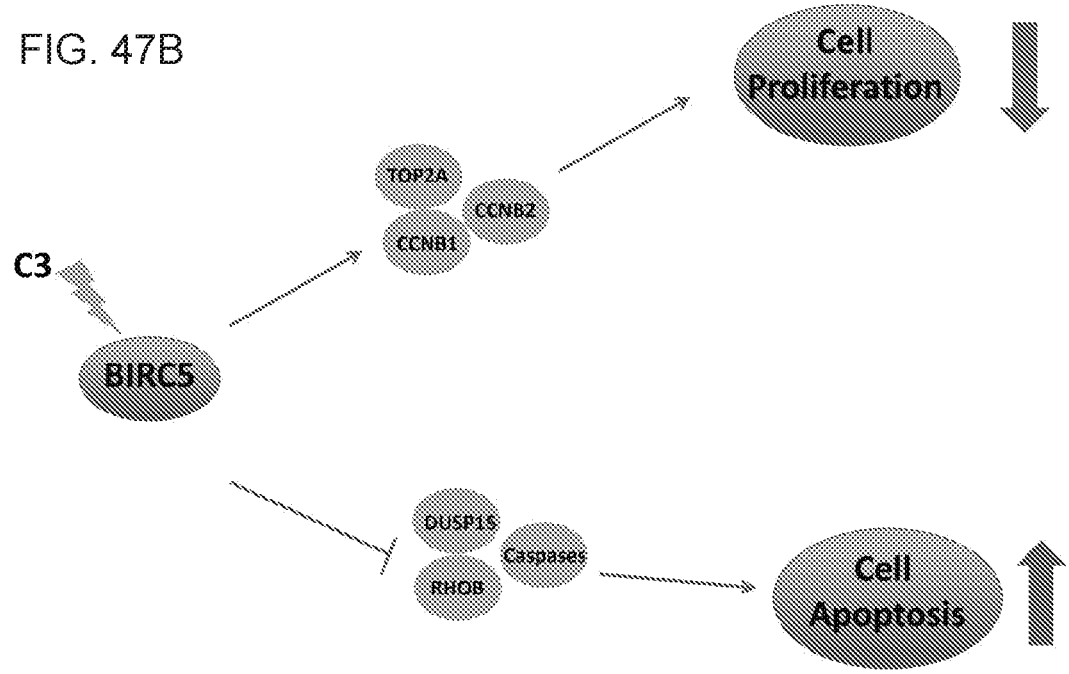
FIG. 47

SEQUENCE LISTING

<160> NUMBER OF SEQ ID NOS: 2

<210> SEQ ID NO 1
<211> LENGTH: 142
<212> TYPE: PRT
<213> ORGANISM: Homo sapiens

<400> SEQUENCE: 1

```
Met Gly Ala Pro Thr Leu Pro Pro Ala Trp Gln Pro Phe Leu Lys Asp
1               5                   10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140
```

<210> SEQ ID NO 2
<211> LENGTH: 2655
<212> TYPE: DNA
<213> ORGANISM: Homo sapiens

<400> SEQUENCE: 2

```
cccagaaggc cgcgggggggt ggaccgccta agagggcgtg cgctcccgac atgccccgcg      60
```

```
gcgcgccatt aaccgccaga tttgaatcgc gggacccgtt ggcagaggtg gcggcggcgg      120
catgggtgcc ccgacgttgc ccctgcctg gcagcccttt ctcaaggacc accgcatctc       180
tacattcaag aactggccct tcttggaggg ctgcgcctgc accccggagc ggatggccga      240
ggctggcttc atccactgcc ccactgagaa cgagccagac ttggcccagt gtttcttctg      300
cttcaaggag ctggaaggct gggagccaga tgacgacccc atagaggaac ataaaaagca     360
ttcgtccggt tgcgctttcc tttctgtcaa gaagcagttt gaagaattaa cccttggtga     420 attttttgaaa ctggacagag aaagagccaa gaacaaaatt gcaaggaaa ccaacaataa    480 gaagaaagaa tttgaggaaa ctgcggagaa agtgcgccgt gccatcgagc agctggctgc     540
catggattga ggcctctggc cggagctgcc tggtcccaga gtggctgcac cacttccagg      600
gtttattccc tggtgccacc agccttcctg tgggccccctt agcaatgtct taggaaagga    660
gatcaacatt ttcaaattag atgtttcaac tgtgctcttg ttttgtcttg aaagtggcac     720
cagaggtgct tctgcctgtg cagcgggtgc tgctggtaac agtggctgct ctctctctc      780 tctctcttt ttgggggctc attttttgctg ttttgattcc cgggcttacc aggtgagaag    840
tgagggagga agaaggcagt gtccctttg ctagagctga cagctttgtt cgcgtgggca     900
gagccttcca cagtgaatgt gtctggacct catgttgttg aggctgtcac agtcctgagt     960
gtggacttgg caggtgcctg ttgaatctga gctgcaggtt ccttatctgt cacacctgtg    1020
cctcctcaga ggacagtttt tttgttgttg tgttttttg ttttttttt tttggtagat     1080 gcatgacttg tgtgtgatga gagaatggag acagagtccc tggctcctct actgtttaac    1140
aacatggctt tcttattttg tttgaattgt taattcacag aatagcacaa actacaatta    1200
aaactaagca caaagccatt ctaagtcatt ggggaaacgg ggtgaacttc aggtggatga    1260
ggagacagaa tagagtgata ggaagcgtct ggcagatact cctttttgcca ctgctgtgtg    1320 attagacagg cccagtgagc cgcggggcac atgctggccg ctcctccctc agaaaaaggc    1380
agtgccctaa atccttttta aatgacttgg ctcgatgctg tgggggactg gctgggctgc    1440
tgcaggccgt gtgtctgtca gcccaacctt cacatctgtc acgttctcca cacggggggag   1500 agacgcagtc cgcccaggtc cccgctttct tggaggcag cagctcccgc agggctgaag      1560
tctggcgtaa gatgatggat tgattcgcc ctcctccctg tcatagagct gcagggtgga     1620
ttgttacagc ttcgctggaa acctctggag gtcatctcgg ctgttcctga gaataaaaa     1680 gcctgtcatt tcaaacactg ctgtggaccc tactgggttt ttaaaatatt gtcagttttt    1740
catcgtcgtc cctagcctgc caacagccat ctgcccagac agccgcagtg aggatgagcg    1800
tcctggcaga gacgcagttg tctctgggcg cttgccagag ccacgaaccc cagacctgtt    1860
tgtatcatcc gggctccttc cgggcagaaa caactgaaaa tgcacttcag acccacttat    1920
ttctgccaca tctgagtcgg cctgagatag acttttccct ctaaactggg agaatatcac    1980
agtggttttt gttagcagaa aatgcactcc agcctctgta tcatctaag ctgcttattt     2040 ttgatatttg tgtcagtctg taaatggata cttcacttta ataactgttg cttagtaatt    2100
ggctttgtag agaagctgga aaaaatggt tttgtcttca actcctttgc atgccaggcg      2160
gtgatgtgga tctcggcttc tgtgagcctg tgctgtgggc agggctgagc tggagccgcc    2220
cctctcagcc cgcctgccac ggcctttcct taaaggccat ccttaaaacc agaccctcat    2280
ggctaccagc acctgaaagc ttcctcgaca tctgttaata aagccgtagg cccttgtcta    2340
agtgcaaccg cctagacttt cttttcagata catgtccaca tgtccatttt tcaggttctc    2400
taagttggag tggagtctgg gaagggttgt gaatgaggct tctgggctat gggtgaggtt    2460
```

```
ccaatggcag gttagagccc ctcgggccaa ctgccatcct ggaaagtaga gacagcagtg    2520
cccgctgccc agaagagacc agcaagccaa actggagccc ccattgcagg ctgtcgccat    2580
gtggaaagag taactcacaa ttgccaataa agtctcatgt ggttttatct aaaaaaaaaa    2640
aaaaaaaaaa aaaaa                                                     2655
```

TRIPLE DRUG COMBINATION (METFORMIN, SIMVASTATIN, DIGOXIN) FOR TARGETED TREATMENT OF PANCREATIC CANCER

REFERENCE TO RELATED APPLICATIONS

This application is a U.S. national stage entry of International Application No. PCT/US2017/033512, which claims priority under Section 119(e) from U.S. Provisional Application Ser. No. 62/338,655, filed May 19, 2016, entitled "TRIPLE DRUG COMBINATION (METFORMIN, SIMVASTATIN, DIGOXIN) FOR TARGETED TREATMENT OF PANCREATIC CANCER" by Francis C. Brunicardi et al., the contents of which are incorporated herein by reference.

SEQUENCE LISTING

The instant application contains a Sequence Listing which has been submitted electronically in ASCII format and is hereby incorporated by reference in its entirety. Said ASCII copy, created on May 11, 2017, is named 30435_312-WO-U1_SL.txt and is 5,194 bytes in size.

TECHNICAL FIELD

The invention relates to therapeutic compositions and methods for the treatment of pancreatic cancer.

BACKGROUND OF THE INVENTION

Pancreatic cancer accounts for about 3% of all cancers in the United States and about 7% of cancer deaths. Of the different types of pancreatic cancers, more than 90% of the pancreatic cancers found in patients is pancreatic ductal adenocarcinoma (PDAC). PDAC is one of the deadliest cancers and ranks fourth in cancer-related deaths in the United States [1]. PDAC has an overall 5-year survival rate of less than 5%.

Conventional therapies for pancreatic cancer involve either neoadjuvant treatment with chemotherapy and/or radiation therapy or surgical removal followed by either adjuvant chemotherapy or radiation therapy. However, there are currently no effective chemotherapies for pancreatic cancer that prolong life beyond a few months. There is also significant toxicity associated with such chemotherapies. The standard first-line treatment for treating pancreatic cancer is gemcitabine, which was approved by the U.S. Food and Drug Administration (FDA) in 1996. While gemcitabine has become a standard palliative therapy for treating pancreatic cancer since its approval in 1996, there has been little improvement in pancreatic cancer treatment. Although treatment of gemcitabine increases the 5-year survival to approximately 20%, pancreatic cancers remain difficult to treat effectively. Furthermore, less than 20% of patients are eligible for potentially curative resection and the 5-year survival for resectable PDAC is only 25% [2-6]. Current adjuvant therapy includes gemcitabine, erlotinib, capecitabine, FOLFIRINOX (a combination of 5-fluorouracil, irinotecan, and oxaliplatin, plus the adjuvant folinic acid), and gemcitabine with nab-paclitaxel; sadly, the conventional therapeutic regimens all typically confer a survival advantage of only about six months [7].

Accordingly, there is a need in the art for improved methods and compositions for treating such cancers. The invention disclosed herein meets this need using a combination of well-known and FDA approved therapeutic compounds. As discussed below, this combination of therapeutic compounds provides an unexpectedly potent therapy for pancreatic cancers.

SUMMARY OF THE INVENTION

As noted above, because the five-year survival rate for pancreatic cancer is only 6%, there is a serious need for new therapies that will extend the lives of patients diagnosed with this disease. As disclosed in detail below, it has been discovered that a combination of three well known and FDA approved compounds can significantly suppress the proliferation of pancreatic cancer cells. The data from in vitro and in in vivo studies of these agents that is presented herein shows that this combination significantly suppresses cancer cell growth in clinically relevant models. Interestingly, combinations of these agents are observed to have a synergistic effect in suppressing the growth of pancreatic tumor cells, one not observed when these compounds are administered individually.

The invention disclosed herein has a number of embodiments. One embodiment is a composition of matter comprising a combination of metformin or a metformin analog, a statin such as simvastatin, and a cardiac glycoside such as digoxin. In the illustrative working embodiments that are discussed below, the composition of matter comprises a combination of metformin, simvastatin, and digoxin. The composition of matter can also comprise a pharmaceutically acceptable carrier, typically one selected to facilitate the oral delivery of metformin, simvastatin, and digoxin. In illustrative embodiments of the invention, the composition is formed as a time release formulation and is disposed in a capsule or tablet. Typically, the composition comprises amounts of agents such as metformin, simvastatin, and digoxin that are sufficient to inhibit in vivo growth of a human pancreatic ductal adenocarcinoma cell (PDAC) when administered orally to a patient diagnosed with pancreatic ductal adenocarcinoma. In one working embodiment of the invention, the composition comprises 5-80 milligrams po of simvastatin; 500-2550 milligrams po of metformin; and 0.125-0.250 milligrams po of digoxin. In another embodiment of the invention, the composition comprises 5-80 po milligrams of simvastatin; 500-2550 milligrams po of metformin; and 62.5-500 micrograms po of digoxin.

Other embodiments of the invention include methods of inhibiting the growth of pancreatic cancer cells by combining these cells with metformin or a metformin analog, a statin such as simvastatin, and a cardiac glycoside such as digoxin. In illustrative embodiments of the invention, a patient diagnosed with pancreatic cancer is administered therapeutically effective amounts of a combination of metformin, simvastatin, and digoxin. While the therapeutic agents can be administered separately, in typical embodiments, these agents are administered together, for example in a triple drug composition as described above. In certain embodiments, the patient is administered metformin, simvastatin, and digoxin disposed together in a capsule or tablet as a time release formulation. In one illustrative example, the patient is administered 5-80 milligrams po of simvastatin; 500-2550 milligrams po of metformin; and 0.125-0.250 milligrams po of digoxin. In another example, the patient is administered 500-2550 milligrams/day of metformin, 5-80 milligrams/day of simvastatin, and 750-1250 micrograms/day of digoxin. In certain embodiments of the invention, the patient is administered the three drug combination as well as an additional agent such as gemcitabine or paclitaxil.

Yet another embodiment of the invention is a method of inhibiting growth of a population of cells (e.g. pancreatic cancer cells) that are expressing a specific macromolecule such as the BIRC5 protein. This method typically comprises combining the population of cells with amounts of metformin, simvastatin, and digoxin sufficient to inhibit expression of BIRC5 protein in the population of cells, thereby inhibiting the growth of the population of cells. In an illustrative embodiment of the invention, the cells are a pancreatic cancer cell lineage such as pancreatic ductal adenocarcinoma cells. In typical embodiments of the invention, the metformin, simvastatin, and digoxin are combined with a population of cells such as pancreatic cancer cells in an amount sufficient to promote apoptosis in the population of cells. Typically, the population of cells is combined with metformin, simvastatin and digoxin in vivo. In another embodiment, the population of human cells are combined with metformin, simvastatin and digoxin in vitro. In some embodiments, the methods can further comprise observing the population of human cells for evidence of growth inhibition and/or cell death (e.g. via positron emission tomography).

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

Figure 14:
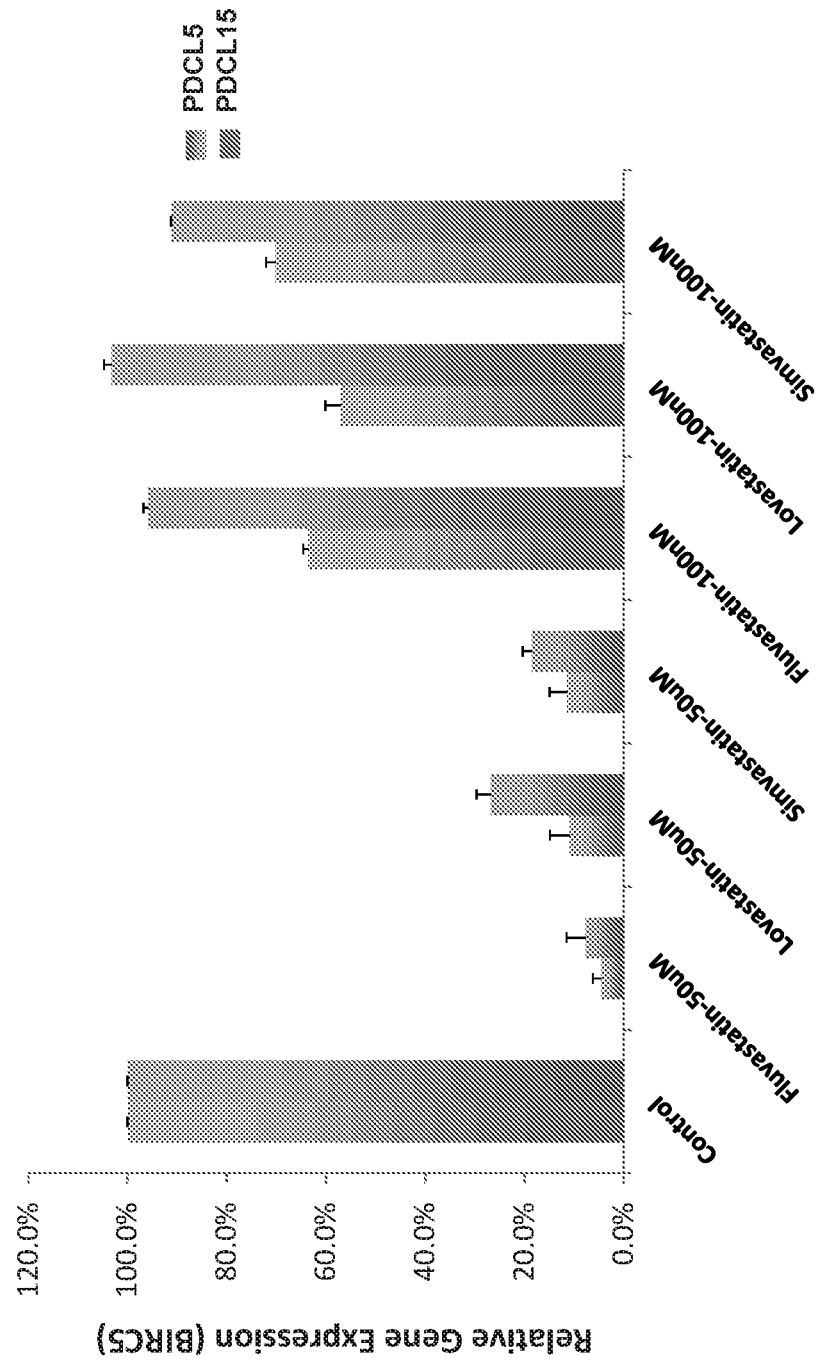
Figure 15:
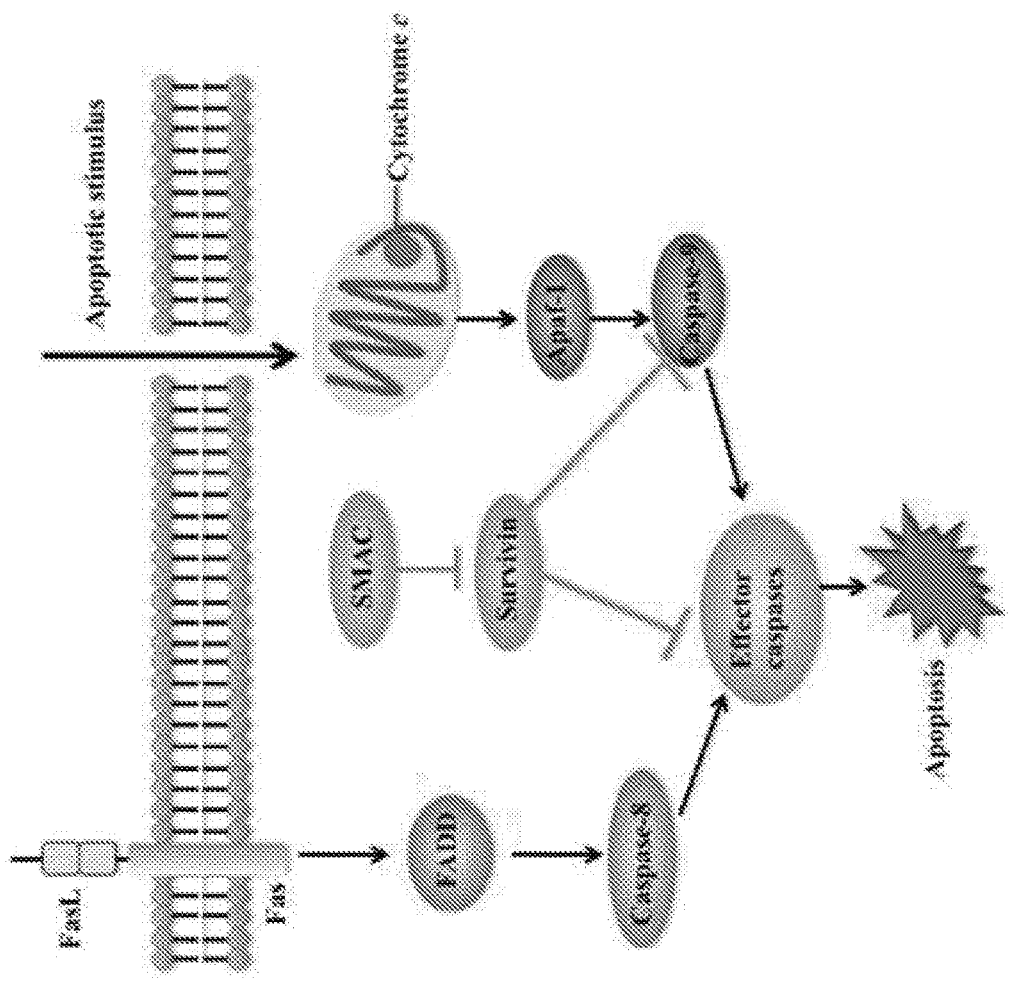
Figure 16:
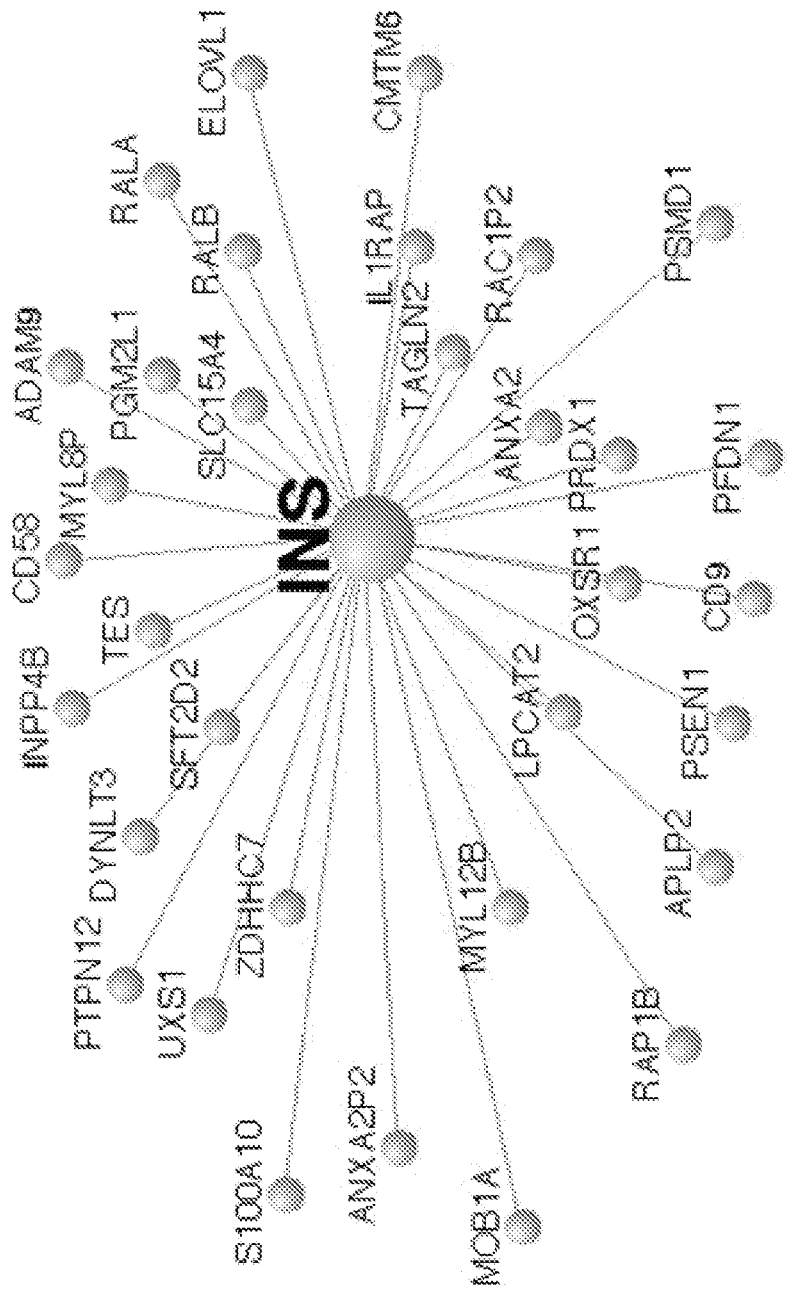
Figure 17:
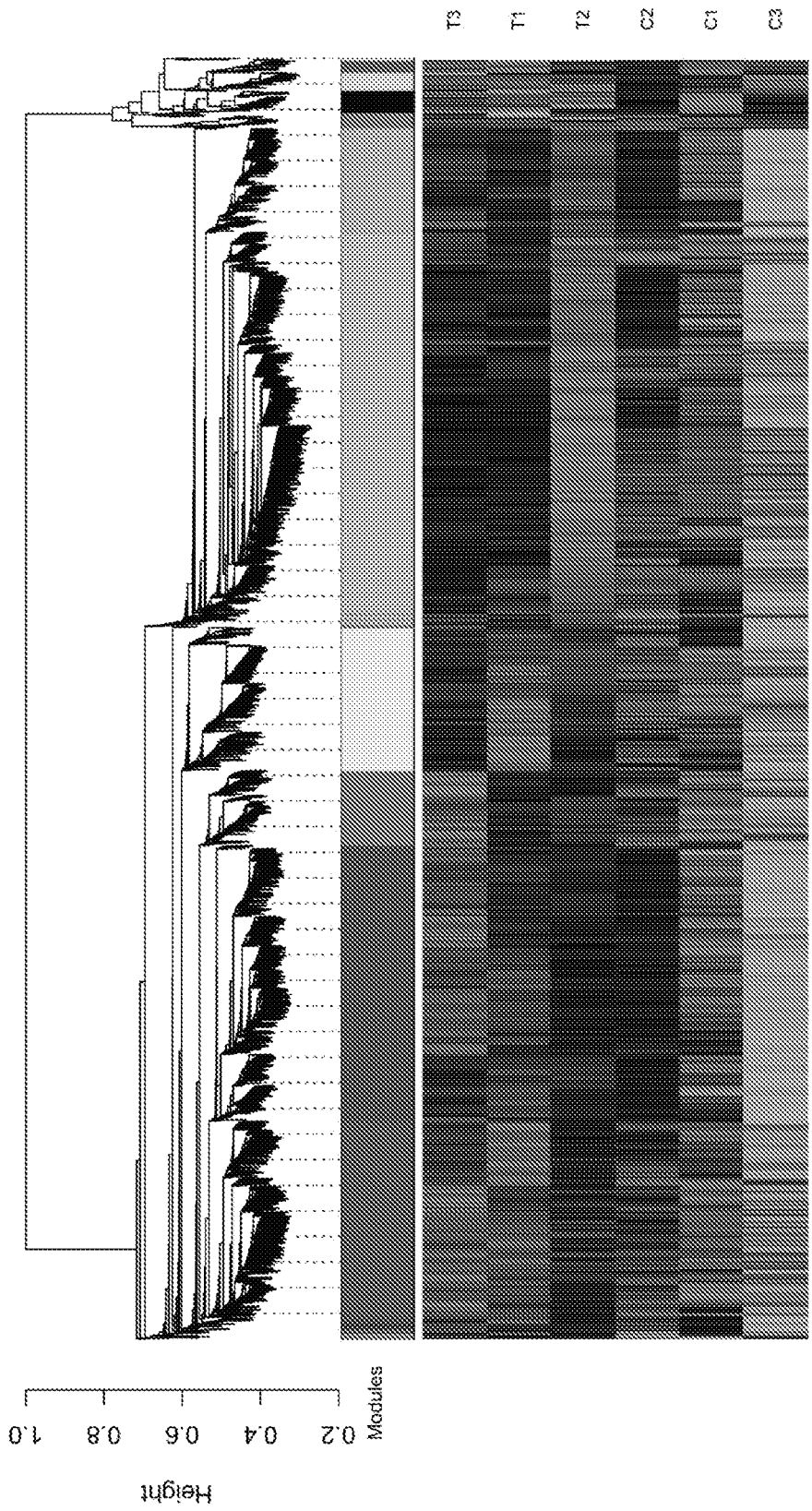
Figure 18:
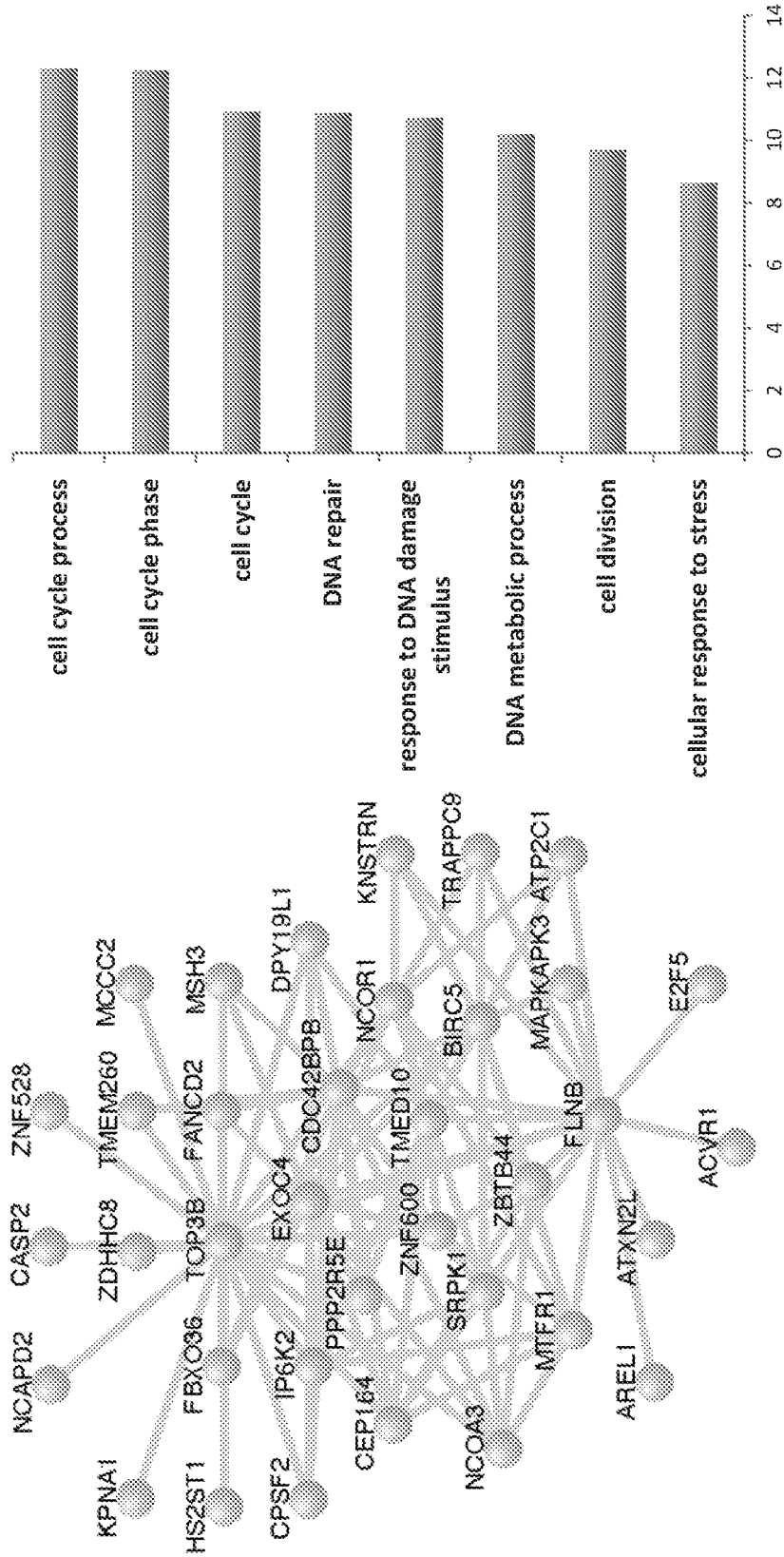
Figure 19:
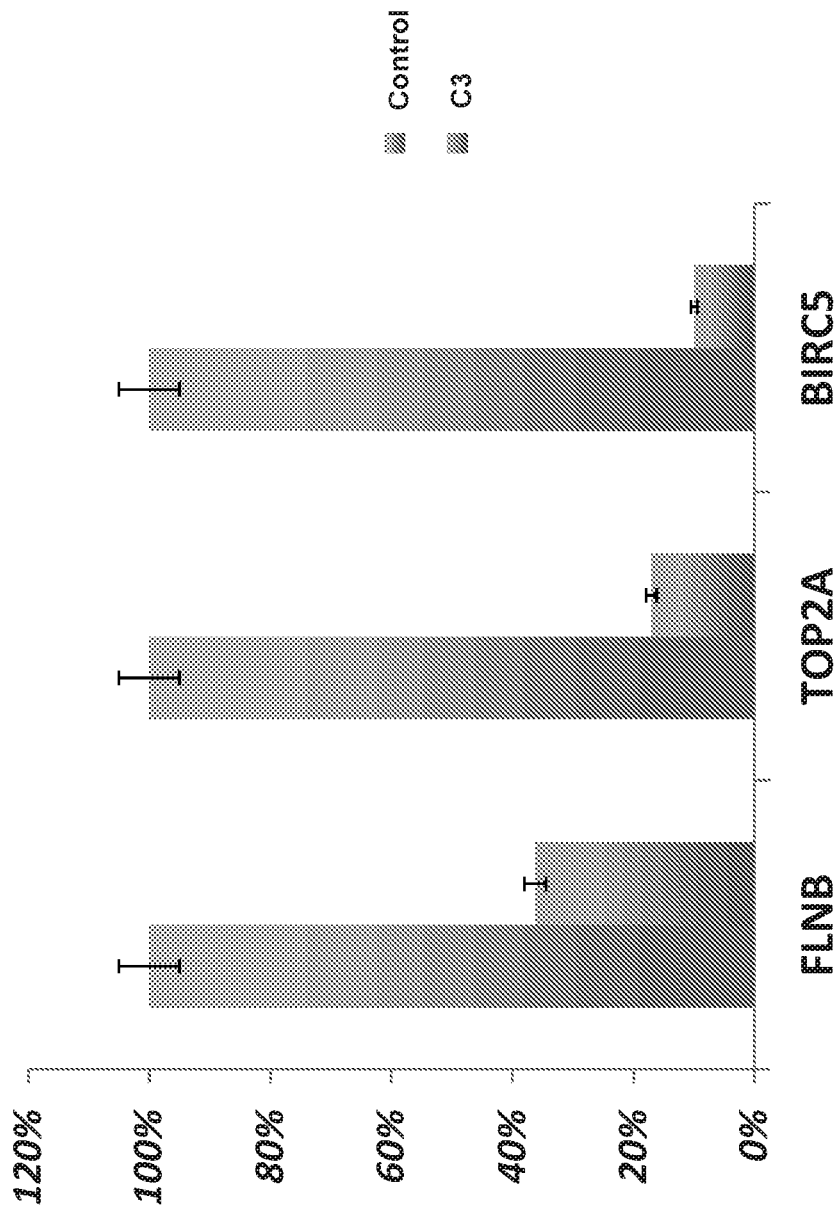
Figure 20:
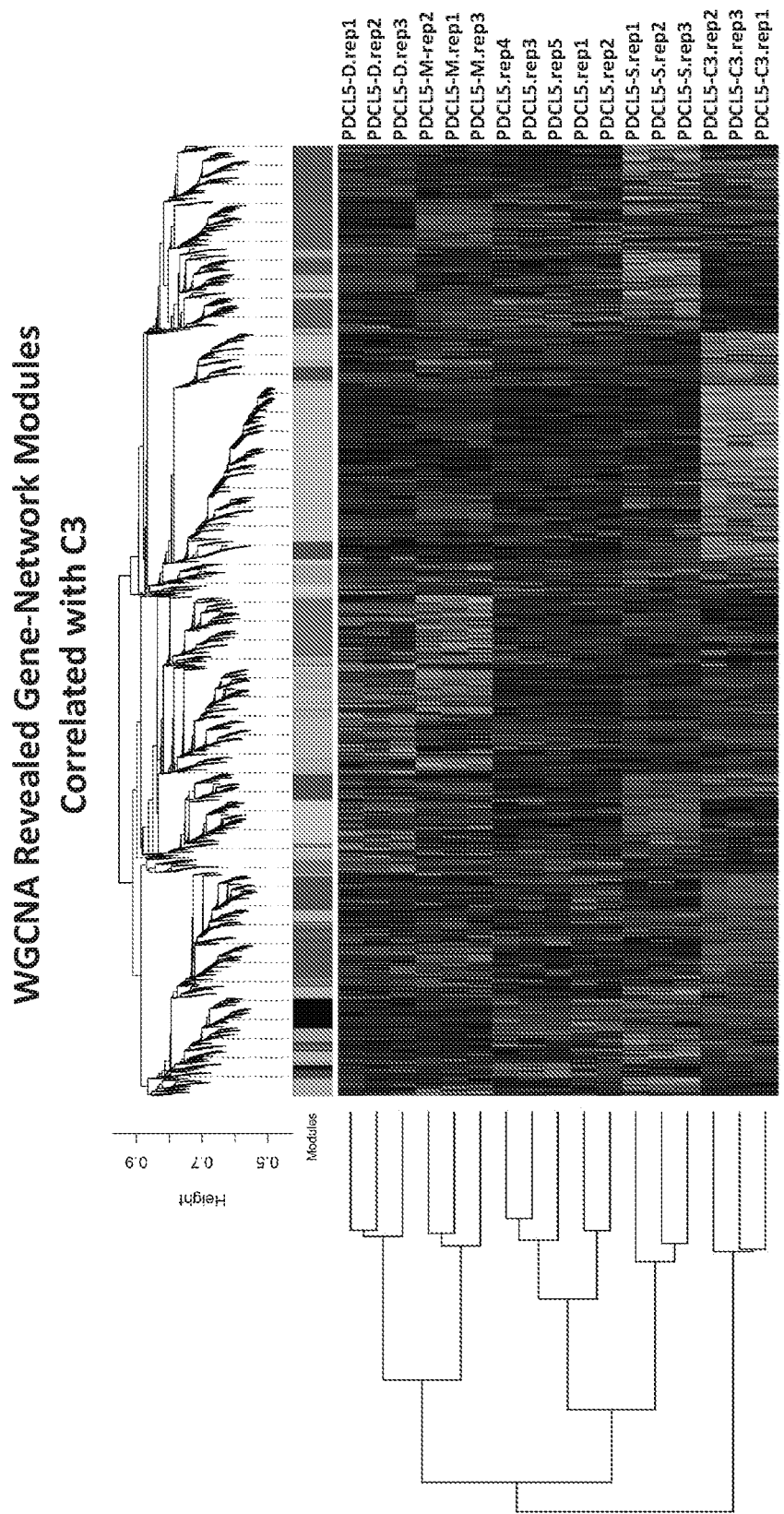
Figure 21:
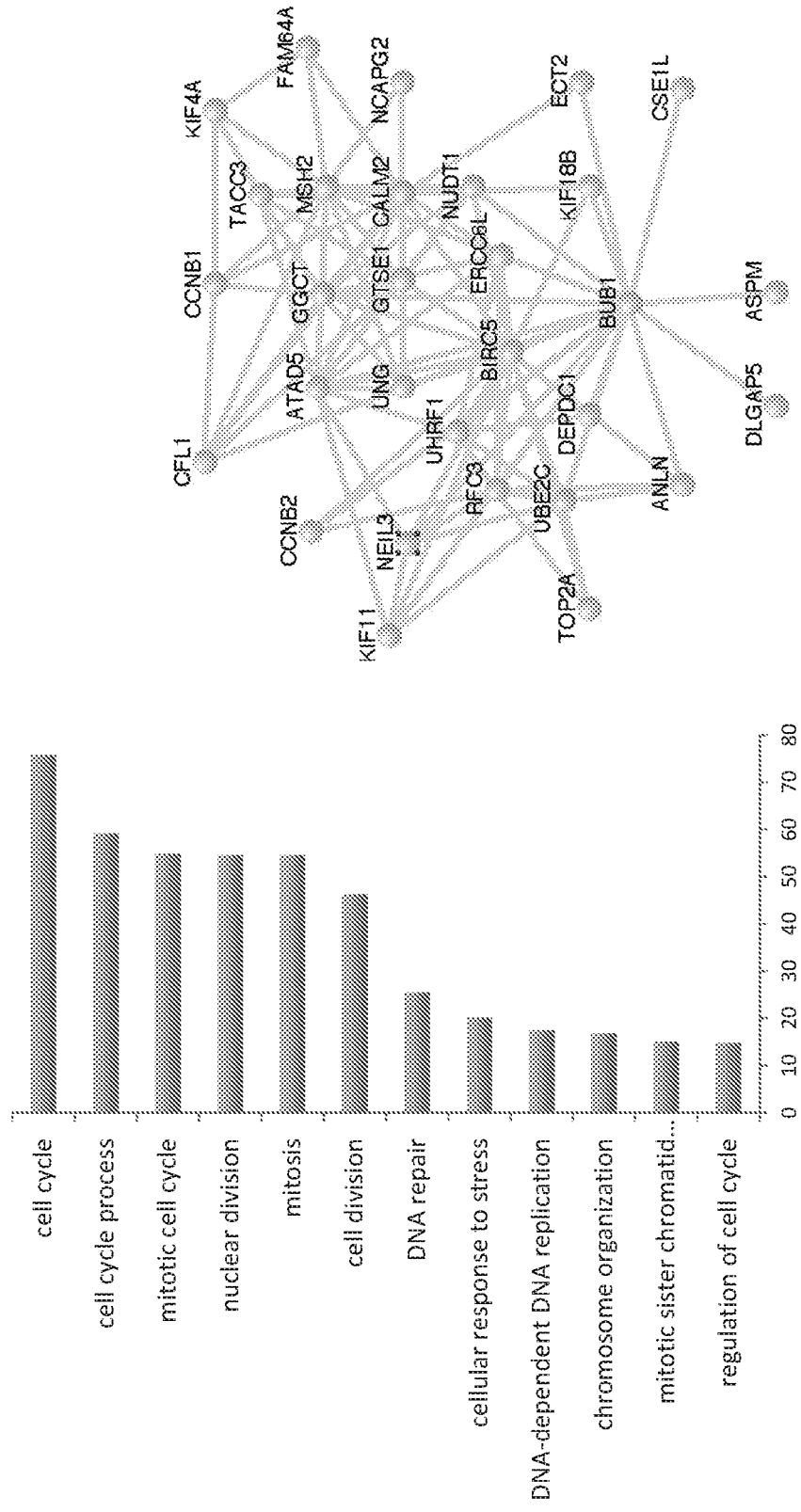
Figure 22:
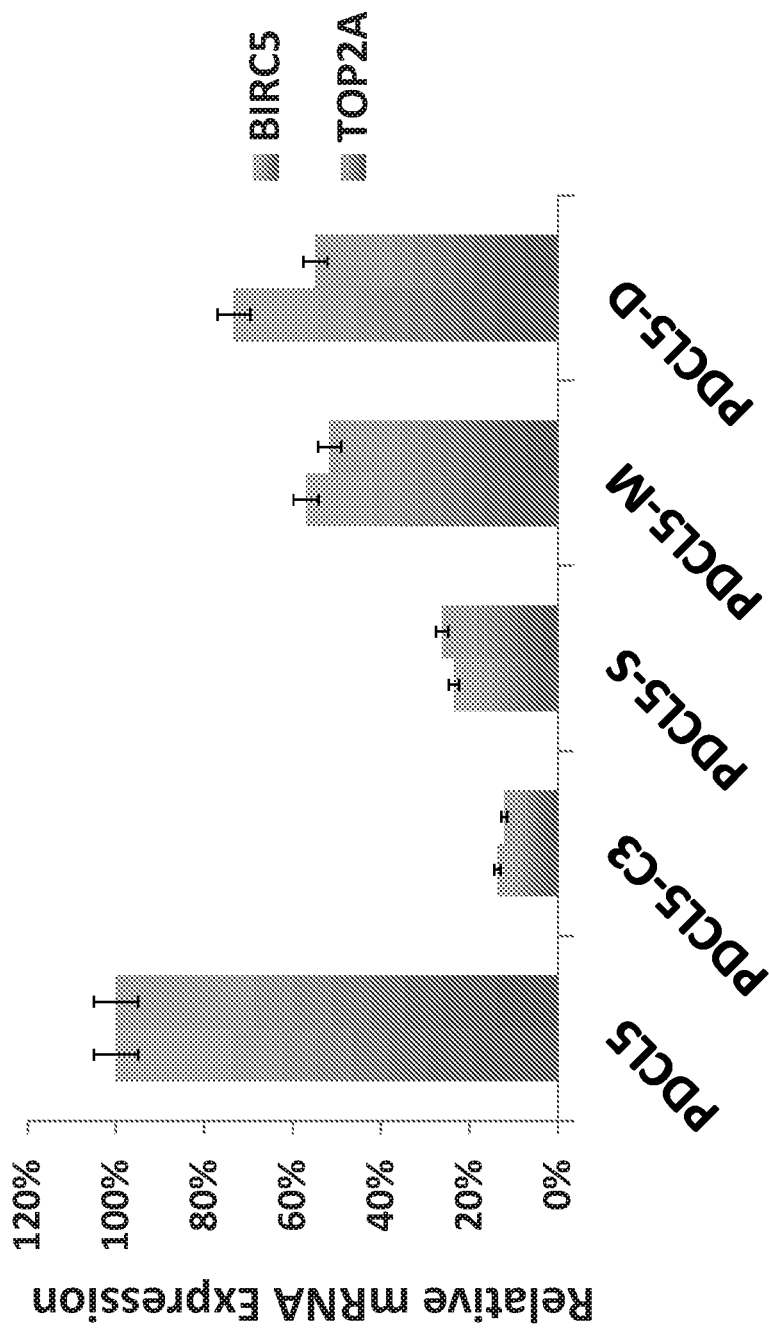
Figure 23:
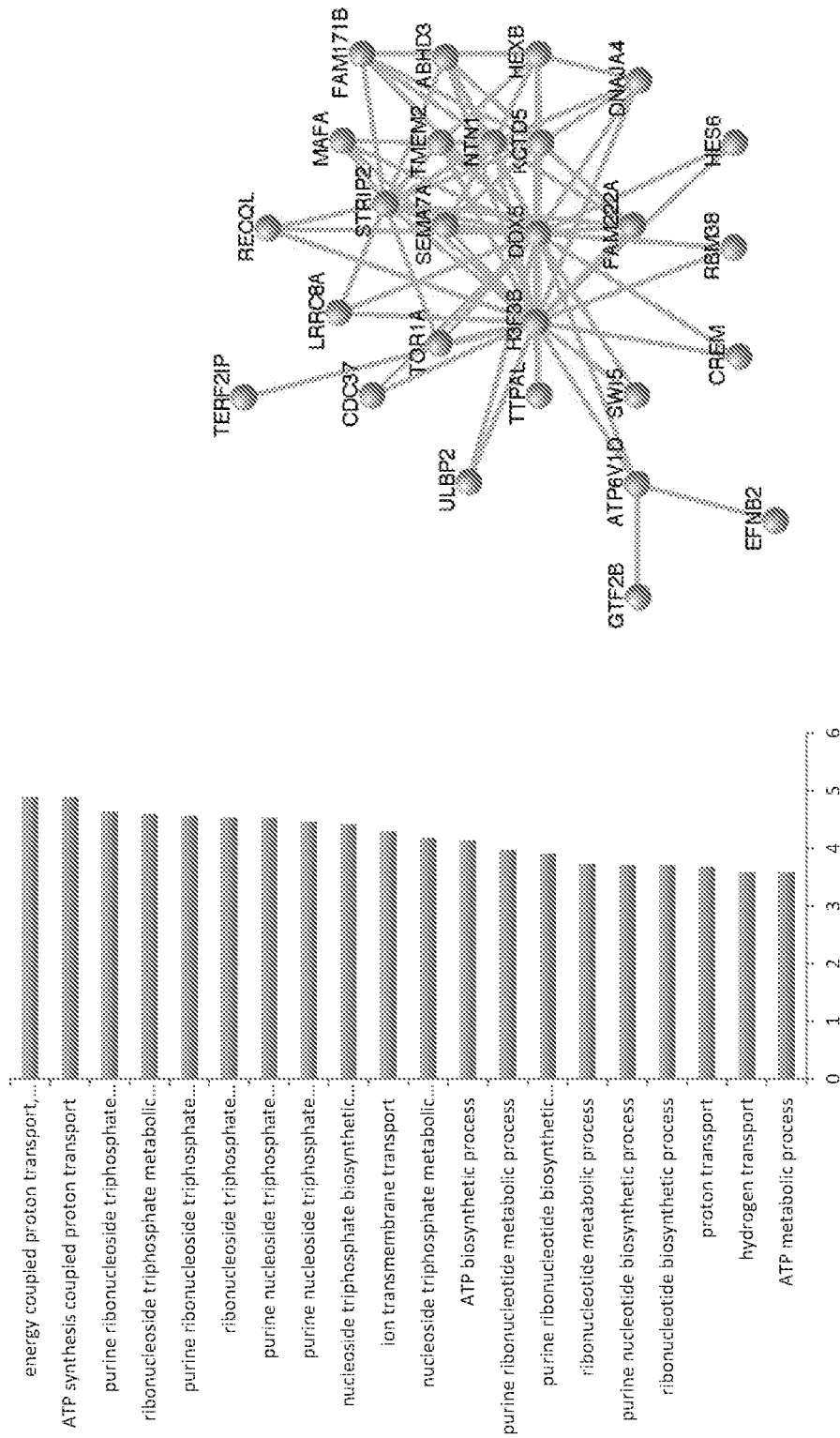
Figure 24:
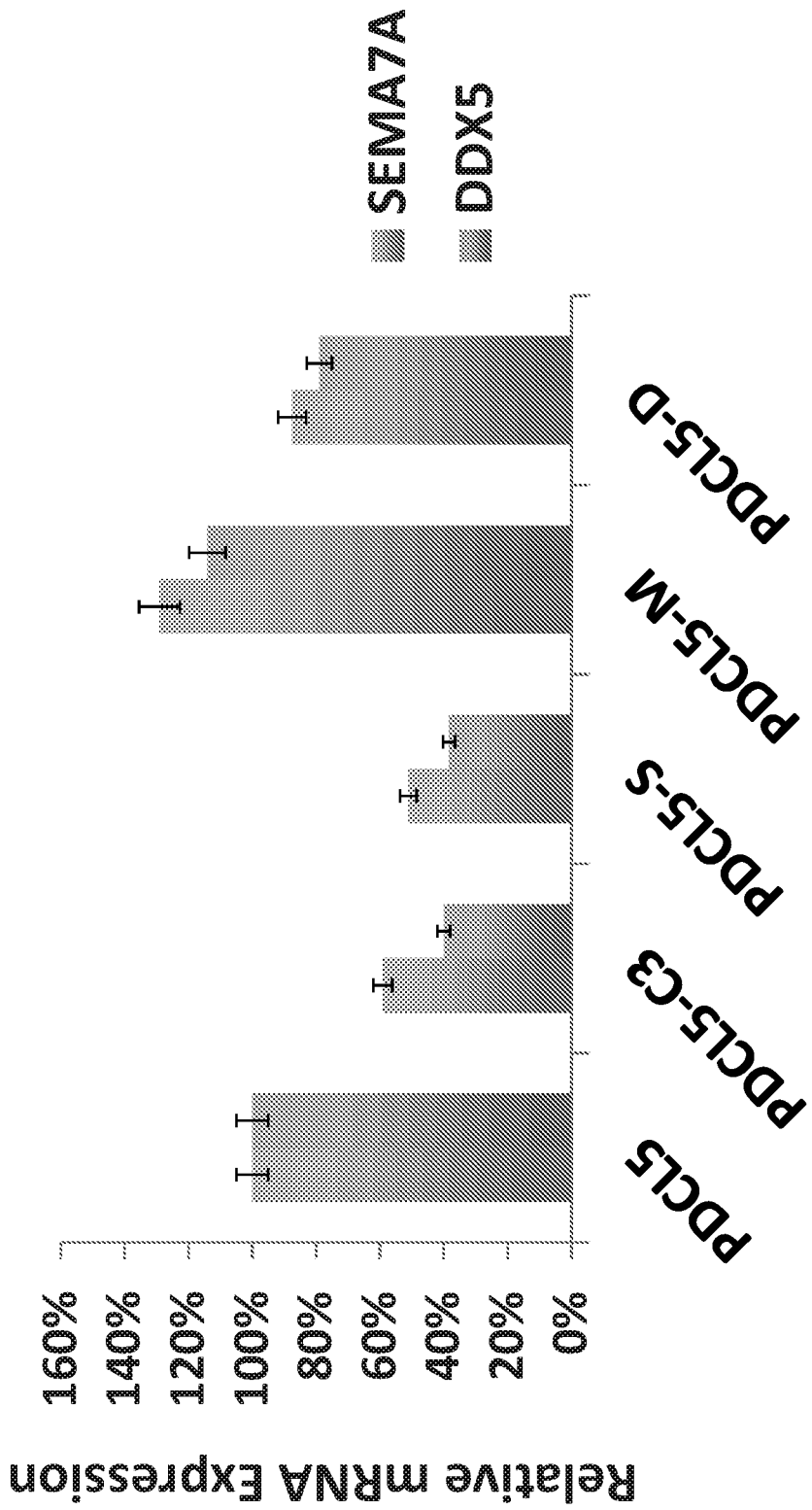
Figure 25:
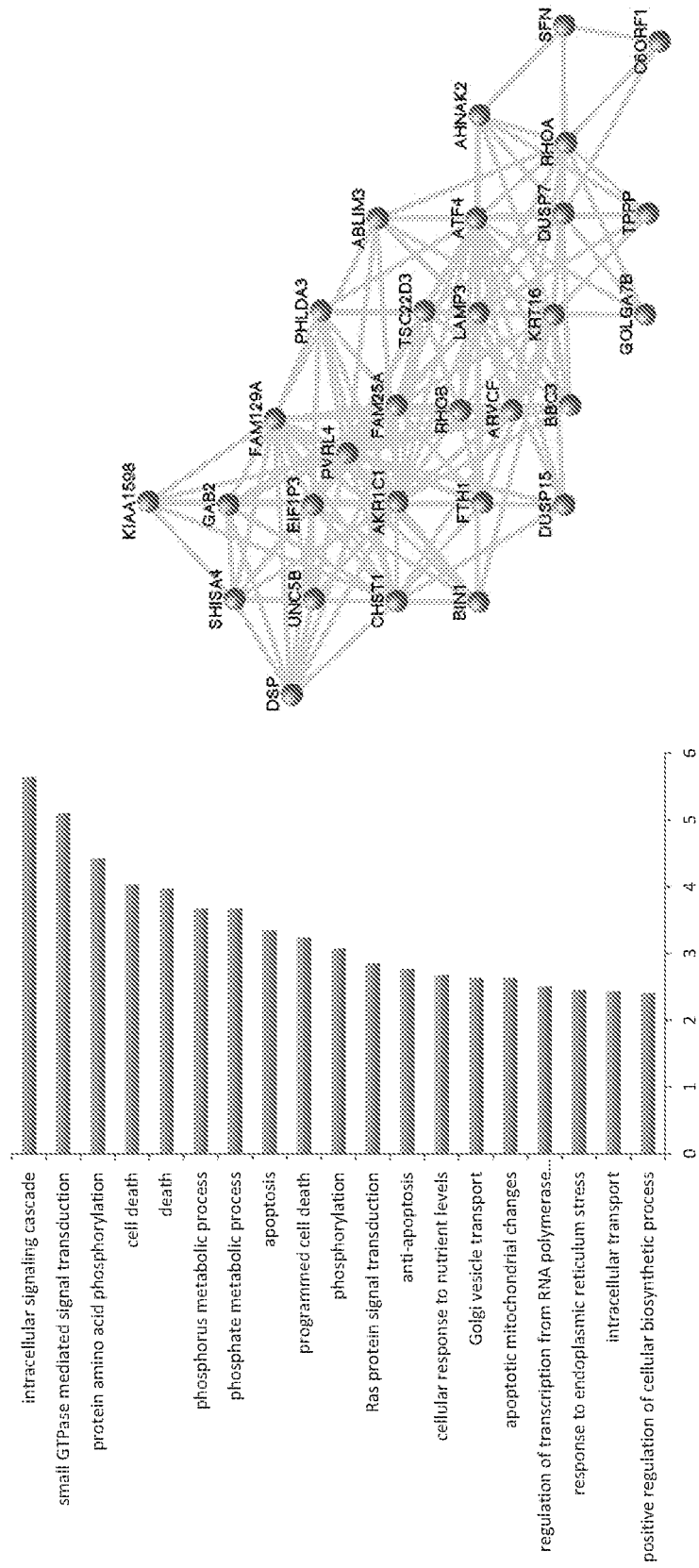
Figure 26:
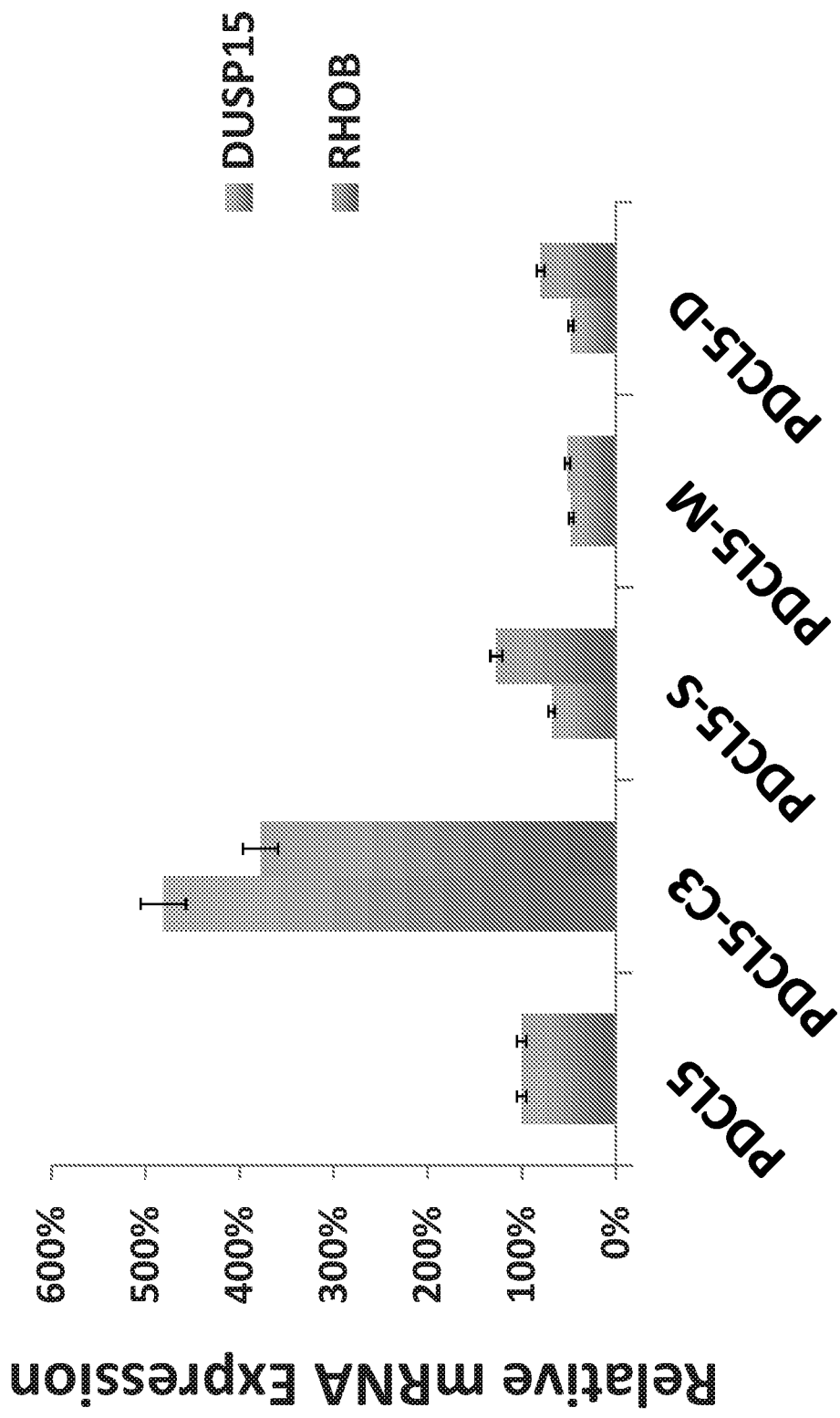
Figure 27:
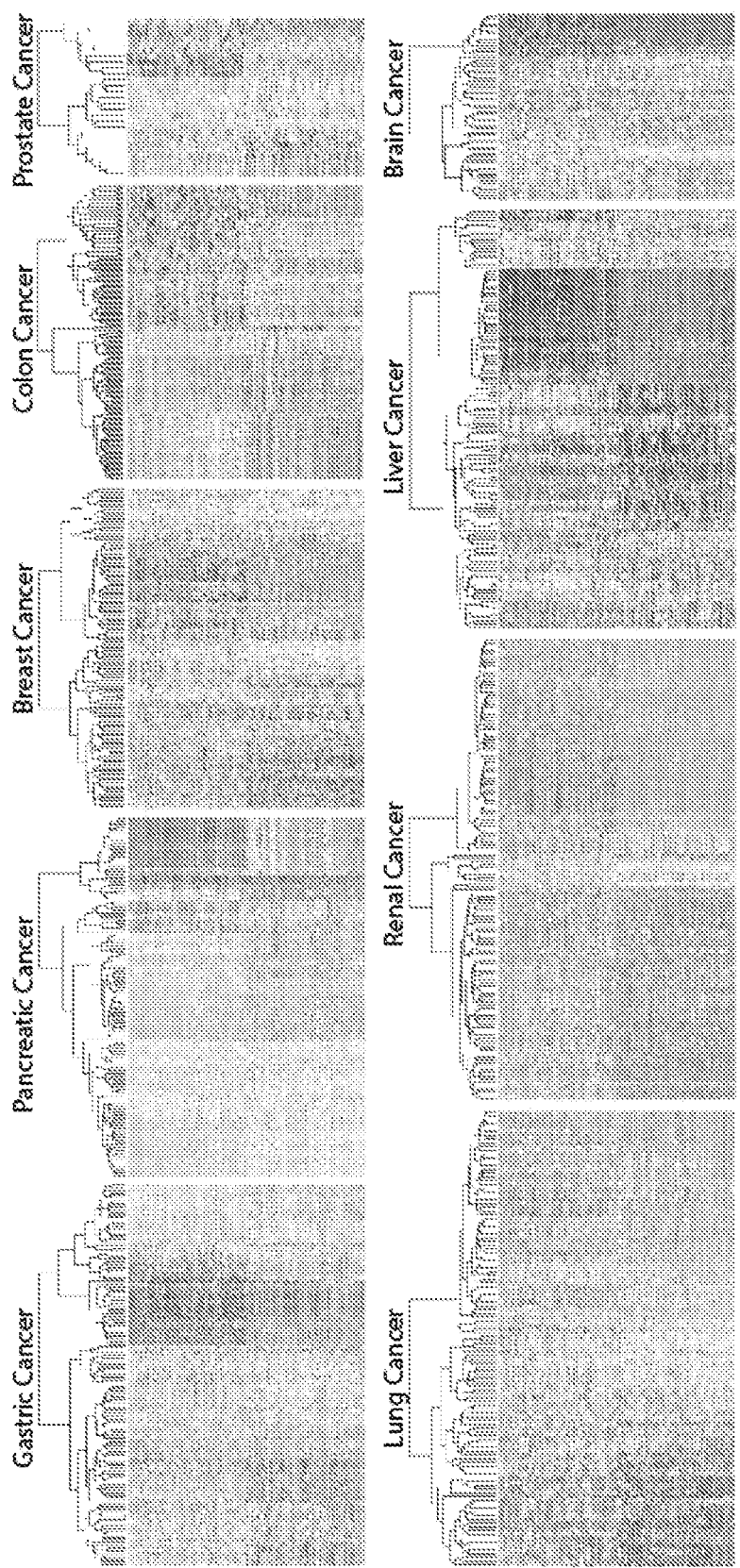
Figure 28:
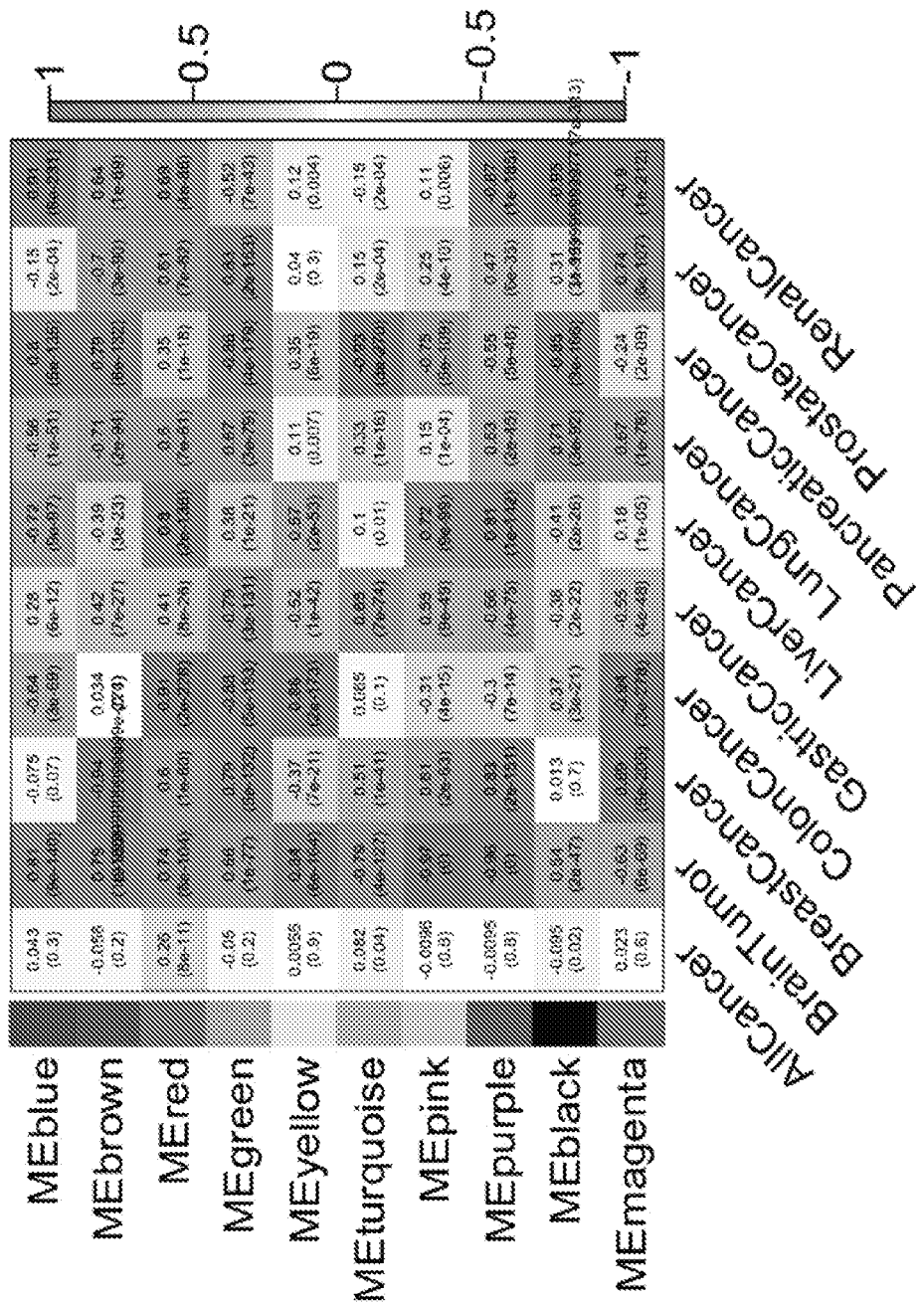
Figure 29:
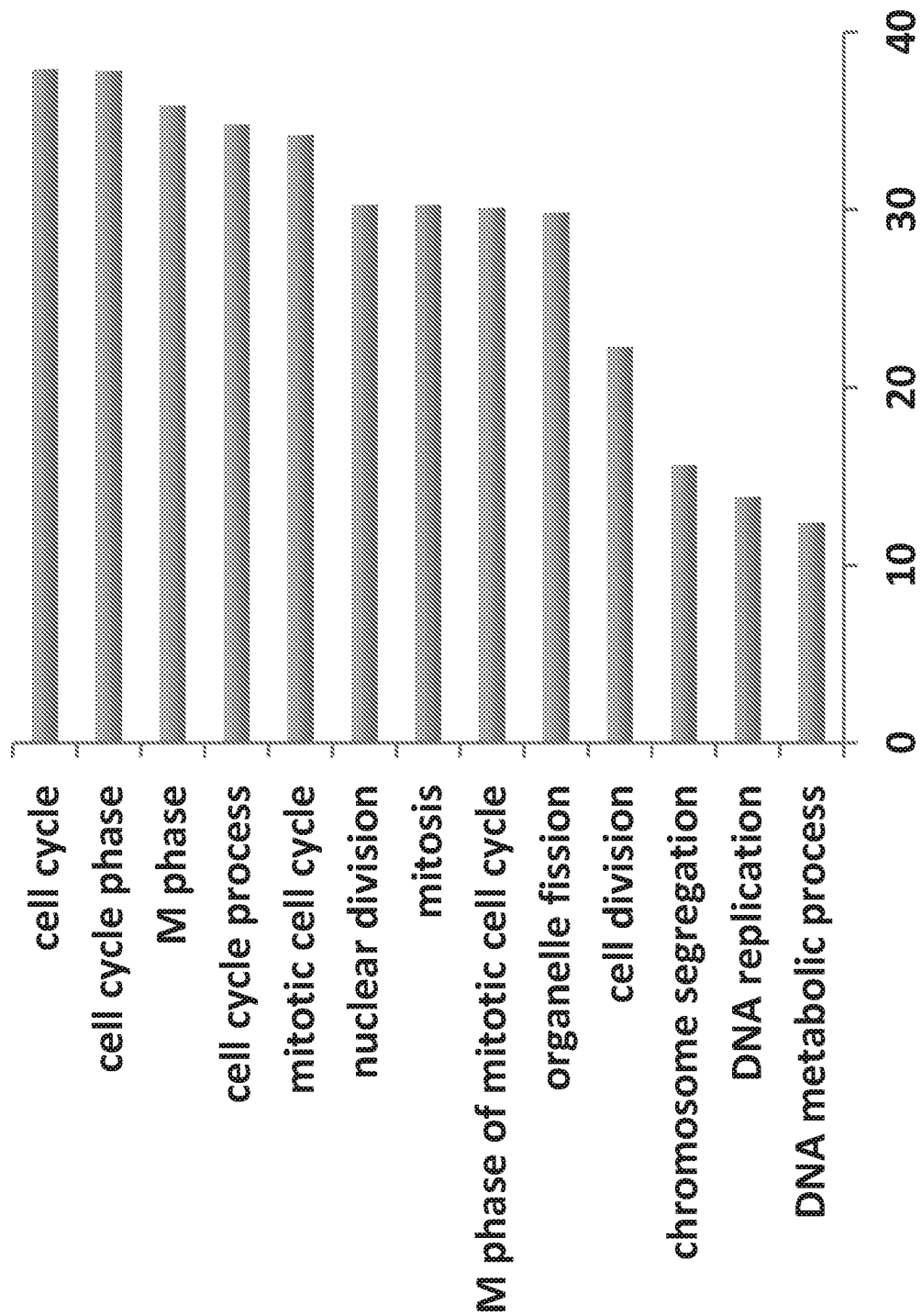
Figure 30:
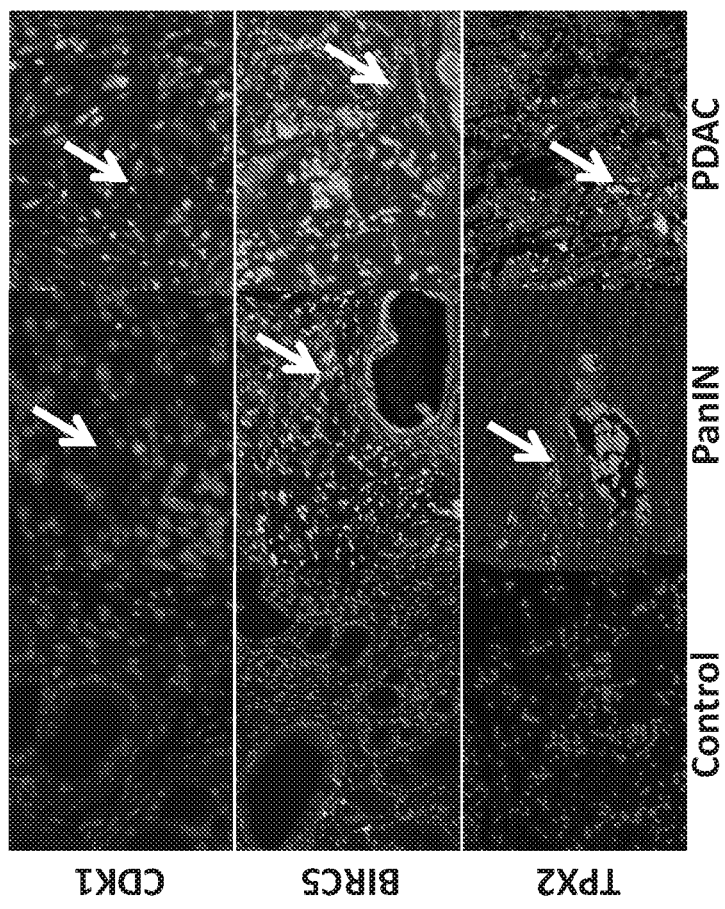
Figure 30:
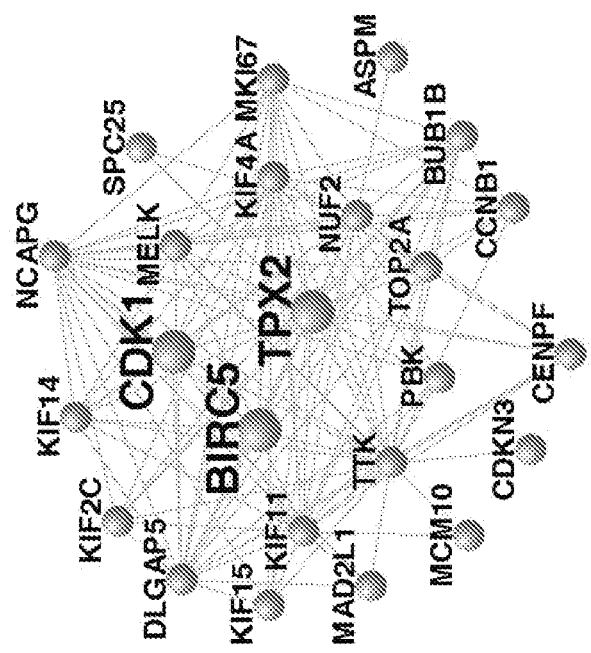
Figure 31:
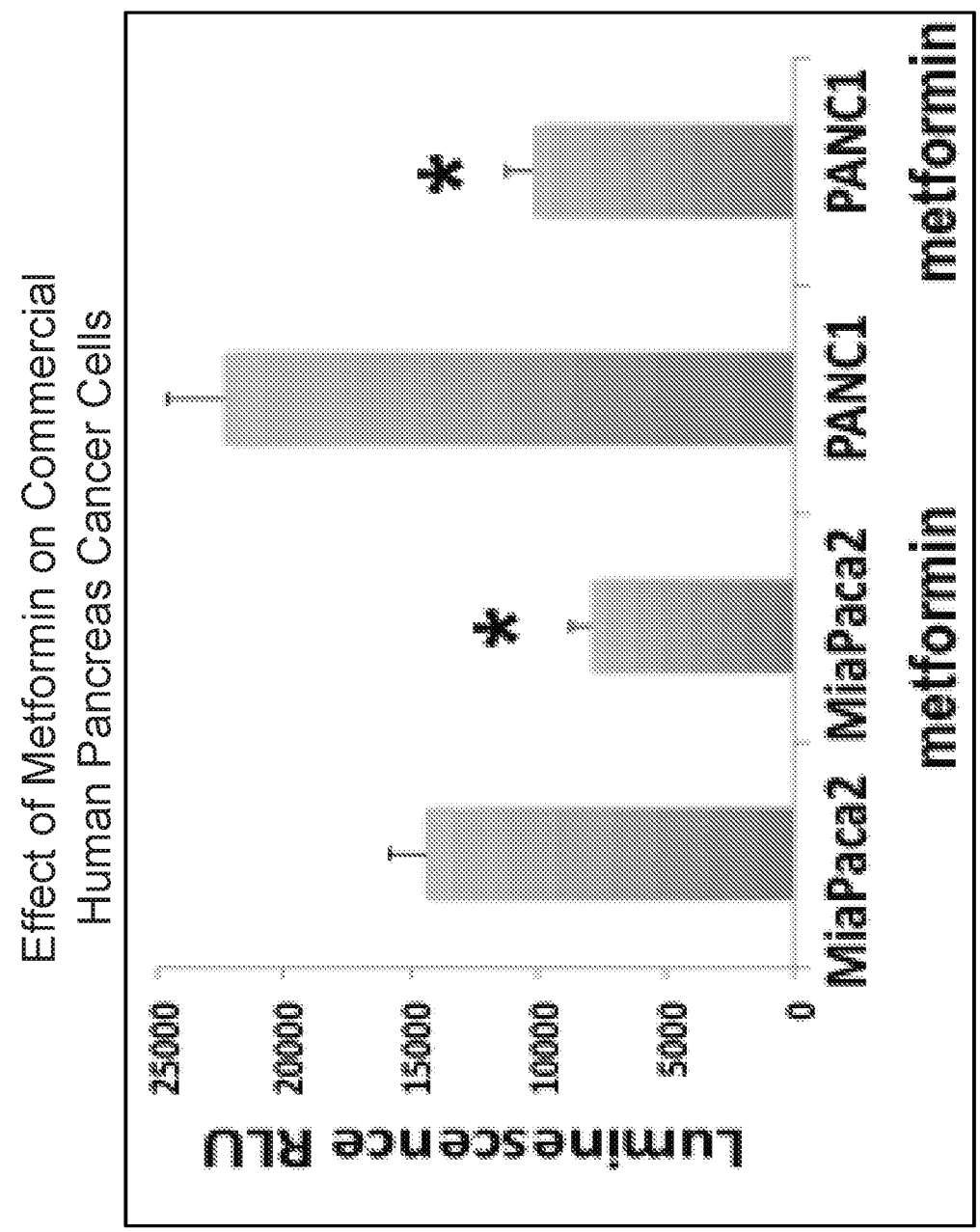
Figure 32:
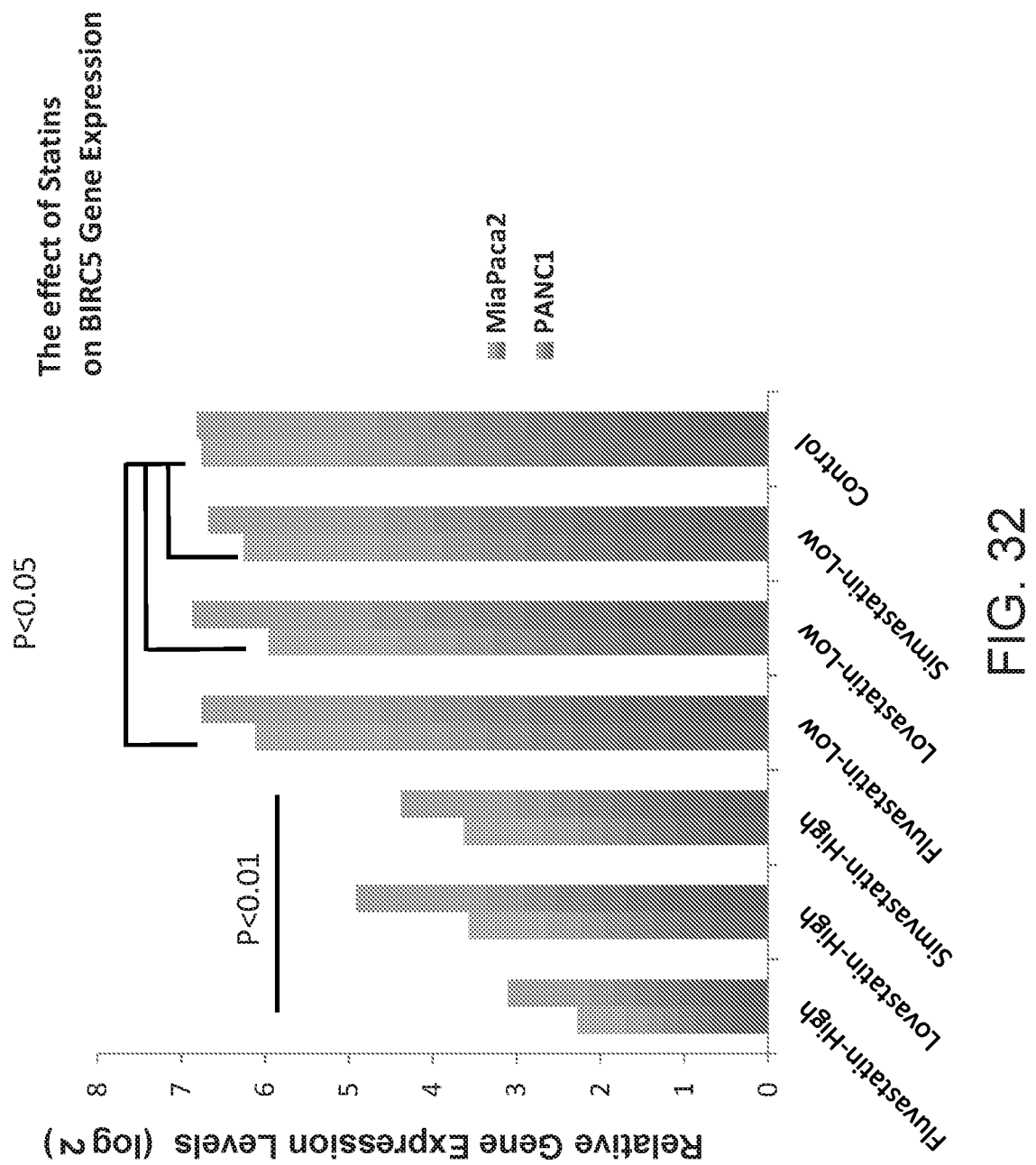
Figure 33:
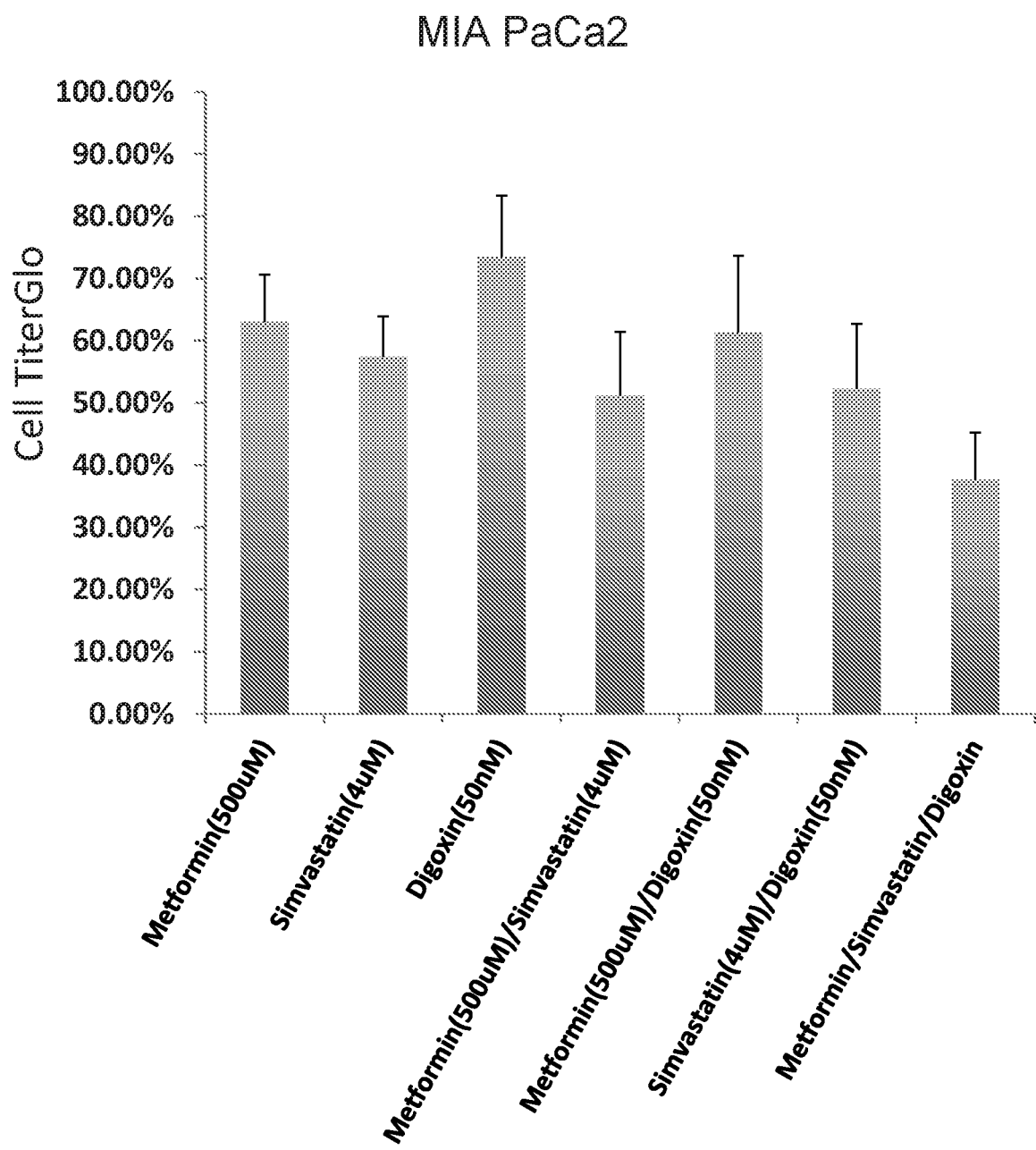
Figure 34:
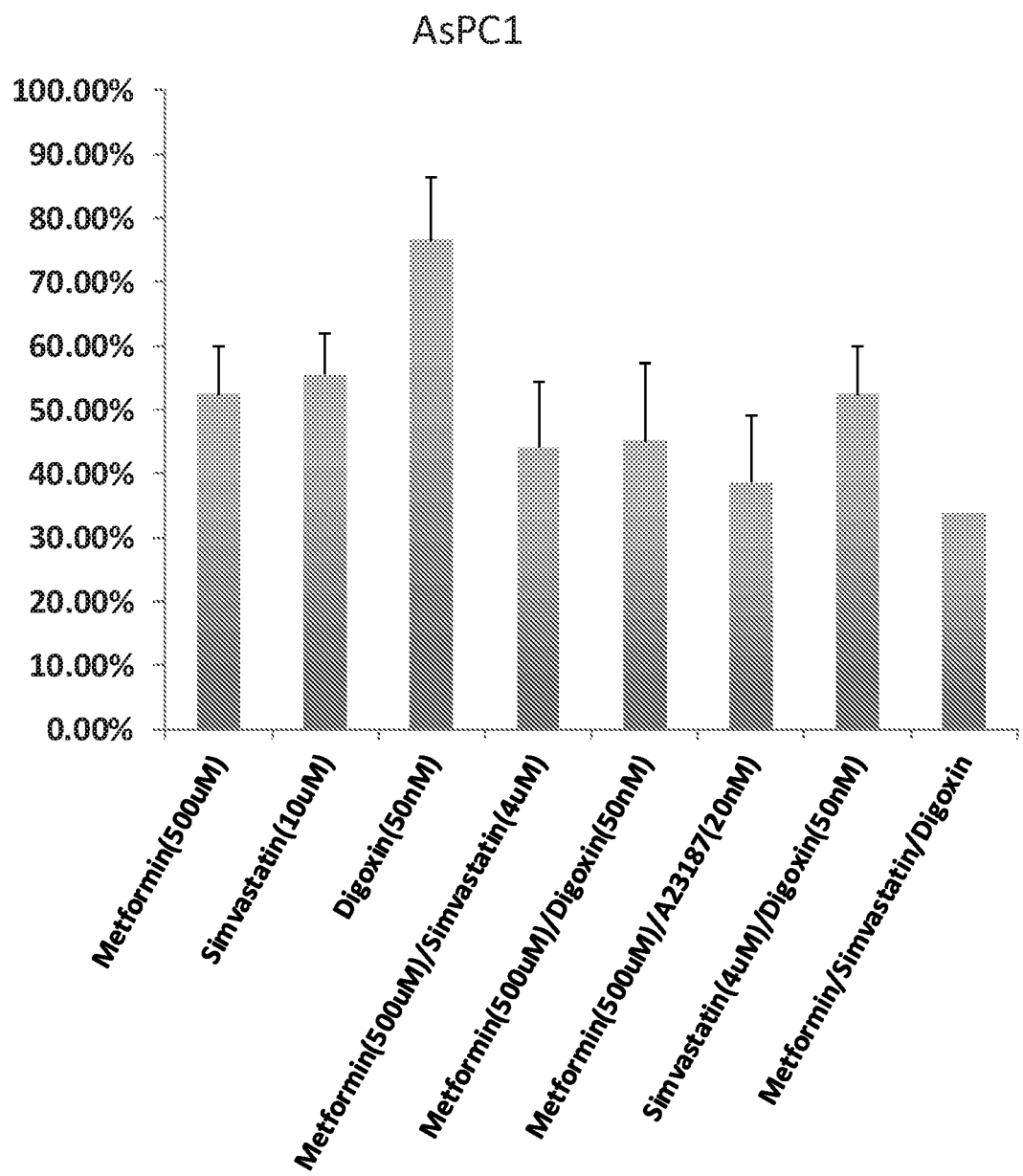
Figure 35:
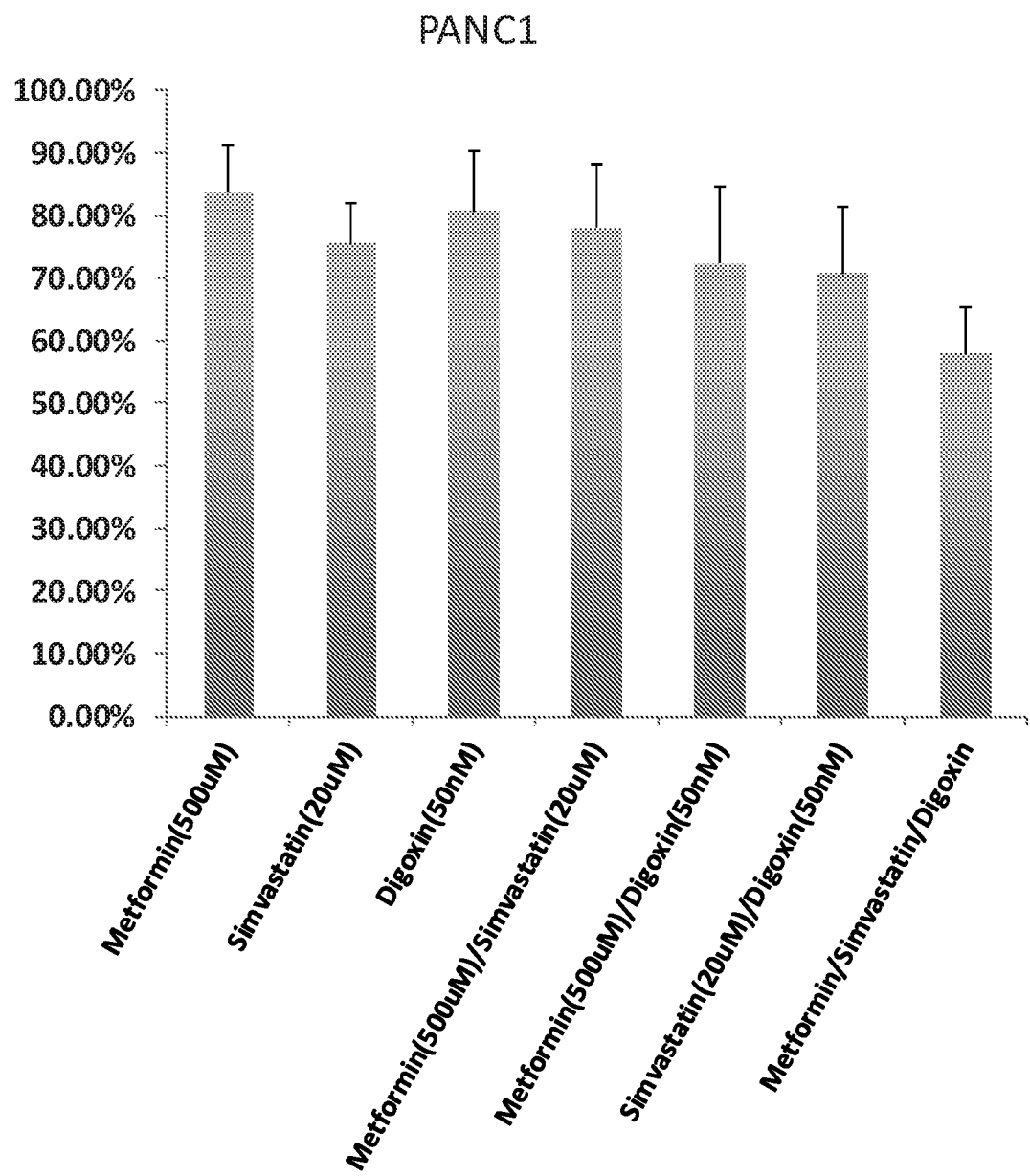
Figure 36:
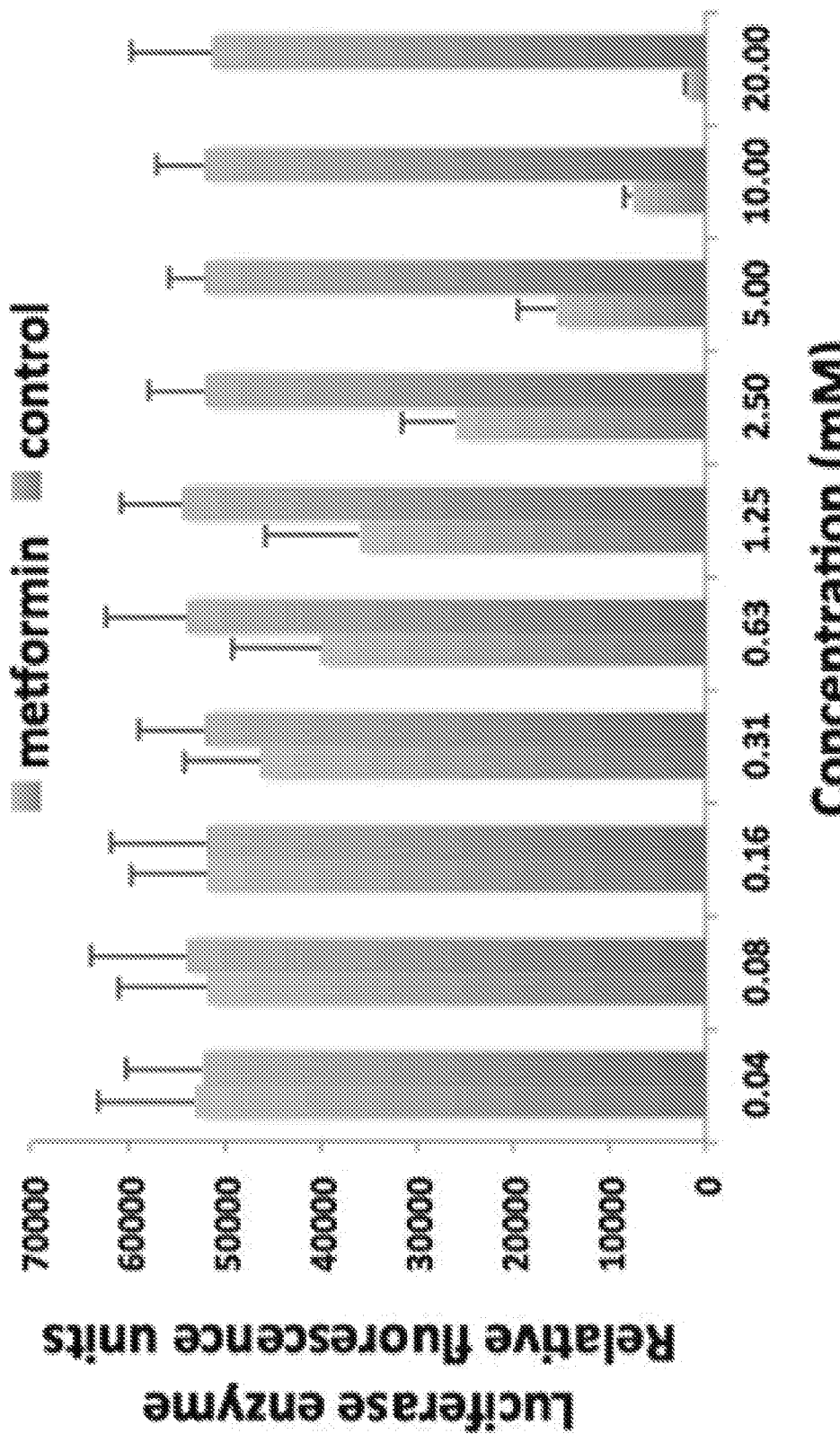
Figure 37:
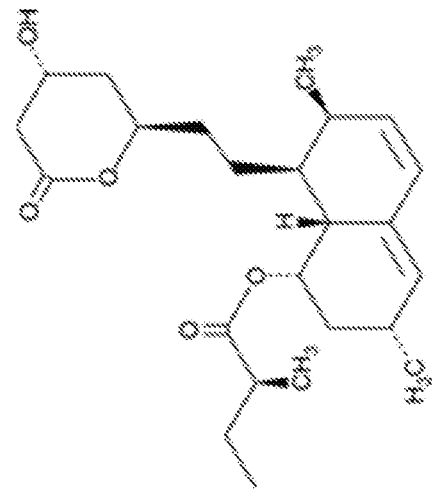
Figure 37:
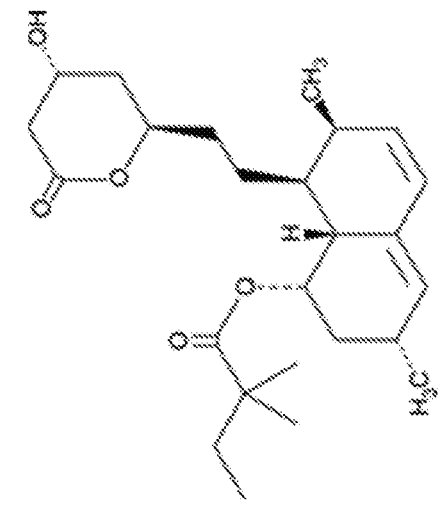
Figure 37:
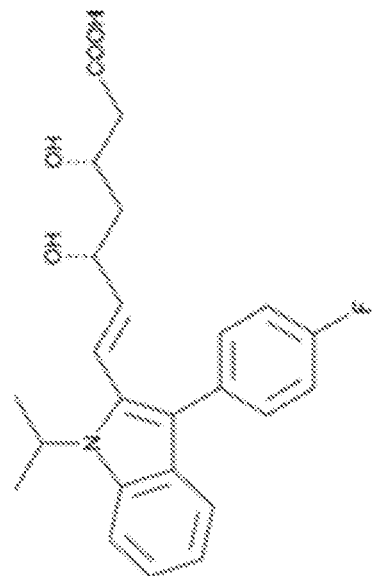
Figure 38:
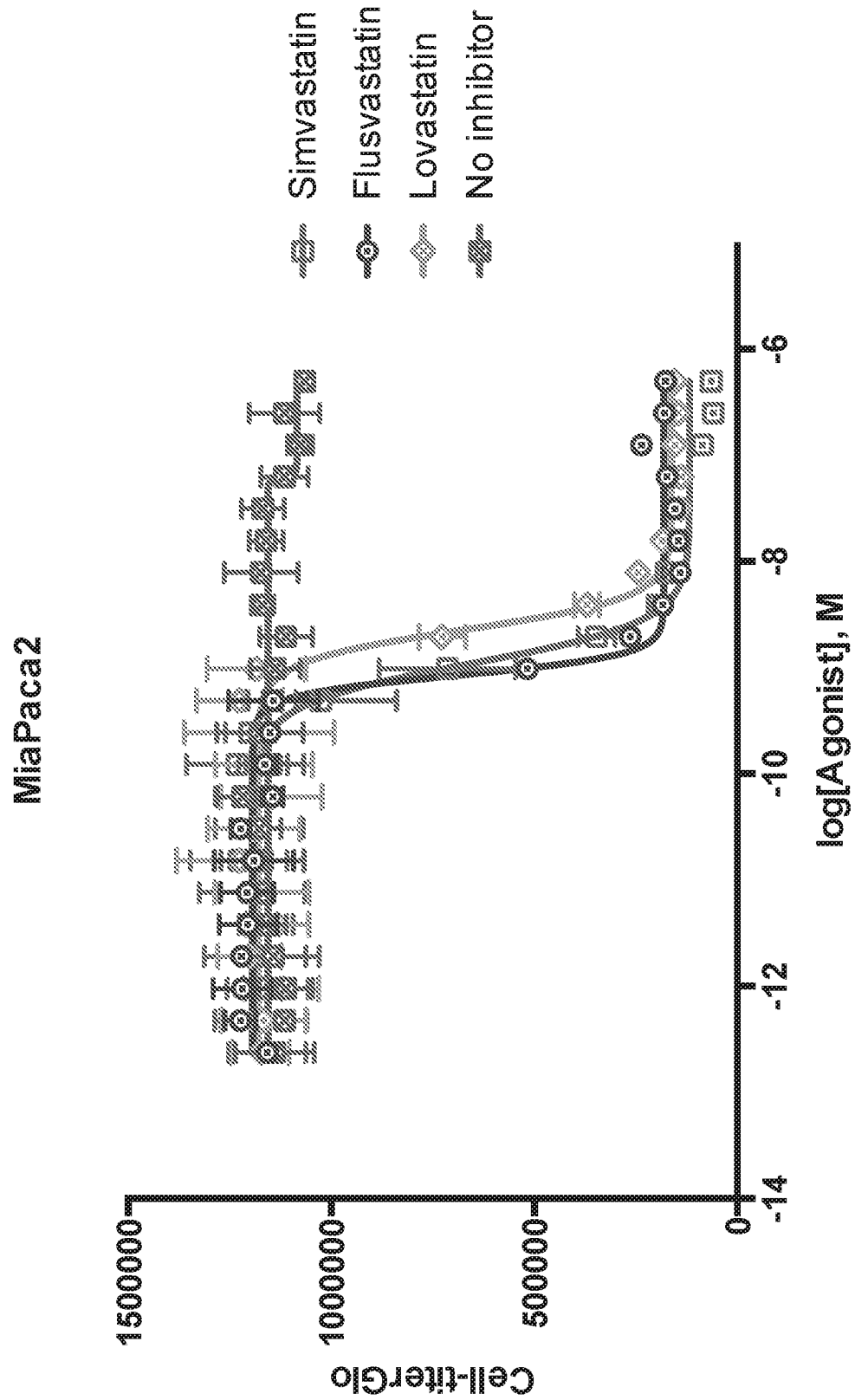
Figure 39:
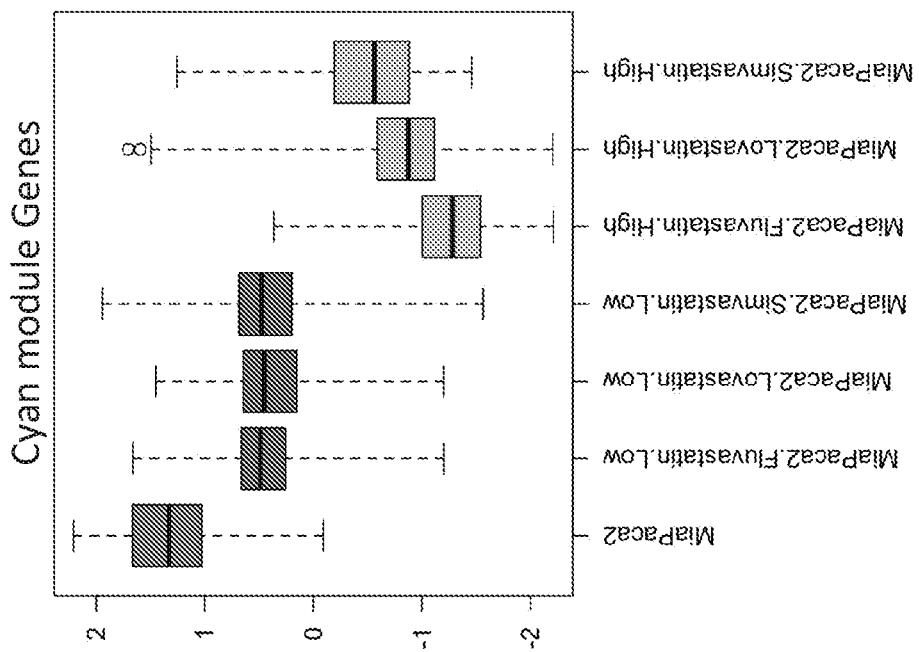
Figure 39:
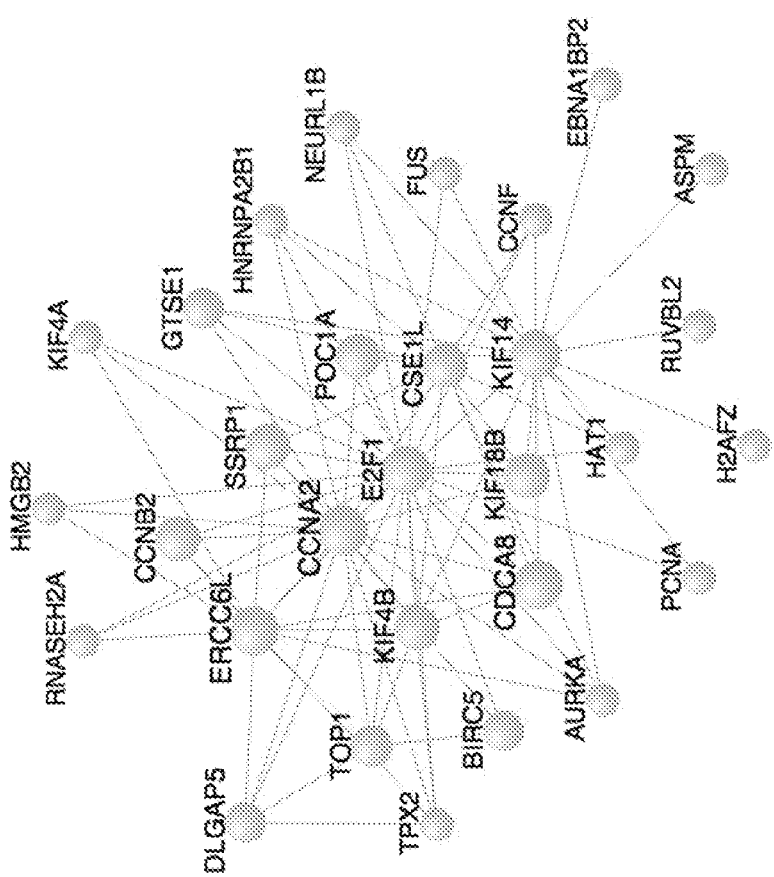
Figure 40:
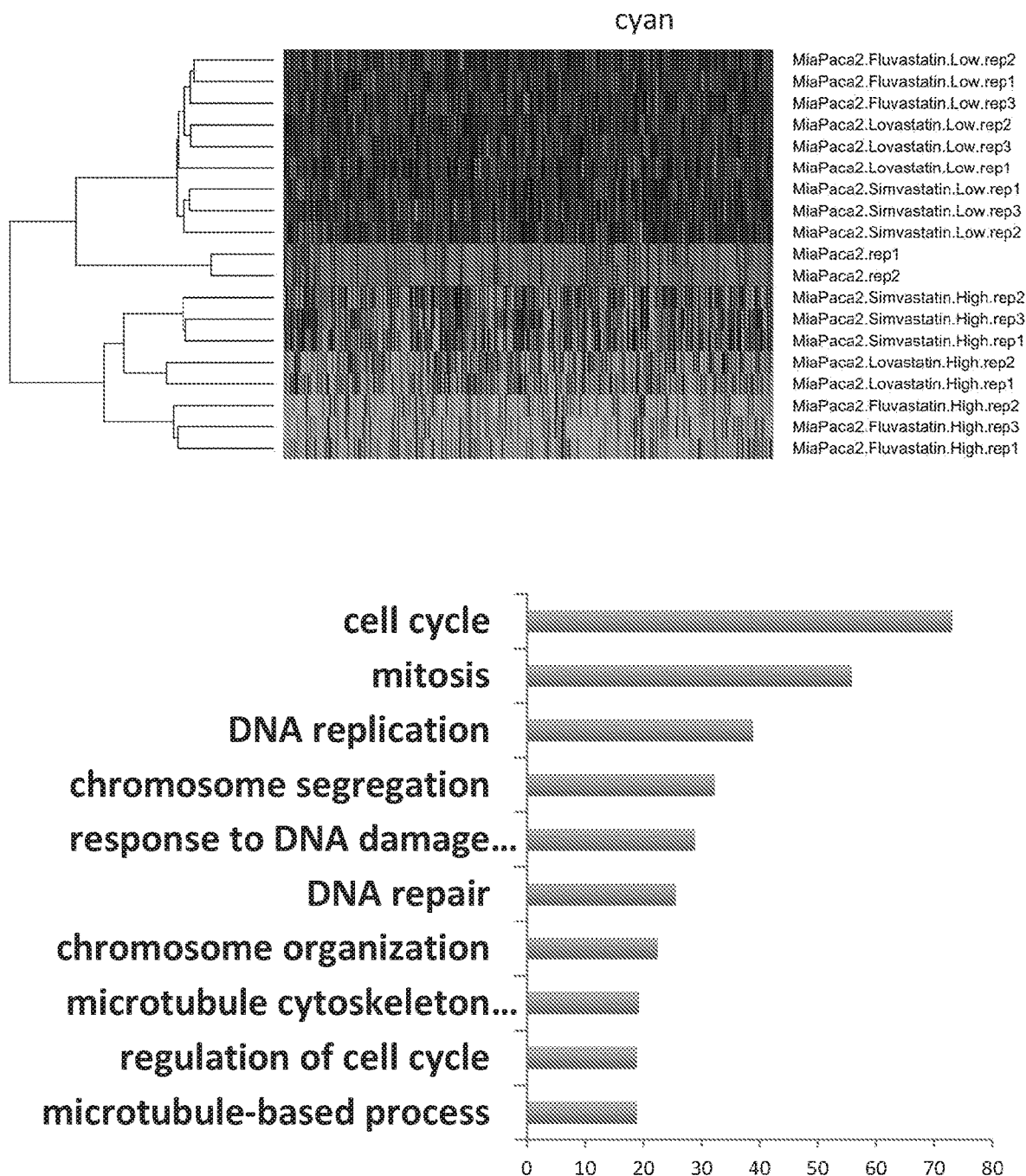
Figure 41:
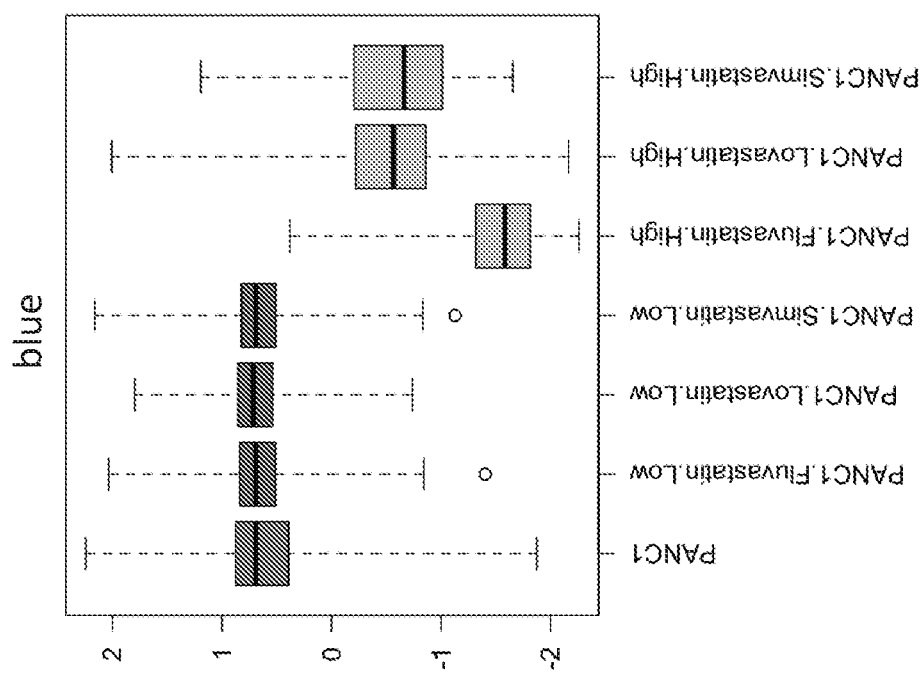
Figure 41:
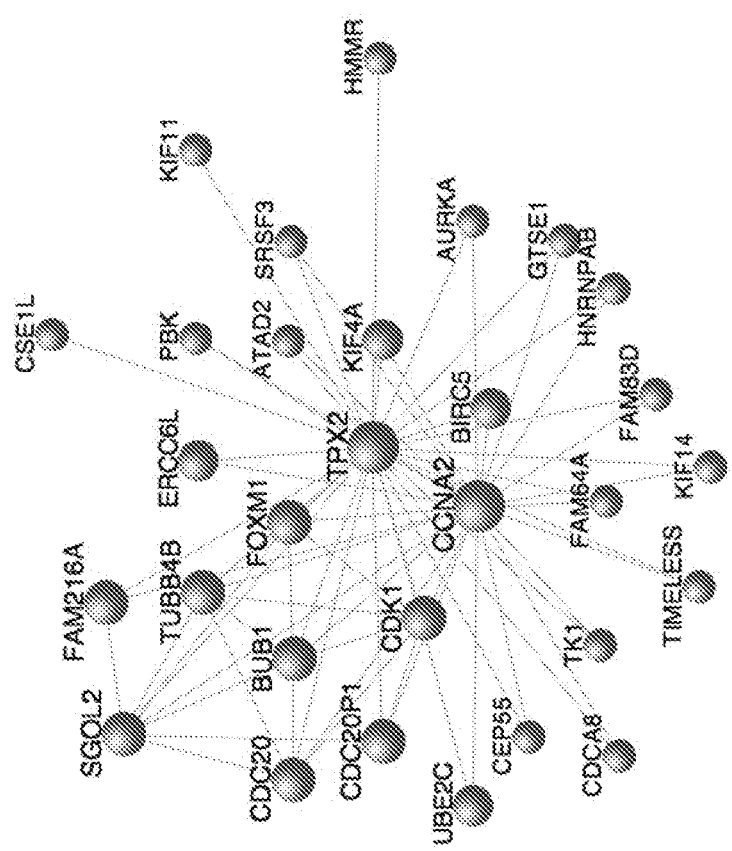
Figure 42:
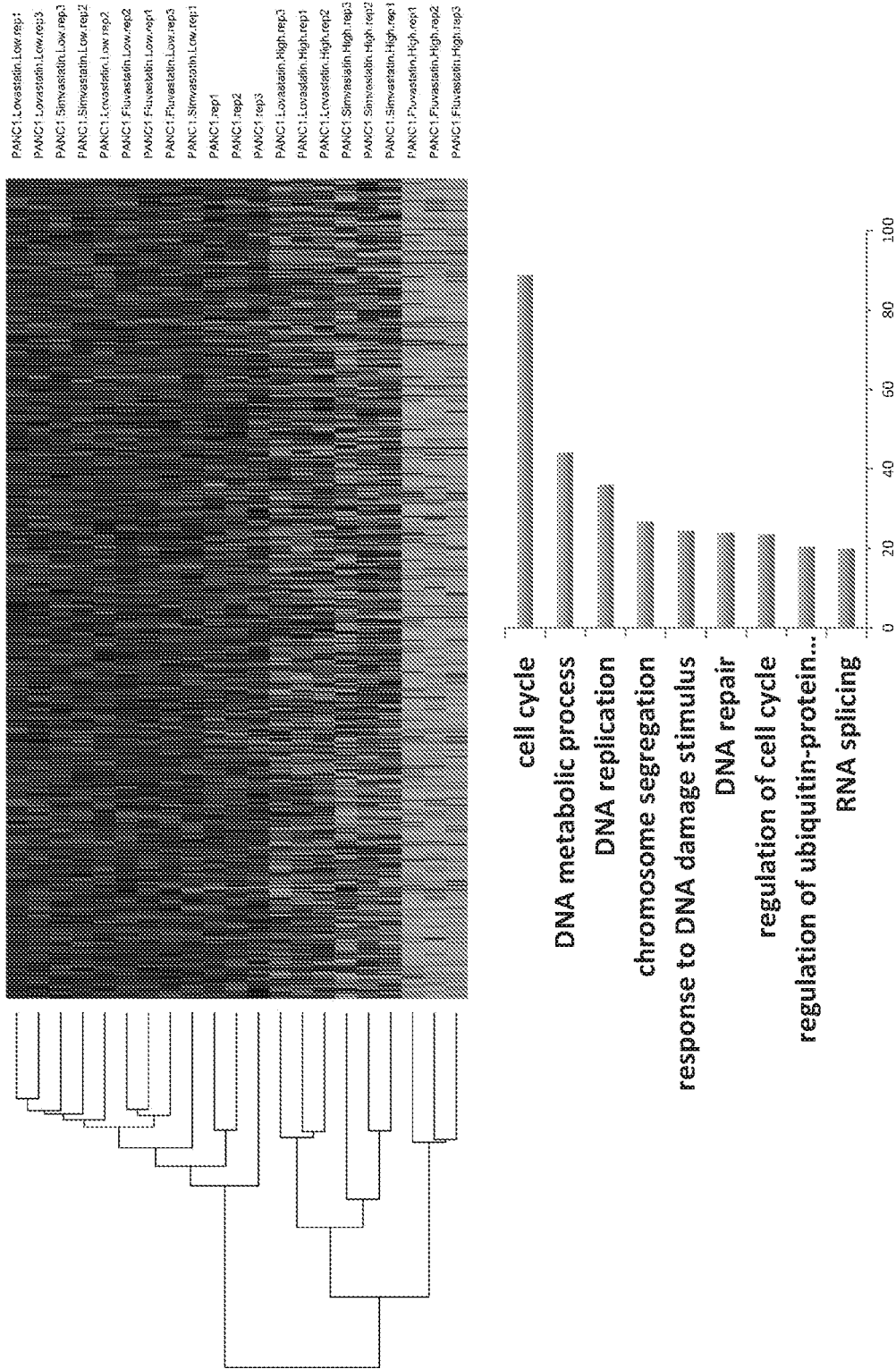
Figure 43:
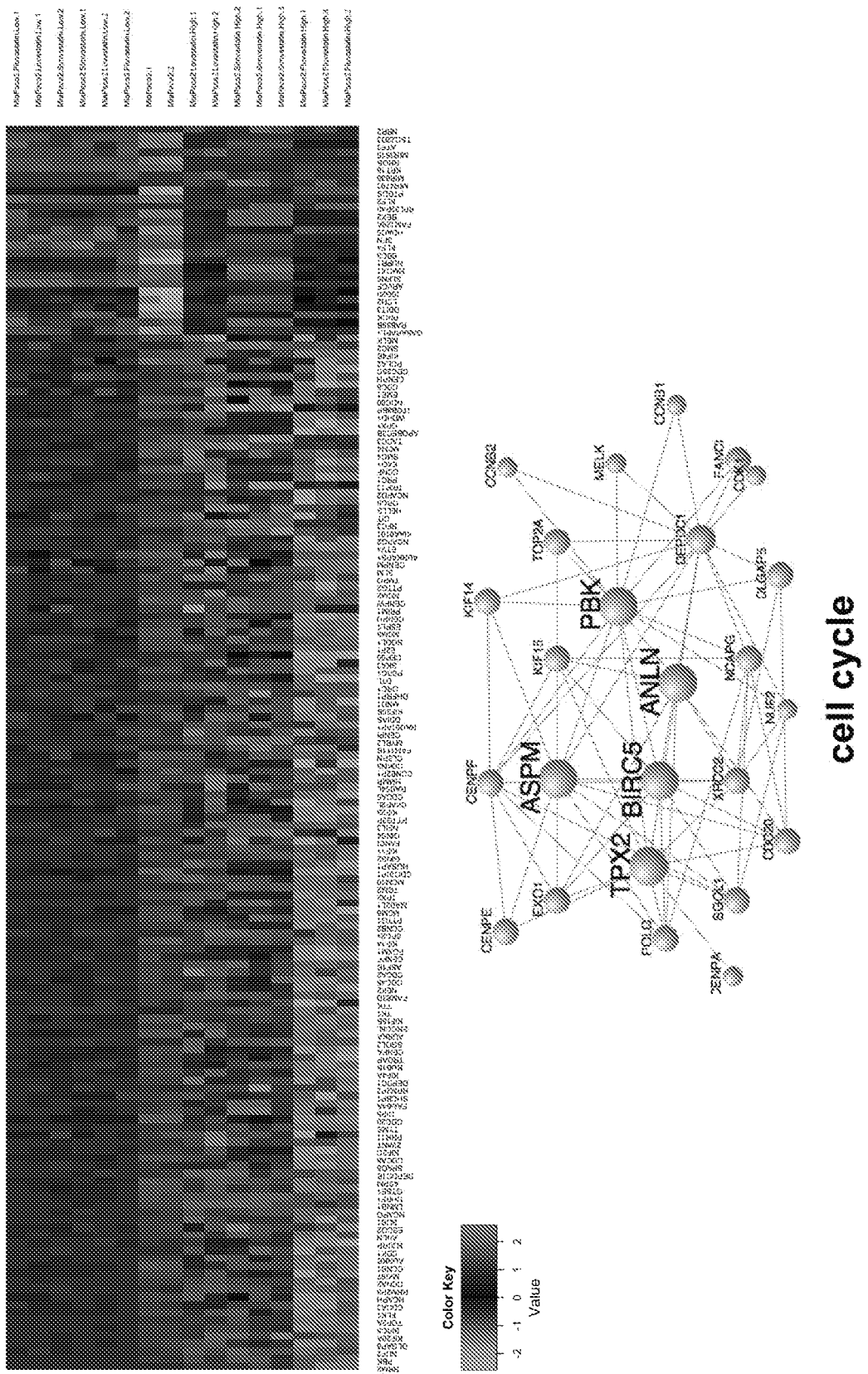
Figure 44:
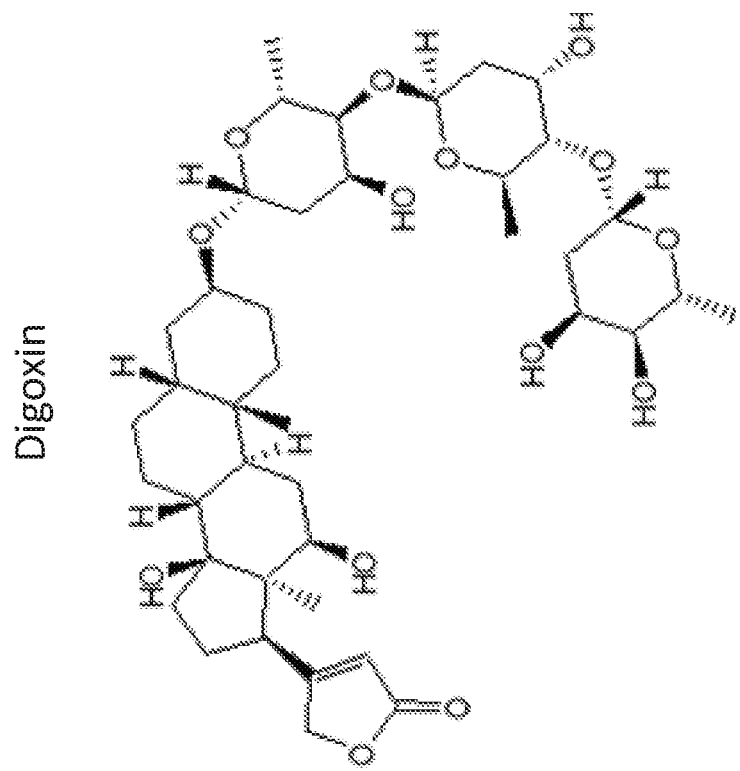
Figure 44:
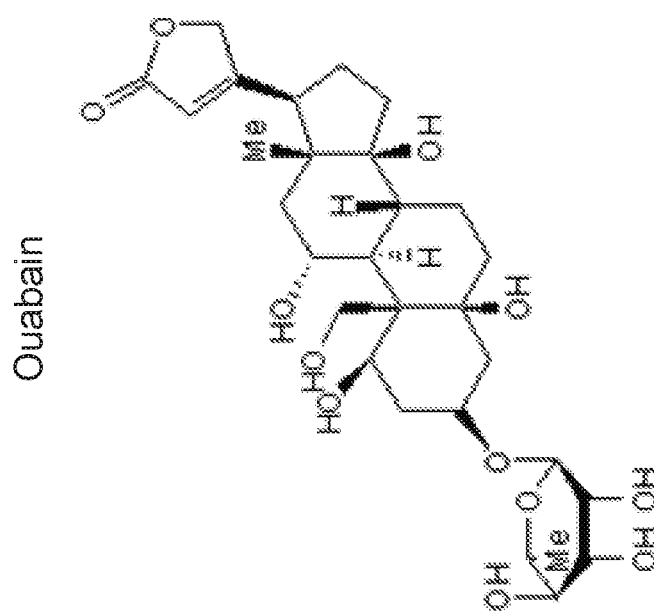
Figure 45:
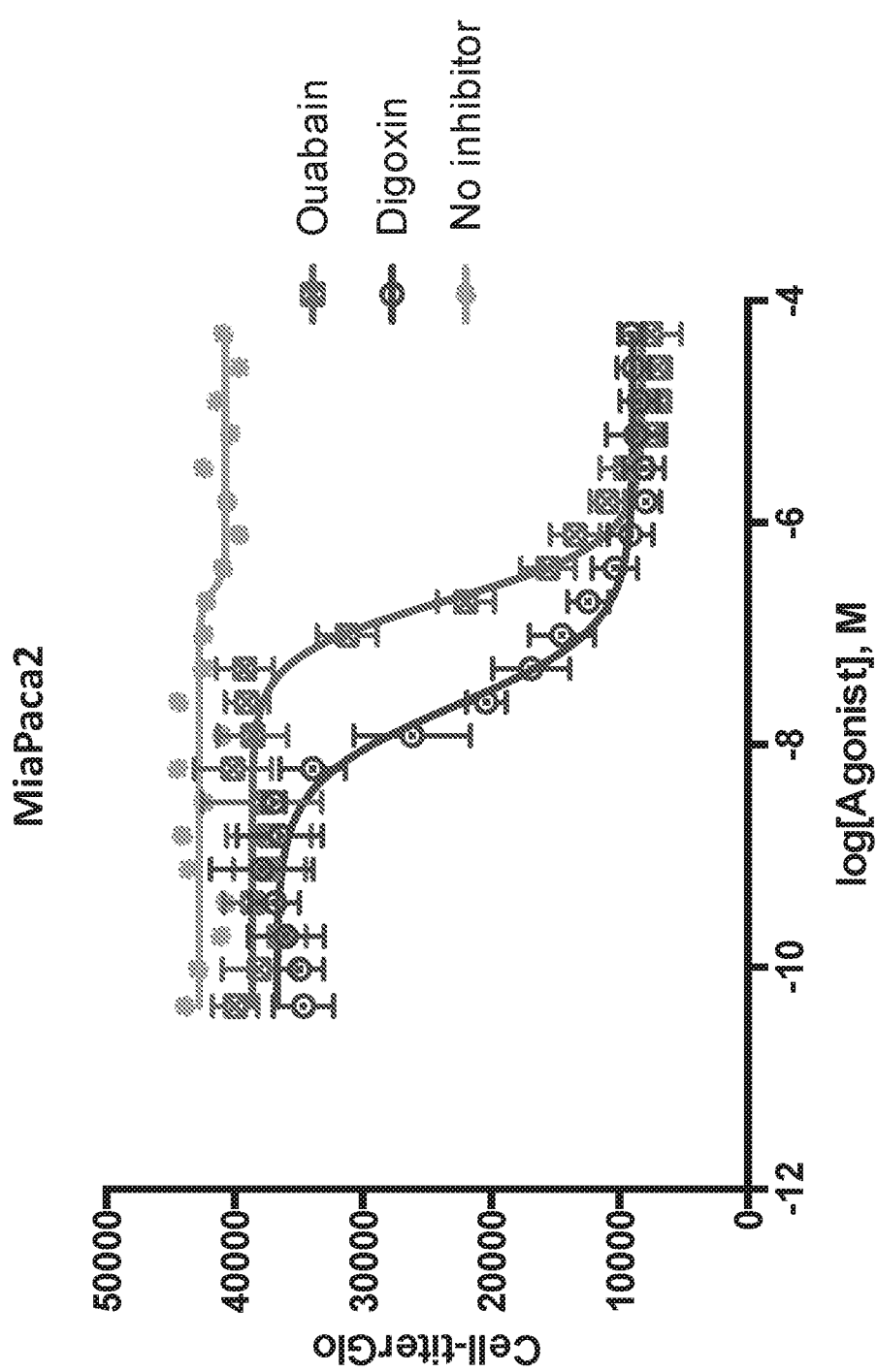
Figure 46:
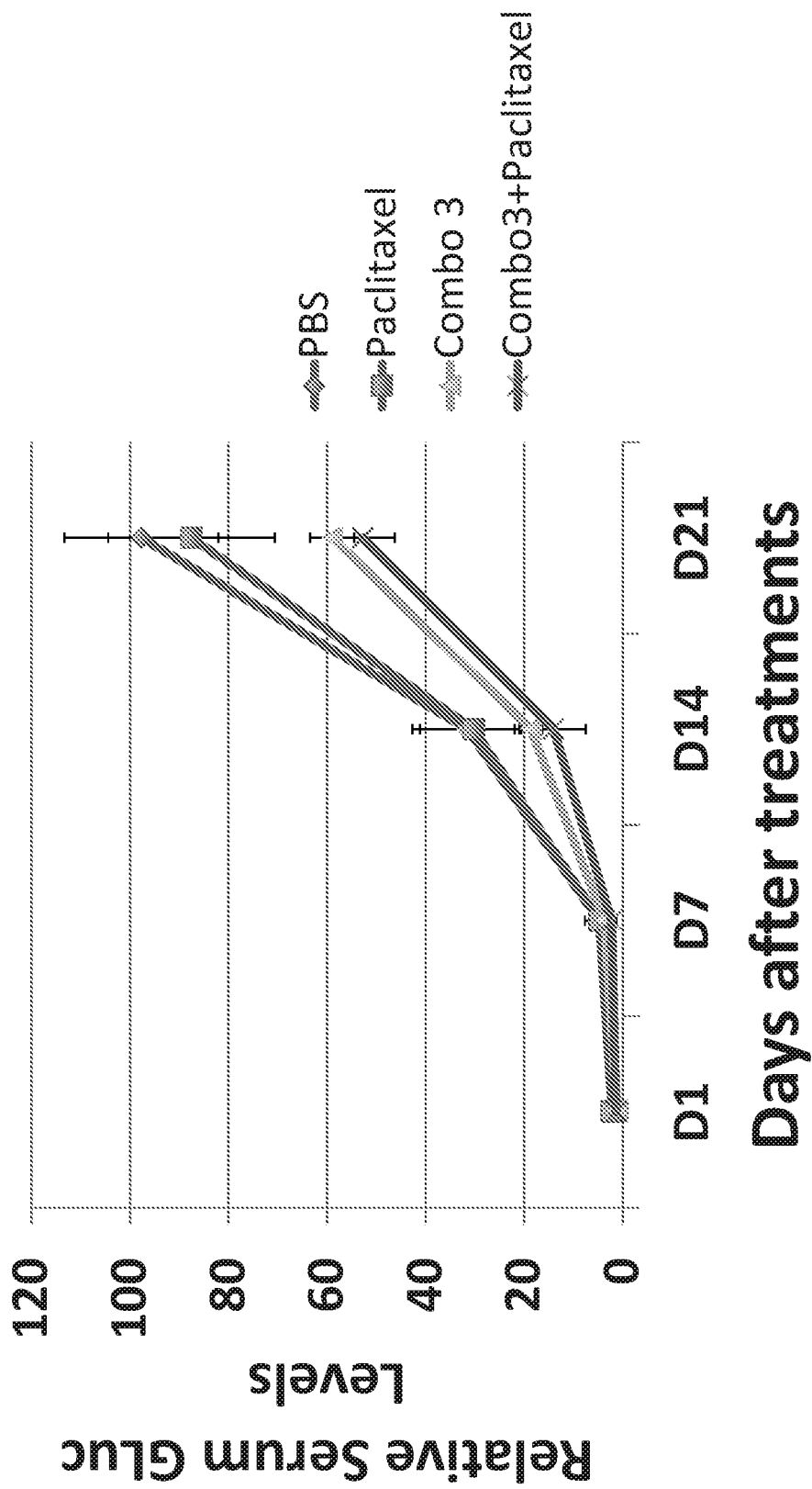
Figure 48:
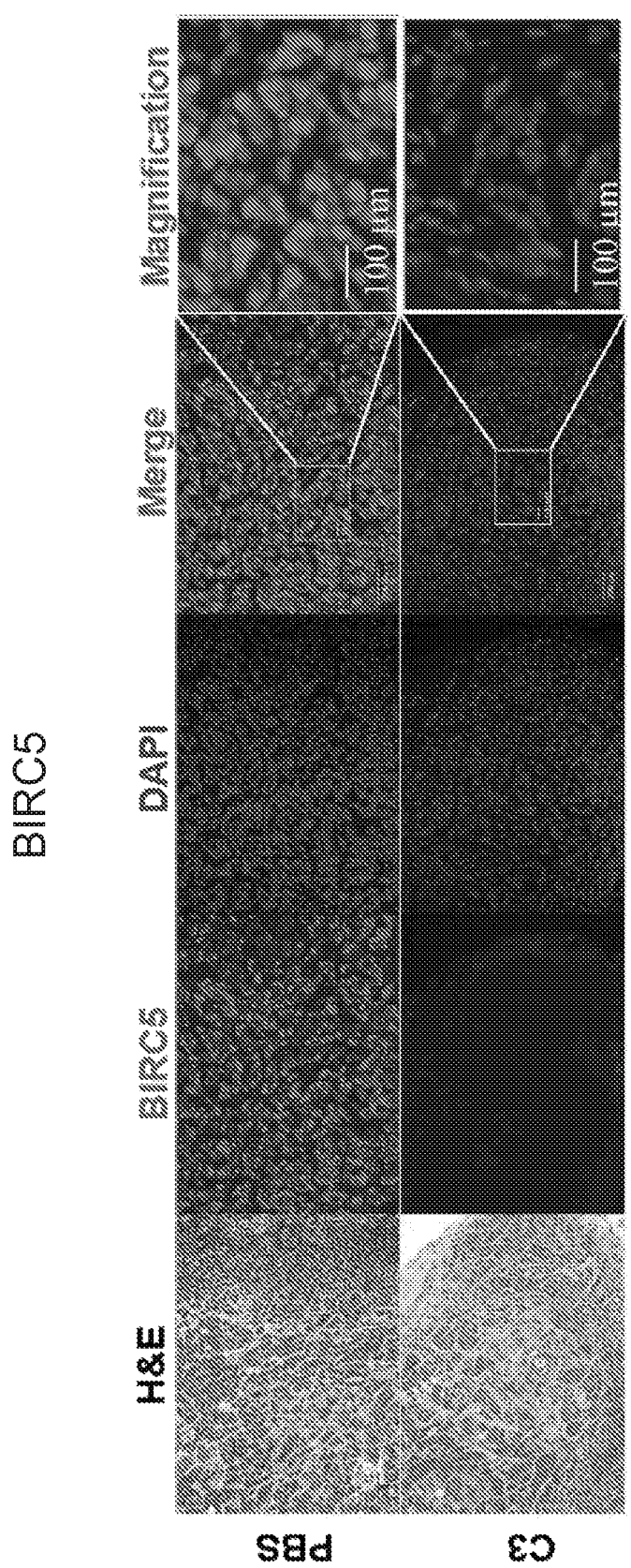
Figure 49:
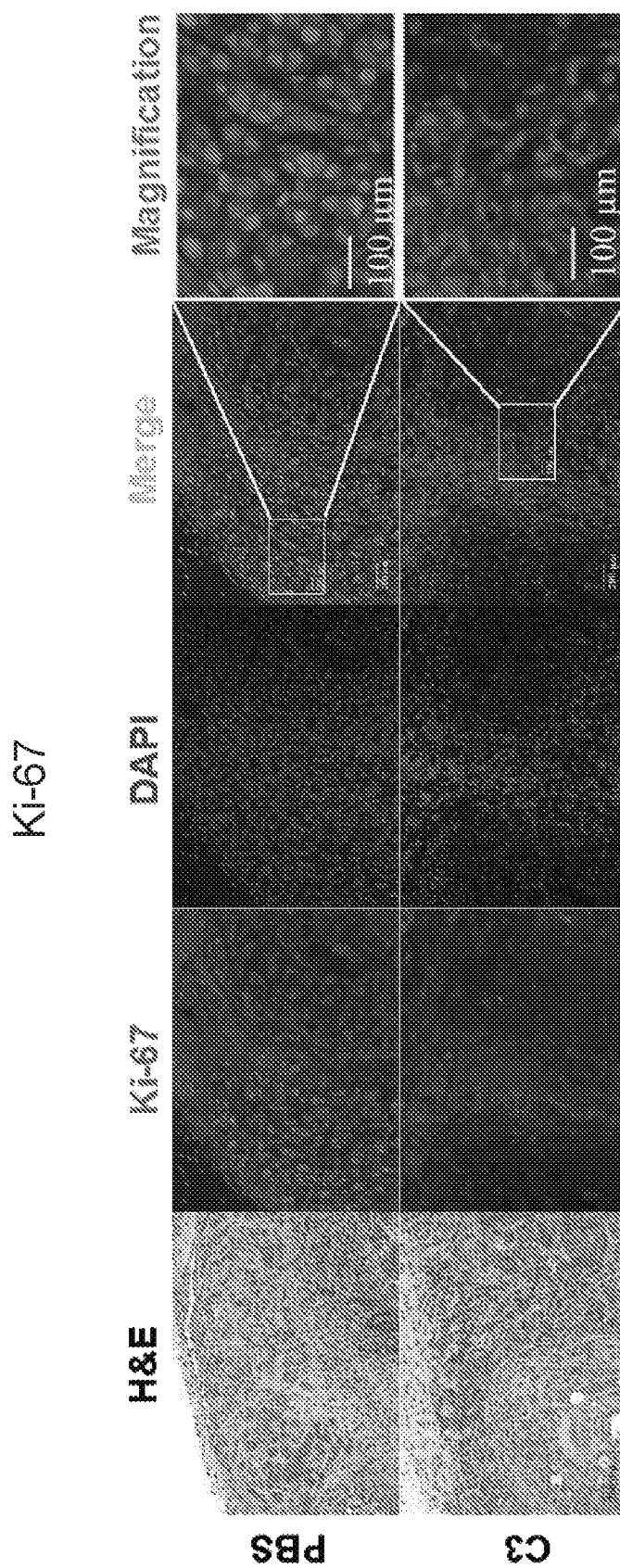

Notably, there is greatest suppression with the triple drug combination of metformin, simvastatin, and digoxin;

FIG. 14 is a graph illustrating that treatment with three different statins (fluvastatin, lovastatin, and simvastatin) suppress patient derived pancreatic cancer cell lines #5 and #15 (PDCL5 and PDCL15) BIRC5 mRNA expression (gene transcription) in vitro, in accordance with one or more embodiments of the invention;

FIG. 15 is a schematic illustrating that BIRC5 (survivin) inhibits apoptosis via inhibition of Caspase-9 and effector caspases. SMAC (DIABLO) inhibits BIRC5 (survivin);

FIG. 16 is a set of images illustrating how the triple drug combination (C3) acts on BIRC5 and inhibits pancreatic cancer (FIG. 16A: before applying C3; FIG. 16B: after applying C3), in accordance with one or more embodiments of the invention;

FIG. 17 illustrates a Weighted Gene Co-expression Network Analysis (WGCNA) comparison of three control tumors versus three xenograft tumors treated with the triple drug combination (C3) of metformin, simvastatin, and digoxin, in accordance with one or more embodiments of the invention;

FIG. 18 illustrates RNA-sequencing (RNA-Seq) results and a WGCNA gene network module showing that the triple drug combination (C3) of metformin, simvastatin, and digoxin significantly inhibit cell cycle related gene expression, in accordance with one or more embodiments of the invention;

FIG. 19 is a graph illustrating results from real-time PCR showing that the triple drug combination (C3) of metformin, simvastatin, and digoxin significantly inhibits cell cycle related genes BIRC5, TOP2A, and FLNB expression, in accordance with one or more embodiments of the invention;

FIG. 20 illustrates Weighted Gene Co-expression Network Analysis (WGCNA) revealed gene-networked modules correlated with the triple drug combination (C3) for patient derived pancreatic cancer cell line #5 in vitro, in accordance with one or more embodiments of the invention;

FIG. 21 illustrates RNA-sequencing (RNA-Seq) results and a WGCNA gene network module showing that the triple drug combination (C3) of metformin, simvastatin, and digoxin significantly inhibits cell cycle related gene expression, in accordance with one or more embodiments of the invention;

FIG. 22 is a graph illustrating results from real-time PCR showing that the triple drug combination (PDCL5-C3) of metformin, simvastatin, and digoxin significantly inhibits cell cycle related genes BIRC5 and TOP2A expression, in accordance with one or more embodiments of the invention. The control is represented as PDCL5 and the individual drugs simvastatin, metformin, and digoxin are represented as PDCL5-S, PDCL5-M, and PDCL5-D respectively. Notably, there is significantly greater suppression of BIRC5 and TOP2A nRNA expression with the triple drug combination when compared to the individual drugs and control;

FIG. 23 illustrates results from real-time PCR showing that the triple drug combination (C3) of metformin, simvastatin, and digoxin and the individual drug simvastatin significantly inhibit ATP/energy related gene expression in the purple WGCNA gene network module, in accordance with one or more embodiments of the invention. The gene network module shows that SEMA7A and DDX5 are important ATP/energy related genes;

FIG. 24 is a graph illustrating results from real-time PCR showing that the triple drug combination (PDCL5-C3) of metformin, simvastatin, and digoxin and the individual drug simvastatin significantly inhibit ATP/energy related genes DDX5 and SEMA7A expression in patient derived pancreatic cancer cell line #5 in vitro, in accordance with one or more embodiments of the invention. The control is represented as PDCL5 and the individual drugs simvastatin, metformin, and digoxin are represented as PDCL5-S, PDCL5-M, and PDCL5-D respectively;

FIG. 25 illustrates RNA-sequencing (RNA-Seq) results and a WGCNA gene network module showing that the triple drug combination (C3) of metformin, simvastatin, and digoxin significantly increases cell death related gene expression, in accordance with one or more embodiments of the invention. The gene network module shows that DUSP15 and RHOB are important cell death/apoptosis related genes;

FIG. 26 is a graph illustrating results from real-time PCR showing that the triple drug combination (PDCL5-C3) of metformin, simvastatin, and digoxin significantly increases cell death/apoptosis related genes DUSP15 and RHOB, in accordance with one or more embodiments of the invention. The control is represented as PDCL5 and the individual drugs simvastatin, metformin, and digoxin are represented as PDCL5-S, PDCL5-M, and PDCL5-D respectively. The graph clearly shows a synergistic effect of the triple drug combination in comparison to the individual drugs, which do not have an effect on the cell death/apoptosis related genes;

FIG. 27 illustrates the results from using Weighted Gene Co-expression Network Analysis (WGCNA) to analyze mRNA expression from published databases of 9 major cancers in nearly 1000 samples, in accordance with one or more embodiments of the invention;

FIG. 28 illustrates module-trait relationships between different cancers, in accordance with one or more embodiments of the invention;

FIG. 29 is a graph illustrating the mRNA expression of different cell processes, in accordance with one or more embodiments of the invention;

FIG. 30 is a gene network module of actionable genes that are common to all 9 cancers. Notably, BIRC5 is one of these network genes. Also included are fluorescence images of actionable genes TPX2, BIRC5, and CDK1 in control, PanIN, and PDAC cells; in accordance with one or more embodiments of the invention;

FIG. 31 is a graph illustrating the effect of metformin on commercial human pancreas cancer cells (MIA PaCa2 and PANC1), in accordance with one or more embodiments of the invention;

FIG. 32 is a graph illustrating the effect of statins on BIRC5 gene expression, in accordance with one or more embodiments of the invention;

FIG. 33 is a graph illustrating that treatment with individual drugs simvastatin, metformin, and digoxin and various combinations of the individual drugs suppress MIA PaCa2 cell viability, in accordance with one or more embodiments of the invention. Notably, there is greatest suppression with the triple drug combination of metformin, simvastatin, and digoxin;

FIG. 34 is a graph illustrating that treatment with individual drugs simvastatin, metformin, and digoxin and various combinations of the individual drugs suppress AsPC1 cell viability, in accordance with one or more embodiments of the invention. Notably, there is greatest suppression with the triple drug combination of metformin, simvastatin, and digoxin;

FIG. 35 is a graph illustrating that treatment with individual drugs simvastatin, metformin, and digoxin and various combinations of the individual drugs suppress PANC1 cell viability, in accordance with one or more embodiments of the invention. Notably, there is greatest suppression with the triple drug combination of metformin, simvastatin, and digoxin;

FIG. 36 is a graph illustrating that treatment with metformin suppresses pancreatic cancer cell viability, in accordance with one or more embodiments of the invention;

FIG. 37 shows the chemical structures for simvastatin, fluvastatin, and lovastatin;

FIG. 38 is a graph illustrating that treatment with individual statins simvastatin, fluvastatin, and lovastatin suppresses MIA PaCa2 cell viability, in accordance with one or more embodiments of the invention;

FIG. 39 illustrates that statins inhibit gene expression in cyan module in MIA PaCa2 PDAC cells. Genes in the cyan module display dose-dependent response to statins treatment in MIA PaCa2. Genes in cyan module are enriched in cell cycle, in accordance with one or more embodiments of the invention;

FIG. 40 is a heat map of gene expressions using statins of high and low concentrations in MIA PaCa2 cells, in accordance with one or more embodiments of the invention;

FIG. 41 illustrates that the same set of genes were not inhibited by statins at low concentration in PANC1 cells. Genes in the blue module in PANC1 are enriched in cell cycle. High doses of statins significantly suppress blue module gens, including BIRC5, in accordance with one or more embodiments of the invention;

FIG. 42 is a heat map of gene expressions using statins of high and low concentrations in PANC1 cells, in accordance with one or more embodiments of the invention;

FIG. 43 is a heat map illustrating that statins inhibit cell cycle genes in PDAC cells, in accordance with one or more embodiments of the invention;

FIG. 44 shows the chemical structures for ouabain and digoxin;

FIG. 45 is a graph illustrating that treatment with individual drugs ouabain and digoxin suppresses MIA PaCa2 cell viability, in accordance with one or more embodiments of the invention;

FIG. 46 is a graph illustrating in vivo response to the triple drug combination (Combo 3) of metformin, simvastatin, and digoxin with and without paclitaxel, in accordance with one or more embodiments of the invention;

FIG. 47 is a set of images comparing tumor immunofluorescence of patient derived pancreatic cancer tumors with and without the triple drug combination (C3) of metformin, simvastatin, and digoxin, in accordance with one or more embodiments of the invention. Notably, BIRC5 expression is greatly suppressed with the triple drug combination (C3) when compared to phosphate buffered saline (PBS);

FIG. 48 is a set of images comparing tumor immunofluorescence of patient derived pancreatic cancer tumors with and without the triple drug combination (C3) of metformin, simvastatin, and digoxin, in accordance with one or more embodiments of the invention. Ki-67 is a general biomarker for cancer proliferation. Notably, Ki-67 expression is greatly suppressed with the triple drug combination (C3) when compared to phosphate buffered saline (PBS);

FIG. 49 is a set of images comparing tumor immunofluorescence of patient derived pancreatic cancer tumors with and without the triple drug combination (C3) of metformin, simvastatin, and digoxin, in accordance with one or more embodiments of the invention.

DETAILED DESCRIPTION OF THE INVENTION

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. All publications, patents, and patent applications cited herein are hereby incorporated by reference in their entirety for all purposes. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

As disclosed in detail below, it has been discovered that a combination of the three well-known and FDA approved drugs, metformin, simvastatin, and digoxin, can inhibit human pancreatic cancer cell growth both in vitro and in vivo. To obtain insight on the mechanisms of this triple drug combination's function on pancreatic cancer and the molecular target of each individual drug and the triple drug combination, RNA-Seq coupled with weighted gene co-expression network analysis (WGCNA) was performed on patient derived pancreatic cancer cells that were treated in vitro with the triple drug combination and each individual drug. RNA-Seq data analysis indicated that the triple drug combination inhibits cancer cell growth by decreasing the expression of a network of cell cycle related genes (in particular BIRC5, CCNB1, and TOP2A) and energy metabolism genes (in particular DDX5), as well as promoting the expression of apoptosis related genes (in particular DUSP15 and RHOB).

The data presented herein indicates that simvastatin significantly suppresses expression of cell proliferation and energy metabolism genes, providing evidence that simvastatin plays a primary role in the triple drug combination for inhibiting pancreatic cancer growth by inhibiting genes involving cell proliferation and energy metabolism. Metformin has been shown to stop cancer cell growth by AMPK dependent pathway. Digoxin's mechanism of anticancer action is via inhibition of Na+/K+– ATPase pump, resulting in increased intracellular calcium via increased Na+/Ca2+ pump activity with subsequent induction of apoptosis in cancer cells. Remarkably, the triple drug combination significantly increased the expression of pancreatic cancer cell apoptosis genes, which did not occur in cells treated with the individual drugs, providing evidence that the three drugs act synergistically to activate an apoptosis gene network. Significantly, Simvastatin, Digoxin and Metformin are identified by the World Health Organization as essential medicines, medicines which are considered among the most safe and effective medicines for treating patients.

RNA-Seq coupled with weighted gene co-expression network analysis (WGCNA) was also performed on the triple drug combination treatment against patient derived pancreatic cancer cell tumors in vivo in xenograft mice. The triple drug combination was shown to significantly reduce tumor size compared to controls and nearly completely ablated tumor growth over 4 weeks. Immunohistochemistry of the treated tumors revealed significant suppression of target proteins BIRC5 and Ki-67. WGCNA confirmed that the triple drug combination inhibits a network of cancer cell proliferation genes (in particular BIRC5 and TOP2A).

The data presented herein show that a triple drug combination comprising metformin or a metformin analog, a statin such as simvastatin, and a cardiac glycoside such as digoxin can inhibit pancreatic cancer growth by inhibiting genes involving cell proliferation and energy metabolism, and the predominant drug in these effects are the statins. Without being bound by a specific theory or mechanism of action, the data presented herein provides evidence that this triple drug combination acts to cause cancer cell death via promotion of apoptosis genes via synergistic effects of the three drugs. Experimental data further demonstrates that the triple drug combination inhibits a network of cancer cell proliferation genes, in particular BIRC5.

The invention disclosed herein has a number of embodiments. In one embodiment of the invention, a composition of matter is provided comprising a combination of metformin or metformin analog, a statin, and a cardiac glycoside. In the typical working embodiments of the invention that are disclosed herein, this composition of matter comprises a combination of metformin, simvastatin, and digoxin. Metformin, simvastatin, and digoxin are all therapeutic compounds that have been approved by the U.S. Food and Drug Administration (FDA). Metformin is typically administered for the treatment of type 2 diabetes. Simvastatin is typically administered for the treatment of elevated lipid levels (e.g. low-density lipoprotein, triglycerides) and to lower the risk of stroke, heart attack, and other heart complications. Digoxin is typically administered for the treatment of heart failure and atrial fibrillation. Unexpectedly, a composition comprising the combination of these three therapeutic compounds provides an effective adjuvant therapy for pancreatic cancer. As shown for example in FIG. 26, the combination of these three therapeutic compounds (i.e. triple drug combination) has a synergistic effect in inhibiting/suppressing the growth of a pancreatic cancer cell. The composition may also be used as part of a therapy for other diseases or conditions of the pancreas such as pancreatitis. The therapeutic compounds of the composition (i.e. active ingredients) may be administered for therapy to an animal e.g. a mammal including a human in a conventional manner.

Embodiments of the invention include compositions of matter comprising at least two of the following three therapeutic agents: a biguanide such as metformin (or metformin analog), a statin, and a cardiac glycoside. Optionally this composition can include one or more additional agents such as another therapeutic agent approved for the treatment of pancreatic cancer. Additional agents can also include other therapeutic agent approved for other uses, for example a drug identified in Tables 5A-5C below, or a sulfonylurea such as acetohexamide, carbutamide, chlorpropamide, glycyclamide (tolhexamide), metahexamide, tolazamide tolbutamide, glibenclamide (glyburide), glibornuride, gliclazide, glipizide, gliquidone, glisoxepide, glyclopyramide and glimepiride. Embodiments of the invention include those where the dosages of such therapeutic agents are within the range approved for use of that agent in humans by the Food and Drug Administration (as found, for example in databases such as "Drugs@FDA: FDA Approved Drug Products"). In one illustrative embodiment of this composition, the composition is in the form of a pill or tablet (including a plurality of pills or tablets) or the like and comprises a daily (or weekly or monthly) dose of those agents that is within the ranges approved for use of those agents in humans by the Food and Drug Administration.

While simvastatin, metformin and digoxin are illustrative working embodiments in this disclosure, it is to be noted that metformin, simvastatin, and digoxin may be substituted with other metformin analogs, statins, and cardiac glycosides, respectively, in one or more embodiments of the invention. Statins such as simvastatin are HMG-CoA reductase inhibitors. Data from studies with statins that is presented herein provide evidence that HMG-CoA reductase inhibitors are useful in embodiments of the invention. Illustrative statins useful in embodiments of the invention include Lipitor (atorvastatin), Lescol (fluvastatin), Mevacor (lovastatin), Altoprev (lovastatin extended-release), Livalo (pitavastatin), Pravachol (pravastatin), Crestor (rosuvastatin), and Zocor (simvastatin), cerivastatin and mevastatin (see also, e.g. FIG. 14).

Metformin is a first-line medication for the treatment of type 2 diabetes, particularly in people who are overweight. Metformin is also used in the treatment of polycystic ovary syndrome. Illustrative metformin analogs include the analogs as described in Pietras et al. (PCT Application No. PCT/US2013/045250). Digoxin is in the cardiac glycoside family of medications. Data from studies with digoxin that is presented herein provide evidence that cardiac glycosides are useful in embodiments of the invention. Cardiac glycosides are a class of organic compounds that affect the inotropic and chronotropic activity of the heart by acting on the sodium-potassium ATPase pump. These cardiac glycosides are Na+/K+ ATPase inhibitors that act via the Warburg effect. Bufalin, ouabain and digoxin are a few illustrative cardiac glycosides. Digitalis is another commonly used cardiac glycoside. Digoxin preparations are marketed under the trade names Cardigox; Cardiogoxin; Cardioxin; Cardoxin; Coragoxine; Digacin; Digicor; Digomal; Digon; Digosin; Digoxine Navtivelle; Digoxina-Sandoz; Digoxin-Sandoz; Digoxin-Zori; Dilanacin; Eudigox; Fargoxin; Grexin; Lanacordin; Lanacrist; Lanicor; Lanikor; Lanorale; Lanoxicaps; Lanoxin; Lanoxin PG; Lenoxicaps; Lenoxin; Lifusin; Mapluxin; Natigoxin; Novodigal; Purgoxin; Sigmaxin; Sigmaxin-PG; Toloxin. Using experimental studies such as those disclosed herein, we have identified a number cardiac glycosides that inhibit BIRC5 expression in pancreatic cancer (as well as similarly regulated genes). These cardiac glycosides include digoxin, digitoxigen, digoxigen, digitalis, lanatoside C, bufalin and oubain.

Typically, the compositions of the invention are used to modulate the growth of pancreatic cancer cells that express BIRC5 protein/mRNA. Pancreatic cancers or neoplasms of the pancreas include neoplasms of the endocrine pancreas and neoplasms of the exocrine pancreas such as adenocarcinomas, acinar cell carcinomas, adenosquamous carcinomas, colloid carcinomas, hepatoid carcinomas, intraductal papillary mucinous neoplasms, mucinous cystic neoplasms, pancreatic intraepithelial neoplasia, pancreatoblastomas, serous cystadenomas, signet ring cell carcinoma, solid-pseudopapillary neoplasm, undifferentiated carcinomas, and undifferentiated carcinoma with osteoclast-like giant cells. In one or more embodiments of the invention, the composition is used to inhibit the growth of a pancreatic ductal adenocarcinoma (PDAC). In certain embodiments of the invention, the composition comprises these three agents in combination with a pancreatic ductal adenocarcinoma cell.

In typical embodiments of the invention, the composition comprises amounts of metformin, simvastatin, and digoxin sufficient to inhibit/suppress in vivo growth of a pancreatic cancer cell when administered to a patient diagnosed with pancreatic cancer. In one embodiment, the composition comprises amounts of metformin, simvastatin, and digoxin sufficient to inhibit/suppress in vivo growth of a human pancreatic ductal adenocarcinoma cell when orally administered to a patient diagnosed with pancreatic ductal adenocarcinoma. Typically, the composition comprises 5-80 milligrams po of simvastatin; 500-2550 milligrams po of metformin; and 0.125-0.250 milligrams po of digoxin. In some embodiments, the composition can comprise from 62.5 micrograms to 500 micrograms po of digoxin. The composition of matter typically further comprises a pharmaceutically acceptable carrier. In one or more embodiments, the composition is formed as a time release formulation and may be disposed in a capsule or tablet.

The fact that statins, metformin and digoxin are all well-known drugs that have been used in patients for years to treat other syndromes/diseases allows information from both current and previous studies on the dose and efficacy of these agents to be used to identify doses for use the triple drug therapies disclosed herein (e.g. as a treatment for pancreatic cancer). See e.g. Zhou, G., et al. (2015). Metformin Restrains Pancreatic Duodenal Homeobox-1 (PDX-1) Function by Inhibiting ERK Signaling in Pancreatic Ductal Adenocarcinoma. *Current molecular medicine*, 16(1), 83-90; and Elbaz, H. A., et al. (2012). Digitoxin and its analogs as novel cancer therapeutics. *Experimental Hematology & Oncology*, 1(4). For example, in embodiments of the invention, the in vivo dose of simvastatin can be approximately 20 mg/kg (e.g. from 10 mg/kg to 30 mg/kg), the in vivo dose of digoxin can be approximately 2 mg/kg (e.g. from 1 mg/kg to 3 mg/kg), and the in vivo dose of metformin can be approximately 100 mg/kg (e.g. from 50 mg/kg to 150 mg/kg). In embodiments of the invention, the human clinical dose of simvastatin can be ~80 mg/day orally, so the human dose in this embodiment of the invention is ~1.14 mg/kg. In embodiments of the invention, the level of digoxin for treatment is typically 0.5-2 ng/mL. Since this is a narrow therapeutic index, it is therefore important that digoxin concentration be maintained in approximately this range if it is used in patients with other conditions such as heart failure.

While it is possible for the combination of active ingredients of the composition to be administered without other ingredients, it is preferable to present them within a pharmaceutical formulation. Pharmaceutical formulations according to the present invention comprise the active ingredients (i.e. metformin, simvastatin, and digoxin) together with one or more pharmaceutically acceptable carriers or excipients and optionally other therapeutic agents. The pharmaceutically acceptable carrier(s) cannot be water alone and must be acceptable in the sense of being compatible with the other ingredients of the formula. In embodiments of the invention, the composition comprises a pharmaceutically acceptable carrier selected to be compatible with metformin and compatible simvastatin, and compatible digoxin when all three are combined in a single composition.

Illustrative formulations include those suitable for oral, enteral, topical (including transdermal, buccal and sublingual) or parenteral (including subcutaneous, intramuscular, intravenous, and intradermal) administration. The formulations may be prepared by any methods well known in the art of pharmacy, for example, using methods such as those described in Remington: The Science and Practice of Pharmacy (22nd ed., Pharmaceutical Press, 2012, see especially Section 5: Pharmaceutical Dosage Forms: Manufacturing and Compounding). Such methods include the step of bringing into association the active ingredient with the carrier which constitutes one or more accessory ingredients. Such accessory ingredients may include pharmaceutically acceptable auxiliary substances as required to, for example, stabilize the formulation and/or approximate physiological conditions. Illustrative agents include those conventional in the art, such as agents that inhibit microbial growth, pH adjusting and buffering agents, tonicity adjusting agents, wetting agents, detergents and the like, as well as fillers, binders, diluents, disintegrants, lubricants, colorants, flavoring agents and the like.

Formulations suitable for oral administration may be presented as discrete units such as pills, tablets or capsules each containing a predetermined amount of the active ingredients; as a powder or granules; as a solution or suspension. The active ingredients may also be present as a bolus or paste, or may be contained within liposomes. For parenteral administration, suitable formulations include aqueous and non-aqueous sterile injection. The formulations may be presented in unit-dose or multi-dose containers, for example, sealed vials and ampoules, and may be stored in a freeze dried (lyophilized) condition requiring only the addition of the sterile liquid carrier, for example, water prior to use.

In addition to the triple drug combination of metformin, simvastatin, and digoxin, the composition/methods may further include therapeutic compounds/regimens commonly used in first-line and/or second-line treatments for pancreatic cancer. In one or more embodiments, the composition further includes a gemcitabine (gemzar), 5-fluorouracil (5-FU), irinotecan (camptosar), oxaliplatin (eloxatin), albumin-bound paclitaxel (abraxane), capecitabine (xeloda), cisplatin, paclitaxel (taxol), docetaxel (taxotere), irinotecan liposome (onivyde), or combinations thereof, including FOLFOX (folinic acid, fluorouracil, oxaliplatin) and FOLFIRINOX (folinic acid, fluorouracil, irinotecan, oxaliplatin).

In addition to using them in therapeutic regimens designed to treat pancreatic cancer, the triple drug combinations disclosed herein are useful in a number of other contexts, for example in in vitro assays that are useful for examining cellular growth and differentiation. For example, BIRC5/Survivin is a member of the inhibitor of apoptosis (IAP) family and the survivin protein functions to inhibit caspase activation, thereby leading to negative regulation of apoptosis or programmed cell death. The BIRC5 protein is expressed highly in most human tumors and fetal tissue, but is absent in terminally differentiated cells. In this context, by targeting BIRC5, the triple drug compositions of the invention is useful in assays designed to characterize the state of differentiation of cells, for example an assay which combines a triple drug composition with a population of cells having an unknown differentiation state and then observing the level of growth inhibition caused by this combination. In one illustrative embodiment of such assays, a population of precancerous of cancerous or cancerous cells (e.g. cells obtained from a patient biopsy) is combined with the triple drug composition and the level of apoptosis in the presence of the three drugs is then observed in order to obtain information on the differentiation state of these cells.

As shown by the data presented herein (e.g. FIGS. 1, 2 and 26) disruption of the BIRC5 induction pathways leads to an increase in apoptosis and decrease in tumor cell growth. As shown for example in FIG. 26, while simvastatin, metformin and digoxin alone are able to inhibit the growth of pancreatic cancer cells, the specific combination of these three agents has a surprisingly potent effect on cell growth as compared to the individual agents alone. Without being bound by a specific theory or mechanism of action, this data provides evidence that these agents each target different aspects of the BIRC5 pathway and that the triple drug combination produces a synergistic inhibition of growth in these tumor cells.

Yet another embodiment of the invention is a method of inhibiting growth of a population of cells that express BIRC5 protein (SEQ ID NO: 1). The method comprises combining the population of cells such as pancreatic cancer cells with amounts of metformin, simvastatin, and digoxin sufficient to inhibit expression of BIRC5 protein in the population of cells, thereby inhibiting the growth of the population of cells. In specific instances, the pancreatic cancer cells are pancreatic ductal adenocarcinoma cells. In one or more of these embodiments of the invention, the population of cells are combined with metformin, simvastatin, and digoxin in vivo in a patient diagnosed with a disease syndrome such as pancreatic cancer. In some embodiments, the method further comprises combining the population of pancreatic cancer cells with amounts of at least one of a gemcitabine (gemzar), paclitaxel (abraxane), A23187 (calcimycin) or ouabain. Optionally the method further comprises observing the population of cells for evidence of cell growth inhibition or cell death following exposure to the metformin, simvastatin, and digoxin.

A related embodiment of the invention is a method of inhibiting the expression of BIRC5 mRNA (SEQ ID NO: 2) in a population of cells identified as expressing BIRC5 mRNA. An example of this method comprises combining the population of human cells with amounts of metformin, simvastatin, and digoxin sufficient to inhibit the expression of BIRC5 mRNA in the population of human cells. In one or more embodiments, the metformin, simvastatin, and digoxin are combined with a plurality of cells in an amount sufficient to promote apoptosis in the population of human cells. In one embodiment, the population of human cells are combined with metformin, simvastatin and digoxin in vivo. In another embodiment, the population of human cells are combined with metformin, simvastatin and digoxin in vitro. In some embodiments, the method further comprises observing the population of human cells for evidence of cell death. In specific instances, the population of human cells are pancreatic cancer cells.

In certain embodiments, the patient is administered metformin, simvastatin, and digoxin using the composition of matter comprising a combination of metformin, simvastatin, and digoxin, wherein the composition is disposed in a capsule or tablet as a time release formulation. Preferably, the composition is administered to a patient orally. In other embodiments, the composition may be administered through other routes, such as enteral, parenteral, intravenous, and intraperitoneal administrations. In one specific implementation, the composition is given orally once per day indefinitely.

As discussed in detail herein, embodiments of the invention include compositions comprising a combination of a statin such as simvastatin, metformin, and a cardiac glycoside such as digoxin for use as a medicament. One illustrative example of this is a combination of metformin, simvastatin, and digoxin for use in the treatment of a cancer such as a pancreatic ductal adenocarcinoma. A related embodiment is the use of a statin such as simvastatin, metformin, and a cardiac glycoside such as digoxin for the manufacture of a medicament for the treatment of a cancer such as a pancreatic ductal adenocarcinoma.

Suitable dosages, preferably unit dosages, of the composition include the known permissible doses for these compounds separately as described or referred to in reference texts such as the British and US Pharmacopoeias, Remington: The Science and Practice of Pharmacy (Pharmaceutical Press), and Martindale: The Complete Drug Reference (Pharmaceutical Press). The dosages of each particular active agent in any given composition can as required vary within a range of doses known to be required in respect to accepted dosage regimens for that compound. Generally, the therapeutic compounds are administered to the patient in doses that are much lower than their median lethal doses, $LD_{50}$.

In the Examples section below, experiments have been conducted to demonstrate that the compositions of matter described herein and the associated methods of use in inhibiting/suppressing growth of pancreatic cancer cells and in particular, pancreatic ductal adenocarcinoma (PDAC) in clinically relevant models of this pathology. These illustrative experiments show that compositions comprising a combination of metformin, simvastatin, and digoxin suppress the cell viability of both commercial (i.e. MIA PaCa2, PANC1) and patient-derived (i.e. PDCL #5, PDCL #15) human pancreatic cancer cell lines in vitro (see, e.g. FIGS. 3 and 5). Additionally, these illustrative experiments show that the compositions suppress the tumor growth of both commercial (i.e. MIA PaCa2) and patient-derived (i.e. PDCL #5, PDCL #15) human pancreatic cancer cell lines in mice in vivo (see, e.g. FIGS. 1, 2, and 4). Experimental results have indicated that the triple drug combination decreases cell proliferation and energy production while increasing cell death/apoptosis. The unexpected synergistic effect of the triple drug combination in decreasing energy production and increasing cell death is clearly shown for example in FIG. 26. Furthermore, illustrative experiments (see Example 5 below) have found that all 9 major types of cancers (i.e. breast cancer, brain cancer, colon cancer, gastric cancer, liver cancer, lung cancer, pancreatic cancer, renal cancer, prostate cancer) overexpress BIRC5. Thus, the triple drug combination described herein, which suppresses BIRC5 (a target of the three drug therapy), may be used as part of a therapy for all 9 major types of cancers.

It is important to note that both the reproducibility and the clinical translatability of using patient-derived tumor xenograft models have been demonstrated, for example, in Gao et al. (*Nat Med.* 2015, 21(11):1318-25) which identified associations between a genotype and drug response, and established mechanisms of resistance. The findings of Gao et al. provide evidence that clinical trials based on patient-derived tumor xenograft models such as those disclosed herein represent an effective approach for assessing the clinical potential of therapeutic modalities. Thus, the suppression of cell viability and tumor growth of patient derived pancreatic cancer cell lines both in vitro and in vivo in mice provides strong evidence that the compositions disclosed herein will perform similarly in human patients in vivo.

Further aspects and embodiments of the invention are disclosed in the following examples.

EXAMPLES

Example 1: FDA-Approved Drug Combination, Metformin, Simvastatin and Digoxin, Significantly Inhibits Pancreatic Cancer Growth In Vitro and In Vivo Introduction Pancreatic ductal adenocarcinoma (PDAC) is one of the most deadly forms of cancer and almost all patients with PDAC succumb to this lethal disease within months of diagnosis. To fight against PDAC, we utilized the concept of an "actionable gene", on which action can be taken to alter disease progression or guide choice of therapy. We have identified actionable gene, BIRC5, for PDAC using microarray data sets and our own RNA-Seq data of PDAC patient specimens. We performed a high-throughput small compound screening utilizing our powerful BIRC5 synthetic promoter and FDA-approved drug libraries and successfully identified three FDA-approved drugs, metformin, simvastatin, and digoxin, that target BIRC5. To further evaluate the effects of the three drugs on PDAC growth, these drugs at optimal doses were applied to human PDAC derived cell lines in vitro and in vivo in human PDAC xenograft mouse models.

Materials and Methods

Human PDAC cell lines, MIA PaCa2 and PANC1, and PDAC patient derived cell lines (PDCL-5 and PDCL-15) were used in the following experiments. CMV-Gluc-2A-TK, was stably expressed in these cell lines to express Gaussia luciferase and thymidine kinase for bioluminescence and PET imaging. Human PDAC cell lines and PDCLs were exposed to metformin (500 µM), simvastatin (4 µM) and digoxin (50 nM), both individually and in combination. Cell proliferation was determined using both CellTiter-Glo™ (Promega) and Gaussia luciferase (GLuc) assays before and after drug treatment. CellTiter-Glo™ Luminescent Cell Viability Assay is used to determine the number of viable cells in culture based on quantitation of the ATP present, an indicator of metabolically active cells. Pierce Gaussia Luciferase Flash Assay Kit (Thermo Fisher) is used for in vitro Gluc assay. A water soluble coelenterazine is used for in vivo assay (NanoLight Technology). RNA Sequencing was used to determine global gene expression patterns of PDCLs and before and after drug treatment. Xenograft mouse models were generated by subcutaneous injection of 2.5M CMV-Gluc-2A-TK stably transfected PDCL-15 or MIA PaCa2 cells in the flank of nude mice. Drugs at optimized doses of metformin (100 mg/kg), simvastatin (20 mg/kg) and digoxin (2 mg/kg) were administered daily via intraperitoneal injection and PBS was used as control for 4 weeks. Tumor volume and blood Gaussia luciferase levels were closely monitored, as well as tumor bioluminescence at the conclusion of the study. Any evidence of toxicity of the drugs to the mice was also monitored.

Results

In vitro Studies: Compared to each individual drug, the combination of metformin (500 µM), simvastatin (4 µM), and digoxin (50 nM) exhibited a significantly greater inhibition of cell proliferation in MIA PaCa2, PANC1 and PDCL-15 and PDCL-5 in both CellTiter-Glo™ and Gaussia luciferase assays (see, e.g. FIGS. 3 and 5). Transcriptome analysis of PDCLs before and after drug treatment by RNA-sequencing showed that the combination of metformin, simvastatin, and digoxin significantly inhibited BIRC5 gene expression and cell cycle related genes.

In vivo Studies: The combination of 3 drugs, metformin, simvastatin, and digoxin, significantly reduced MIA PaCa2 and PDCL-15 xenograft tumor growth in nude mice in 3 and 4 week treated period, respectively (see, e.g. FIGS. 1 and 4). Gaussia luciferase blood levels were significantly reduced in the 3-drug treatment group (C3) compared to controls (ctrl). Bioluminescence imaging revealed significant reduction of tumor volume in the 3-drug treatment group versus controls (see, e.g. FIG. 2). There was no evidence of toxicity in any of the mice.

Conclusion

The triple drug combination (metformin, simvastatin, and digoxin) has been identified using high throughput screening techniques using synthetic promoters to BIRC5, LAMC2, and insulin. The triple drug combination has been shown to suppress growth of human pancreatic cancers in vitro against commercial human pancreatic cancer cell lines in vitro and in vivo in mice, as well as suppression of proliferation in patient derived pancreatic cancer cell lines in vitro.

It has been found that treatment of the triple drug combination on patient-derived pancreatic cancer cell lines and commercial pancreatic cancer cell lines in vitro significantly decreased cell proliferation and increased cell apoptosis. The genes involved in the triple drug combination therapy were analyzed; the genes involving cell cycle, including BIRC5, were inhibited by the triple drug combination treatment. In addition, a set of glycolysis and the TCA cycle genes, including ENO1 and LDHA, were also inhibited in patient-derived pancreatic cancer cell lines and commercial pancreatic cancer cell lines treated with the triple drug combination. These data support that the triple drug combination is acting on the Warburg effect. In analyzing RNA-sequencing data from patient derived pancreatic cancer cell lines and commercial pancreatic cancer cell lines treated with the triple drug combination, it was found that cell cycle related genes were strongly targeted by simvastatin, whereas the inhibitory effect on glycolysis related genes arose from metformin treatment.

Figure 1:
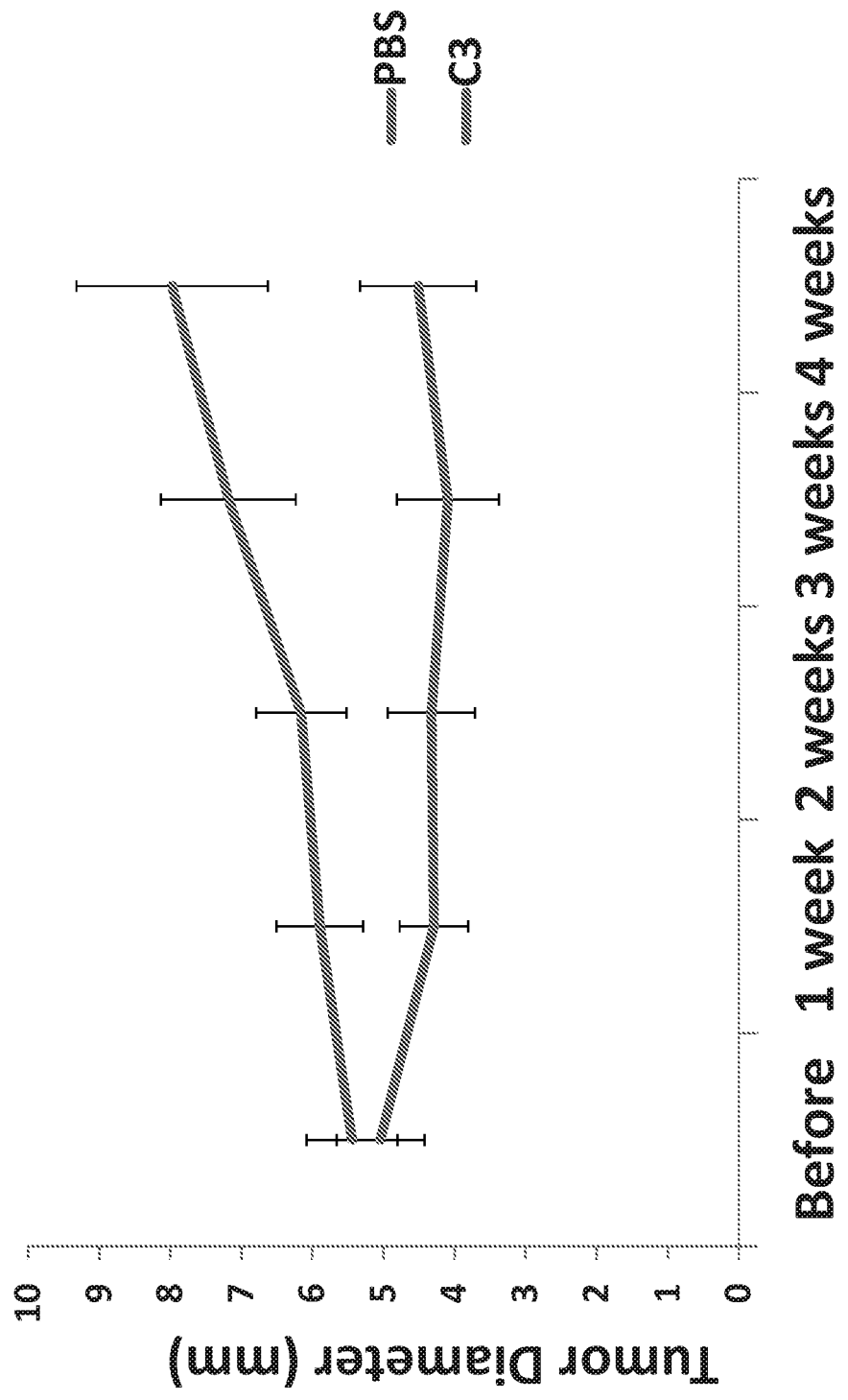
FIG. 1 is a graph illustrating that the tumor growth of patient-derived pancreatic cancer cell line #15 is suppressed by the triple drug combination (C3) of metformin, simvastatin and digoxin when compared to phosphate buffered saline (PBS) in mice, in accordance with one or more embodiments of the invention.
Figure 2:
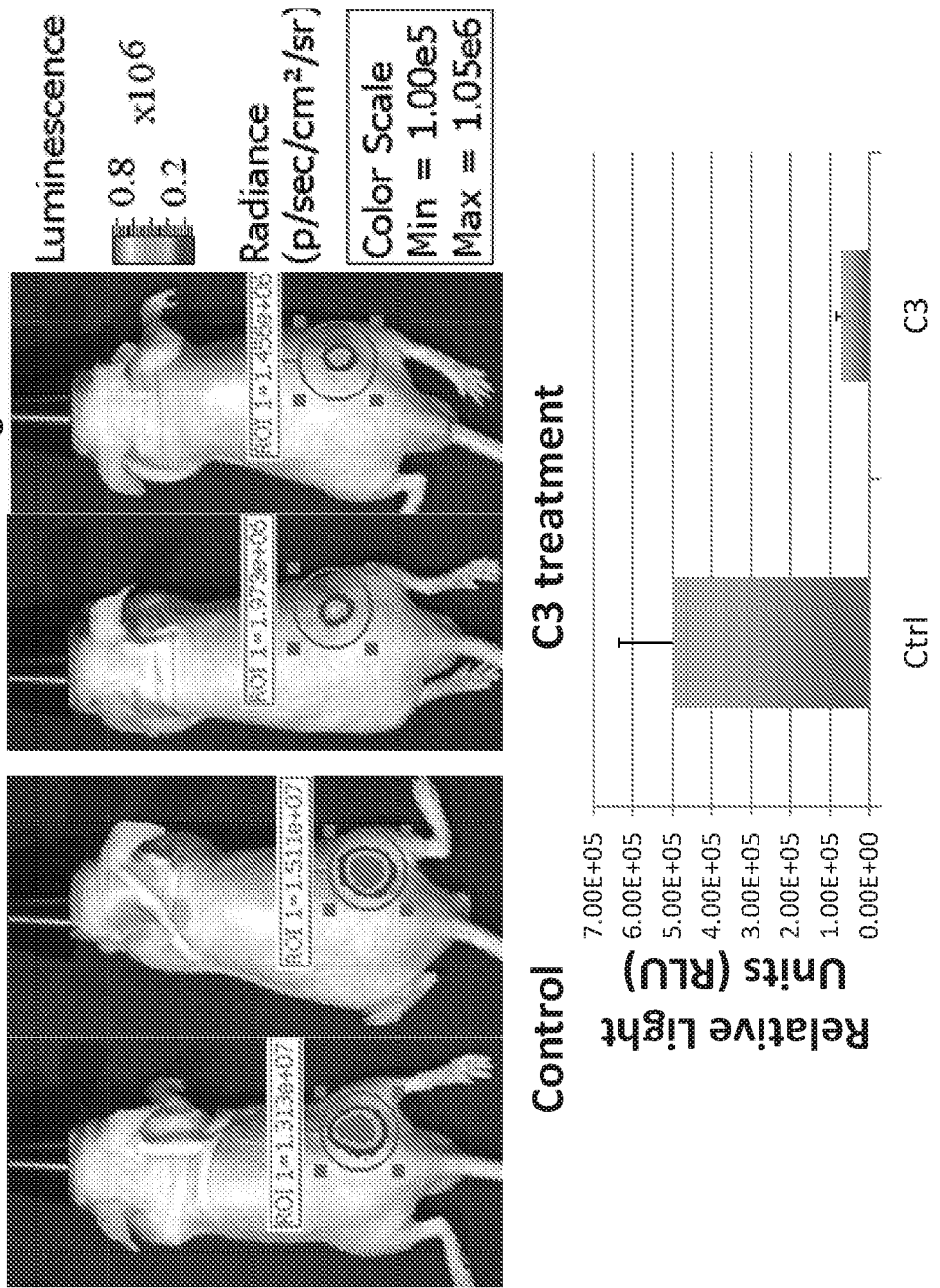
FIG. 2 illustrates that the triple drug combination (C3) treatment suppresses the tumor growth of patient-derived pancreatic cancer cell line #15 in xenograft nude mice, in accordance with one or more embodiments of the invention. The control is represented as Ctrl.
Figure 3:
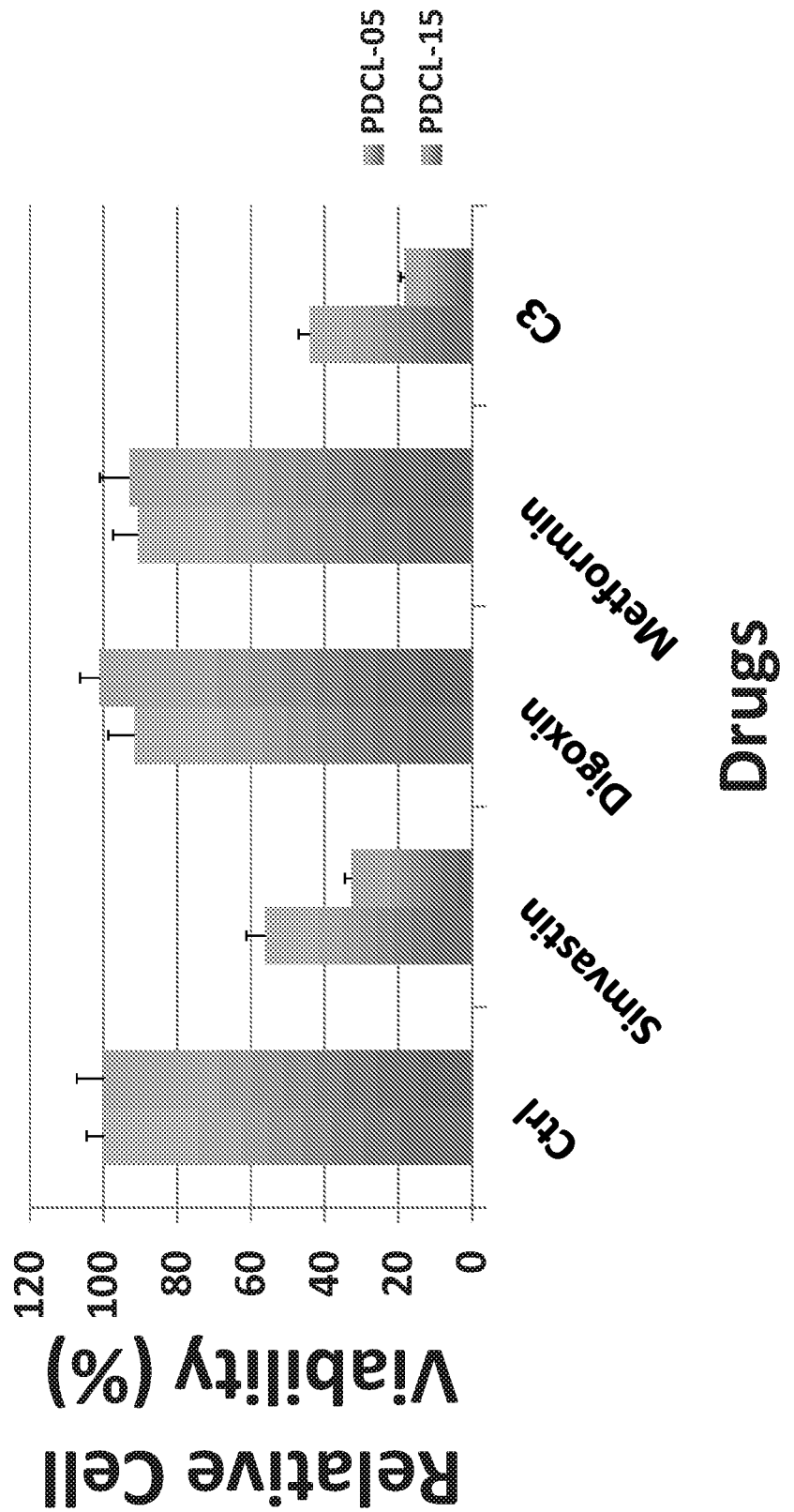
FIG. 3 is a graph illustrating that treatment with individual drugs simvastatin, metformin, and digoxin and the triple drug combination (C3) of metformin, simvastatin and digoxin suppresses patient-derived pancreatic cancer cell (#5 and #15) viability in vitro, in accordance with one or more embodiments of the invention. The control is represented as Ctrl. Notably, there is significantly greater suppression of the patient-derived pancreatic cancer cell lines with the triple drug combination (C3) when compared to the individual drugs and control.
Figure 4:
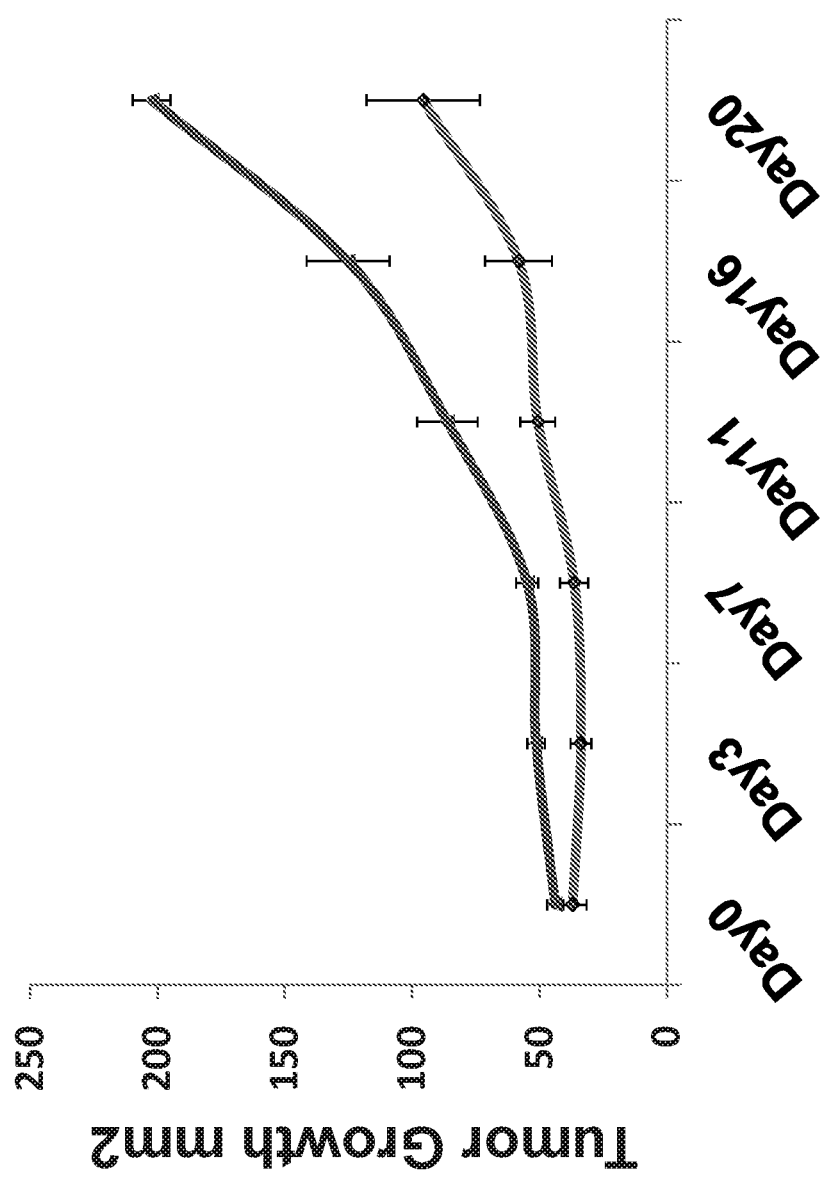
FIG. 4 is a graph illustrating that the tumor growth of commercial pancreatic cancer cell line MIA PaCa2 is greatly suppressed by the triple drug combination (C3) of metformin, simvastatin and digoxin when compared to phosphate buffered saline in mice, in accordance with one or more embodiments of the invention.
Figure 5:
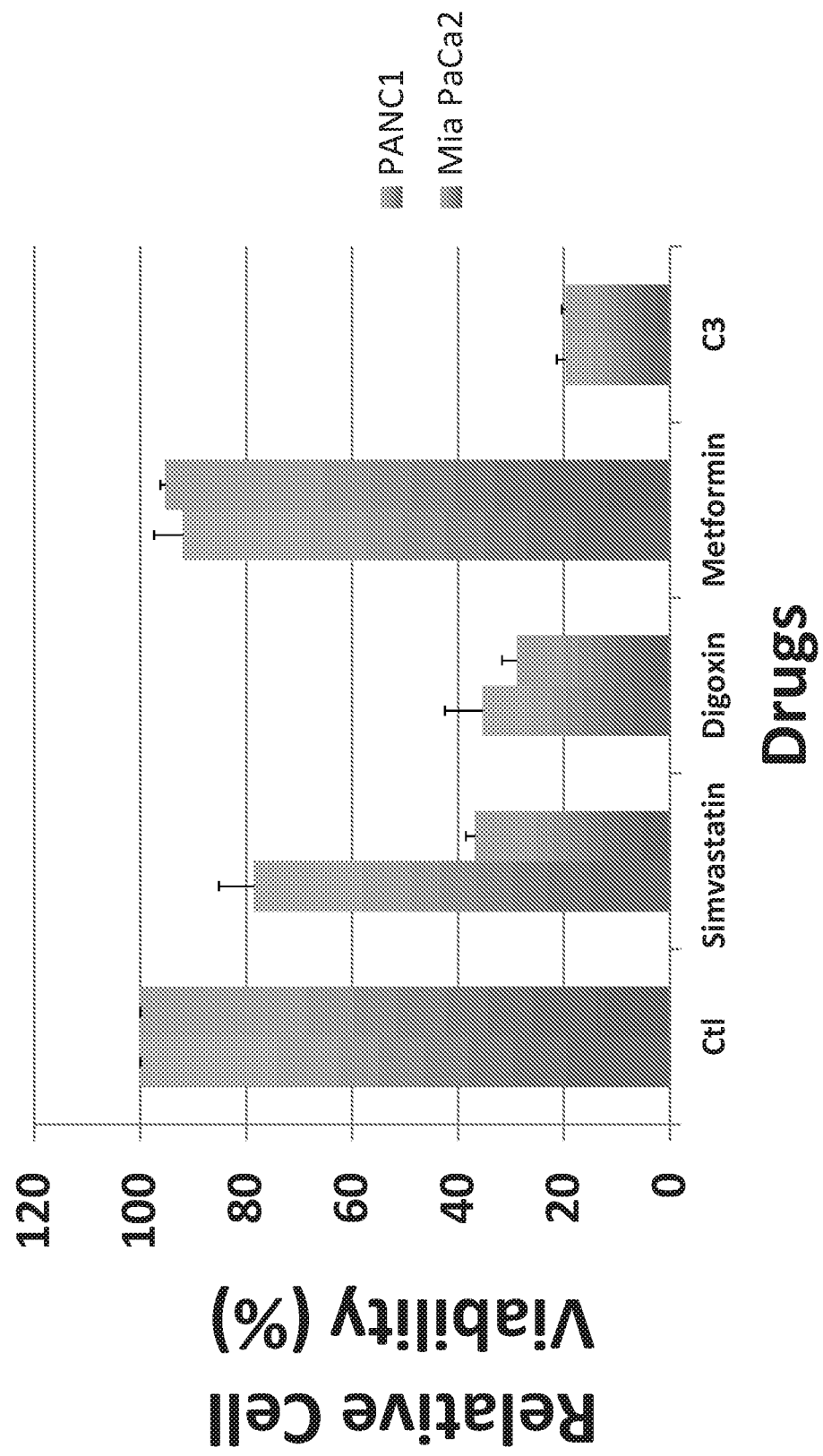
FIG. 5 is a graph illustrating that treatment with the individual drugs simvastatin, metformin, and digoxin and the triple drug combination (C3) of metformin, simvastatin and digoxin suppresses commercial human pancreatic cancer cell lines (MIA PaCa2 and PANC1) viability in vitro, in accordance with one or more embodiments of the invention. The control is represented as Ctrl. Notably, there is significantly greater suppression of the commercial human pancreatic cancer cell lines with the triple drug combination (C3) when compared to the individual drugs and control.
Figure 6:
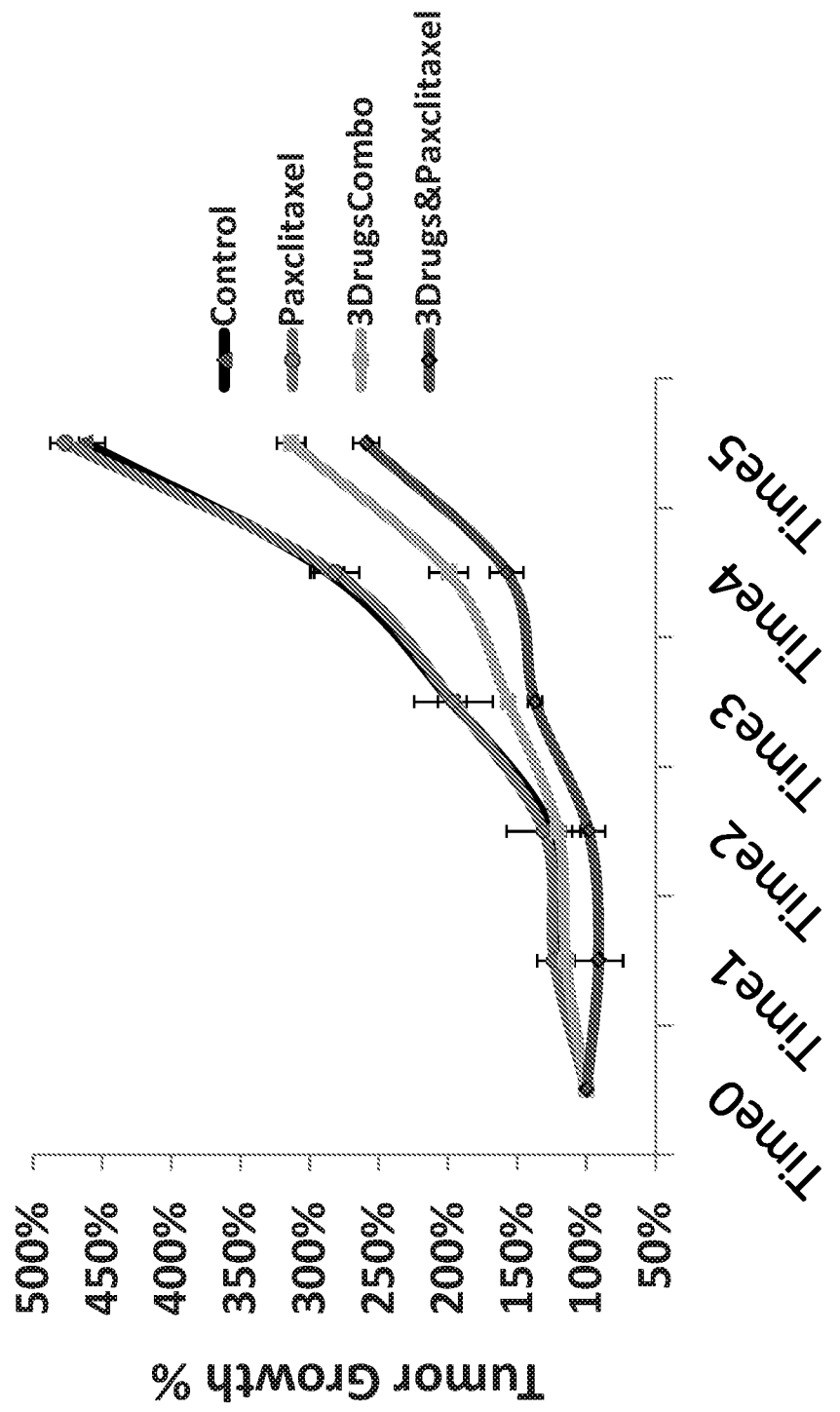
FIG. 6 is a graph illustrating that MIA PaCa2 tumor growth is suppressed by the triple drug combination (3DrugsCombo) of metformin, simvastatin and digoxin, with and without paclitaxel in mice, in accordance with one or more embodiments of the invention.
Figure 7:
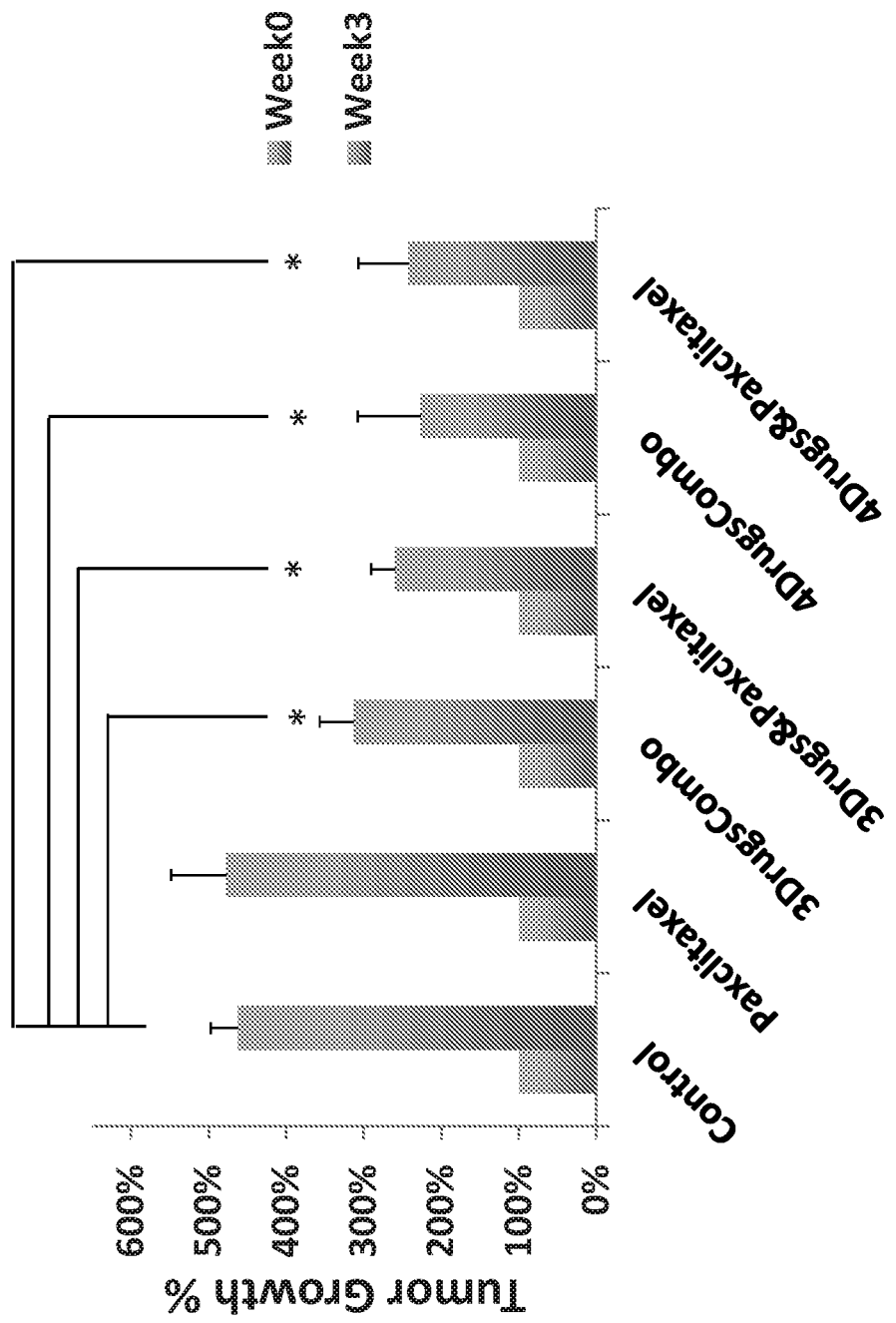
FIG. 7 is a graph illustrating that MIA PaCa2 tumor growth is suppressed by the triple drug combination (3DrugsCombo) of metformin, simvastatin, and digoxin as well as the 4 drug combination (4DrugsCombo) of metformin, simvastatin, digoxin, and A23187, with and without paclitaxel in mice, in accordance with one or more embodiments of the invention.
Figure 8:
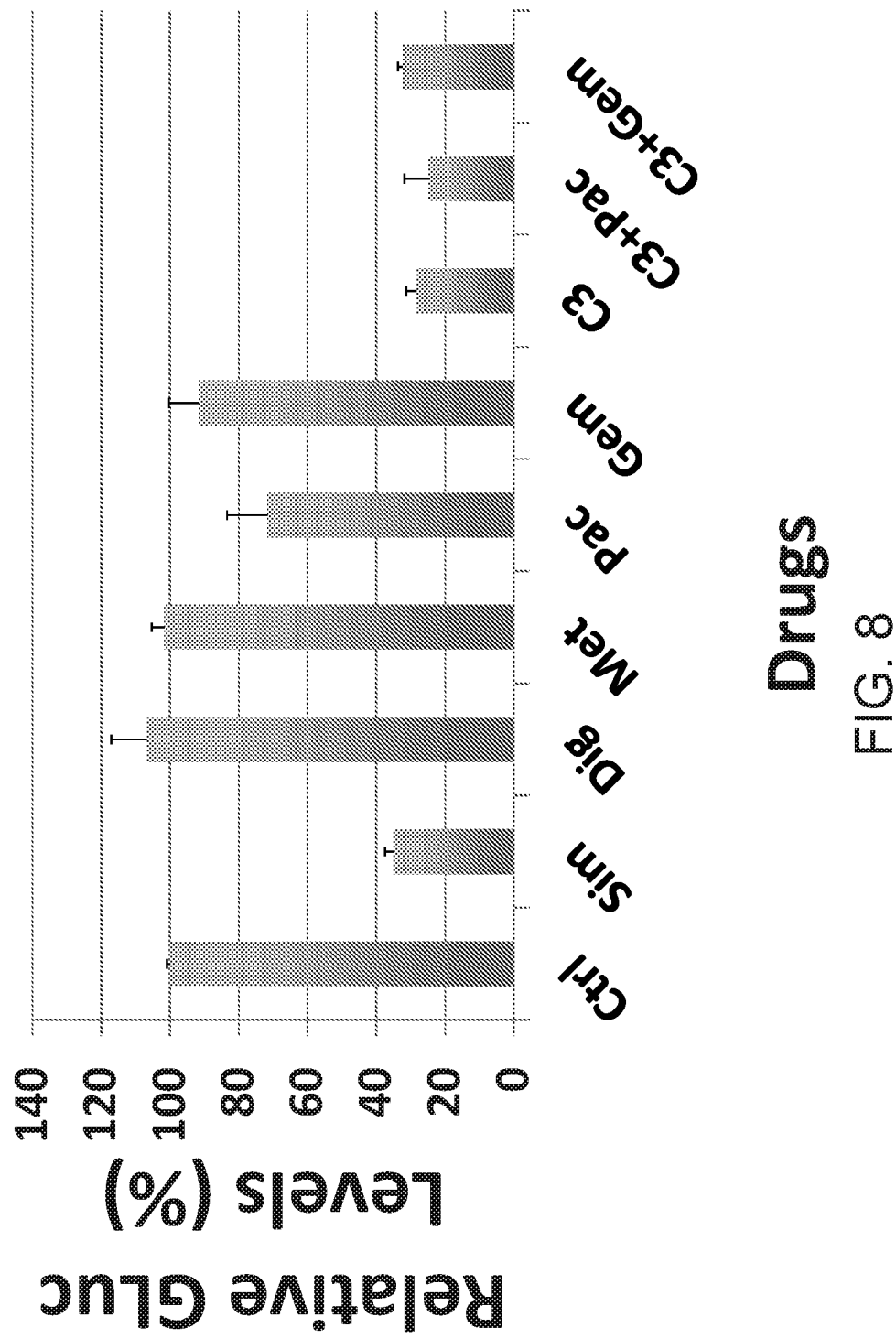
FIG. 8 is a graph illustrating that treatment with individual drugs simvastatin (Sim), metformin (Met), and digoxin (Dig) and the triple drug combination (C3) of simvastatin, metformin, and digoxin suppress patient-derived pancreatic cancer cell #5 viability with and without paclitaxel (Pac) and gemcitabine (Gem) in vitro, in accordance with one or more embodiments of the invention. The control is represented as Ctrl. Notably, there is significantly greater suppression of patient-derived pancreatic cancer cell #5 with the triple drug combination (C3) as well as the triple drug combination with paclitaxel (C3+Pac) or gemcitabine (C3+Gem) when compared to the individual drugs and control.
Figure 9:
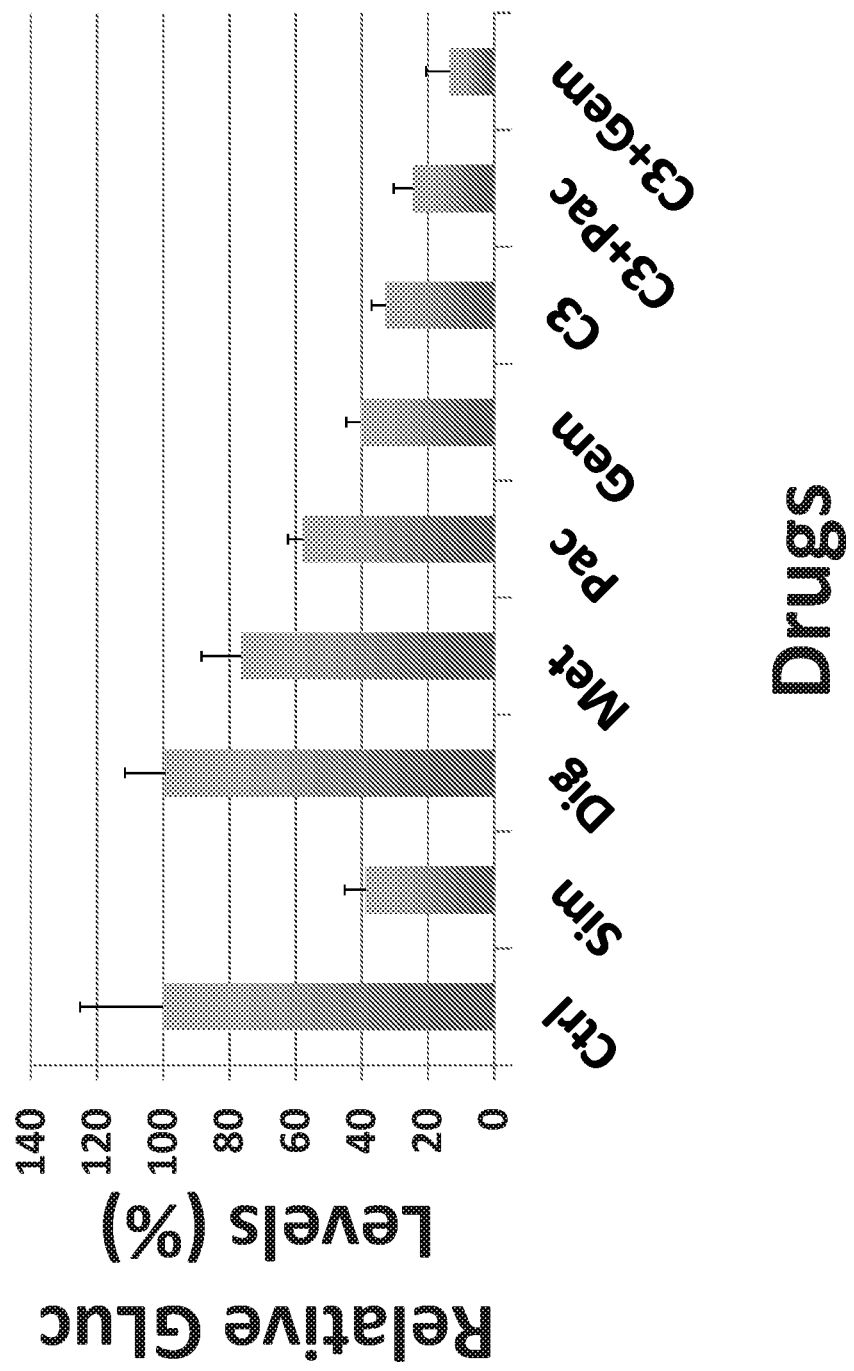
FIG. 9 is a graph illustrating that treatment with individual drugs simvastatin (Sim), metformin (Met), and digoxin (Dig) and the triple drug combination (C3) of simvastatin, metformin, and digoxin suppress patient-derived pancreatic cancer cell #15 viability with and without paclitaxel (Pac) and gemcitabine (Gem) in vitro, in accordance with one or more embodiments of the invention. The control is represented as Ctrl. Notably, there is significantly greater suppression of patient-derived pancreatic cancer cell #15 with the triple drug combination (C3) as well as the triple drug combination with paclitaxel (C3+Pac) or gemcitabine (C3+Gem) when compared to the individual drugs and control.
Figure 10:
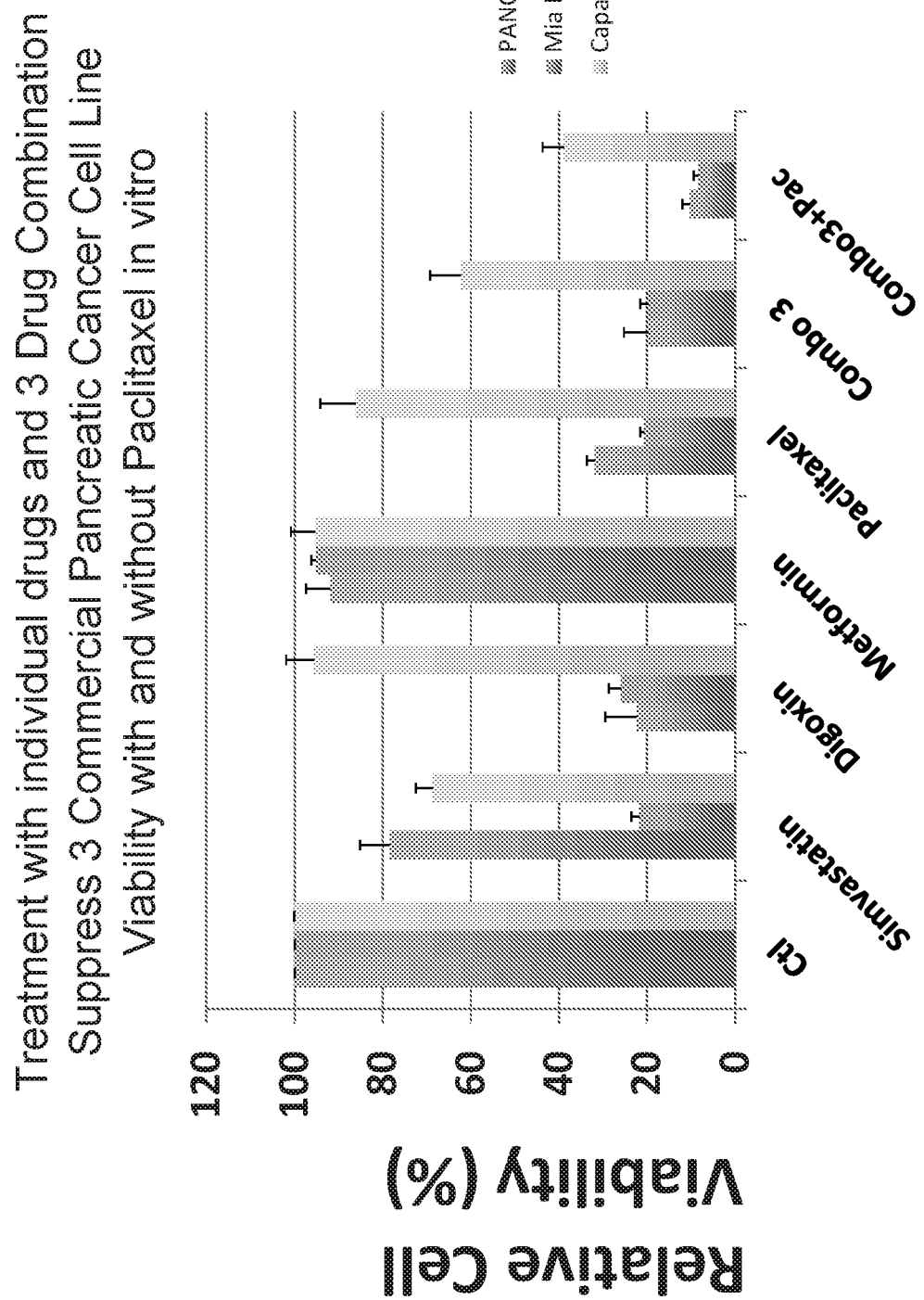
FIG. 10 is a graph illustrating that treatment with individual drugs simvastatin, metformin, and digoxin and the triple drug combination (Combo 3) of metformin, simvastatin, and digoxin suppress three commercial pancreatic cancer cell line viability (PANC, MIA PaCa2, and Capan2) with and without paclitaxel in vitro, in accordance with one or more embodiments of the invention. Notably, there is greater suppression of PANC and MIA PaCa2 with the triple drug combination (Combo 3) as well as the triple drug combination with paclitaxel (Combo3+Pac) when compared to the individual drugs and control.
Figure 11:
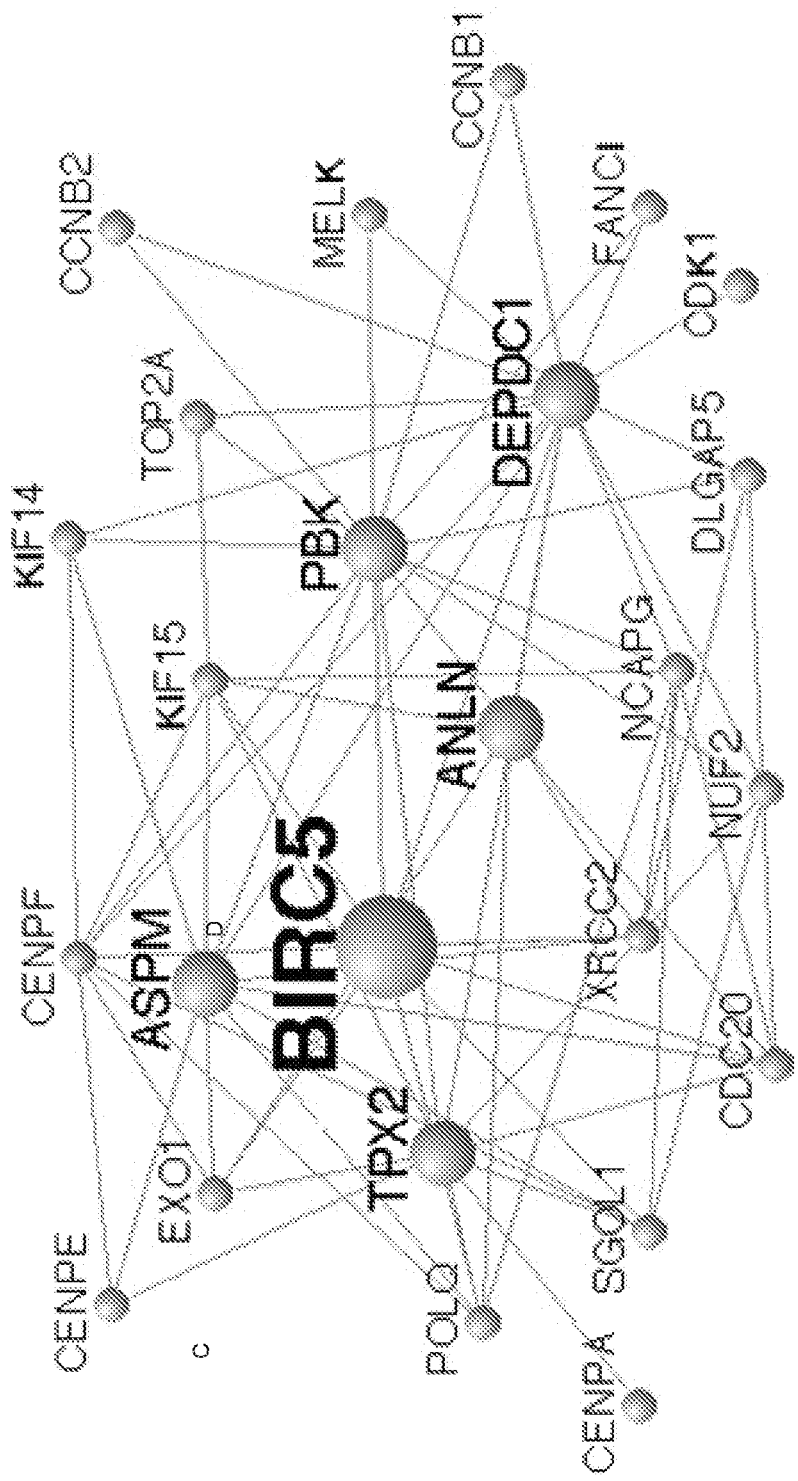
FIG. 11 illustrates a cell cycle network of the most highly connected genes. BIRC5 is identified as an actionable hub gene for pancreatic cancer (i.e. gene on which action can be taken to alter disease progression or guide choice of therapy), in accordance with one or more embodiments of the invention.
Figure 12:
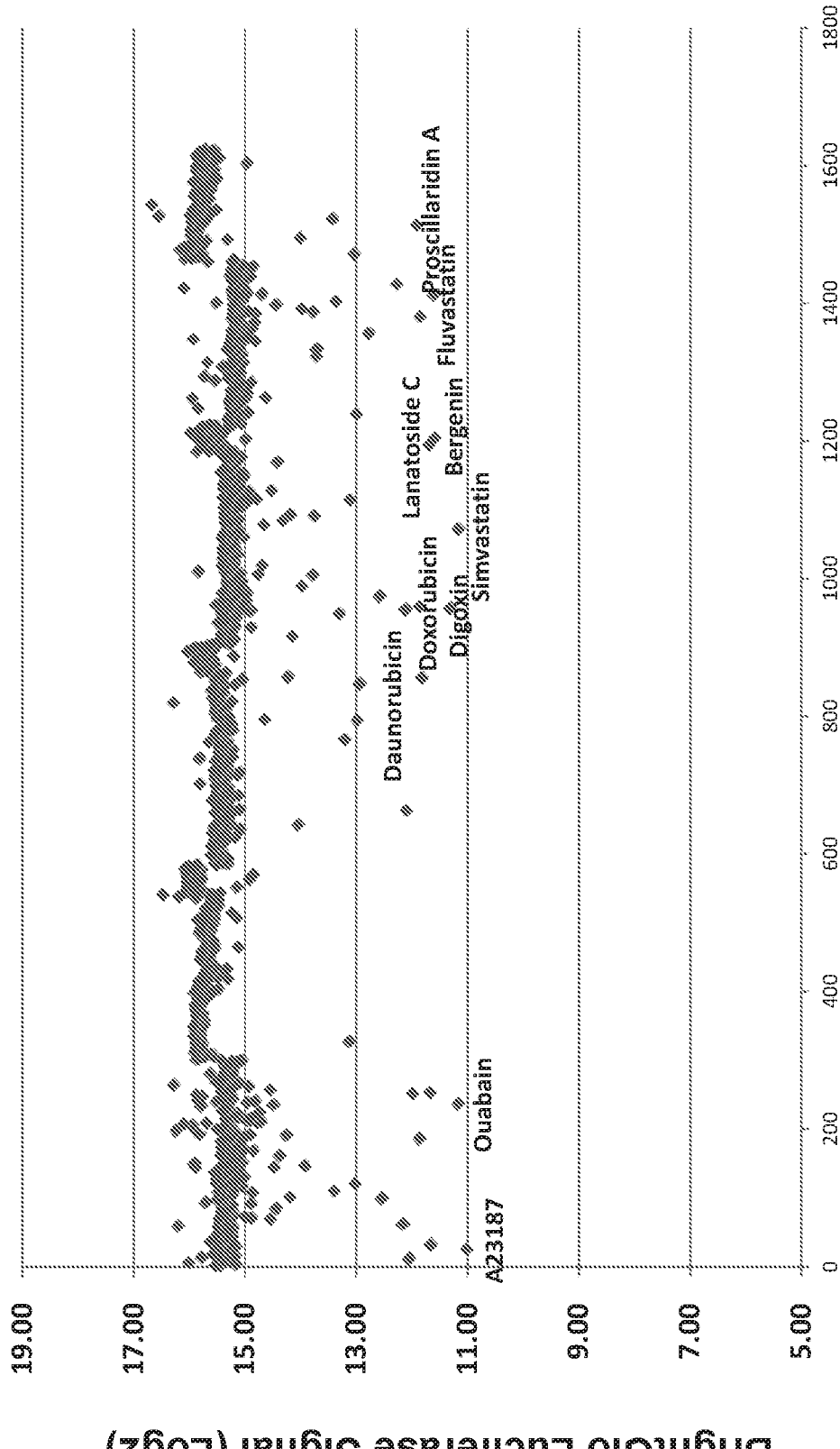
FIG. 12 is a graph illustrating BIRC5 SP high-throughput (HTS) drug screening in MIA PaCa2 cells, in accordance with one or more embodiments of the invention.
Figure 13:
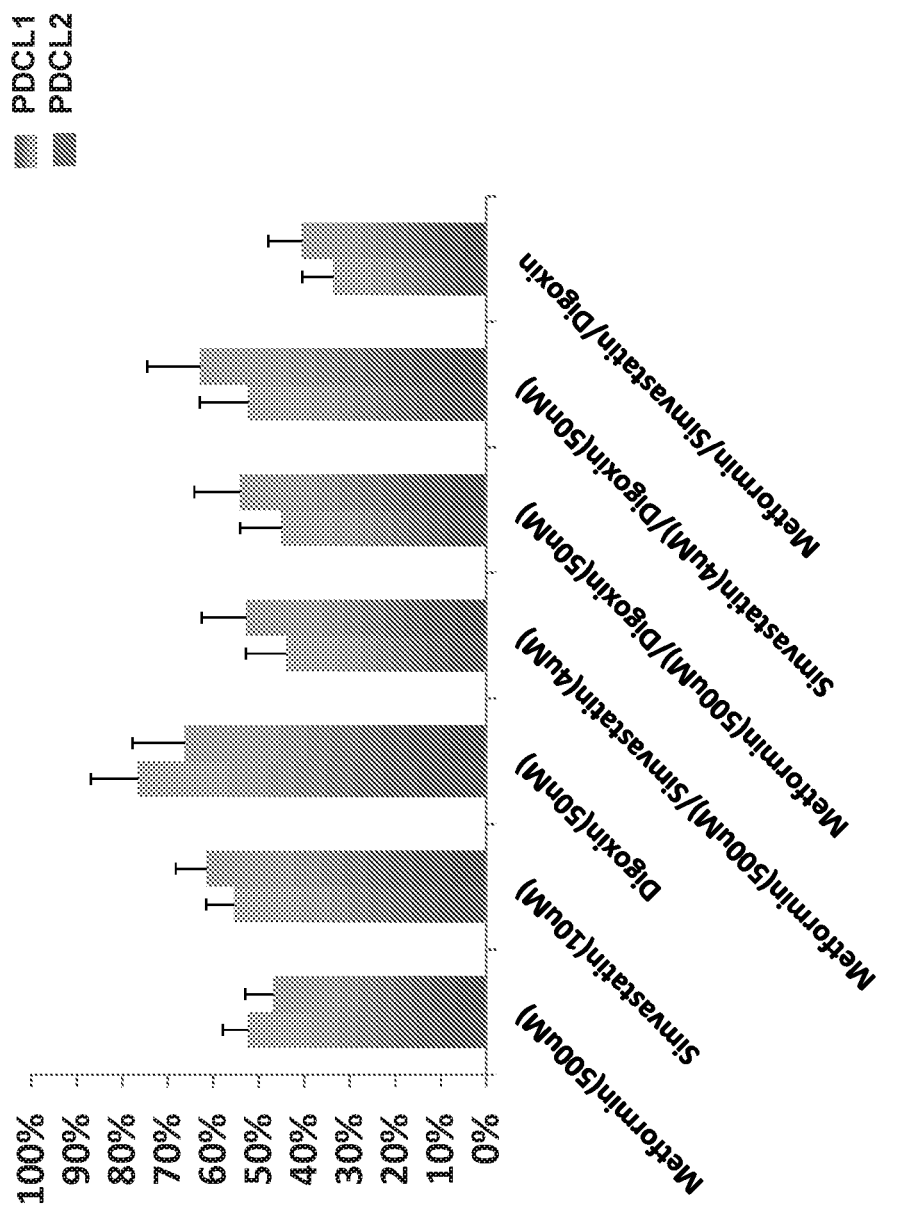
FIG. 13 is a graph illustrating that treatment with individual drugs simvastatin, metformin, and digoxin and various combinations of the individual drugs suppress patient derived pancreatic cancer cell lines #5 and #15 BIRC5 mRNA expression (gene transcription) in vitro, in accordance with one or more embodiments of the invention.

An important point to note is that the triple drug combination has been tested in patient-derived cell lines from the pancreatic cancer of known patients (FIGS. 1-3). These patients' pancreatic cancer cell lines over expressed BIRC5, a target for the triple drug combination. The triple drug combination was also tested in commercial pancreatic cancer lines, MIA PaCa2 and PANC1 (FIGS. 4-5). These are the standard pancreatic cancer cell lines that almost all research groups in the art use to test therapies; they are useful to work out the in vivo and in vitro dosages needed for efficacy. MIA PaCa2 cell line and PANC1 were generated from patients in 1975, therefore, these pancreatic cancer cell lines are 41 years old with millions of passages, so it is hard to determine whether the current cells are the same cells as those developed from the patients in 1975.

These in vitro and in vivo data demonstrate that the combination of 3 FDA approved drugs, metformin, simvastatin, and digoxin, effectively inhibit proliferation in vitro via down-regulation of BIRC5 and other cell cycle-related genes. More importantly, the combination of 3 FDA approved drugs significantly reduced PDAC and PDCL tumor growth in mice in vivo with no toxicity. We conclude that the repurposing of metformin, simvastatin, and digoxin in combination (as a composition of matter named Silencium™) provides an effective and non-toxic therapy for patients with pancreatic cancer.

Furthermore, we analyzed mRNA expression from published databases of 9 major cancers in nearly 1000 samples (see also Example 5). We processed the Data using Weighted Gene Co-expression Network Analysis (WGCNA) and demonstrated a network of actionable genes that are common to all 9 cancers. BIRC5 is one of these network genes, thus supporting the hypothesis that the triple drug combination will effectively suppress all 9 major cancers (see FIGS. 27-30).

Example 2: Dosing

The dosages of the therapeutic compounds metformin, simvastatin, and digoxin for both in vitro and in vivo uses were determined from $IC_{50}$ tests and published studies by other research groups (see Tables 1-3). Table 1 shows the drug doses used in mice and the doses used in other studies. Table 2 shows the drug doses used in human cell lines in vitro. Table 3 shows the oral drug dose range that is commonly used in humans for metabolic diseases.

TABLE 1

| Drugs | In vitro con. | Used in other studies | In vivo dose | Lethal Dose ($LD_{50}$) | Used in other studies |
|---|---|---|---|---|---|
| Simvastatin | 4 µM | 250 nM ~ 32 µM | 20 mg/kg | 798 mg/kg | 20 mg/kg |
| Digoxin | 50 nM | 10 nM ~ 500 nM | 2 mg/kg | 4 mg/kg | 2 mg/kg |
| Metformin | 500 µM | 300 µM ~ 40 mM | 100 mg/kg | 477 mg/kg | 50 ~ 250 mg/kg |

TABLE 2

| Drugs | Final Concentration | µM |
|---|---|---|
| Simvastatin | 4 µM | 4 |
| Digoxin | 50 nM | 0.05 |
| Metformin | 500 µM | 500 |
| Paclitaxel | 100 nM | 0.1 |

TABLE 3

| Triple Drug Combo (human) | |
|---|---|
| Simvastatin | 10-80 mg/day PO |
| Digoxin | 0.125-0.250 mg/day PO |
| Metformin | 500-2550 mg/day PO |

For in vitro cancer cell treatment experiments, the dosages of simvastatin used ranged from 250 nM 32 µM on various cancer types [8, 9]. We used 4 µM on pancreatic cancer cell lines in our experiments based on $IC_{50}$ tests on our own testing of commercial human pancreatic cancer cells. For in vivo treatment experiments, simvastatin was administrated via intraperitoneal injection and the dosage of simvastatin was used at 20 mg/kg body weight [10], based on other studies and that the lethal dose for mice ($LD_{50}$) of simvastatin is 798 mg/kg [29].

For metformin, the dosages of metformin used in other studies ranged from 0.3~40 mM on various cancer cell lines [11-13]. We chose 500 µM on pancreatic cancer cell lines in our experiments based on our own $IC_{50}$ testing on commercial human pancreatic cancer cells. For the in vivo treatment experiments, metformin was delivered intraperitoneally at a dose of 100 mg/kg body weight, since similar dosages of 50~250 mg/kg have been used in another animal test and the lethal dose for mouse ($LD_{50}$) of metformin is 477 mg/kg [14, 15].

For digoxin, the dose range of digoxin was 10~500 nM in cancer cell lines in other studies [16]. We chose 50 nM for the in vitro pancreatic cancer cell line studies based on our $IC_{50}$ testing of commercial human pancreatic cancer cells. For in vivo treatment experiments, digoxin was delivered intraperitoneally at a dose of 2 mg/kg body weight, since the same dosage was used in another mouse study, and the lethal dose ($LD_{50}$) of digoxin is 4 mg/kg in mice (SAAPedia) [17].

The doses that would be used in clinical trials described herein are: simvastatin 5-80 mg/day po, metformin 500-2000 mg/day po, digoxin 0.125-0.250 mg/day po. Comparable (or even higher) doses were used in mice and the triple drug combination was non-toxic to the mice in two preclinical trials. One clinical trial used metformin (1700 mg/day) and simvastatin (20 mg/day). The composition is relatively non-toxic, especially compared to standard chemotherapy agents. Moreover, there is no toxicity detected using the dosages described herein.

Example 3: Human PC Cells and Mouse Models

For in vitro studies of human pancreatic cancer, there are commercial pancreatic cancer cells and patient derived pancreatic cancer cell lines (PDCLs). The commercial pancreatic cancer cell lines have been used in hundreds of studies and are hearty and reliable. They can be used for high throughput screening of drugs. High-quality primary tumor tissue with detailed clinical background information offers a valuable resource for tumor biomarker identification, as well as a better alternative for preclinical drug evaluation.

PDCLs are derived directly from a patient's cancer, thus testing drugs in these cells would be the closest thing to actually testing the drugs in the patient. A collaborating Pancreas Center has established standard operating procedures (SOPs) for derivation of PDCLs, which were matched to clinical databases and provided 16 PDCLs. Two of these PDCLs (#5 and #15) were used for in vitro drug testing of the 3 drug combination and #15 was used for in vivo testing of the 3 drug combination in mice.

In attempting to mimic human PDAC development, more than 20 models of genetically-engineered PDAC in mice have been generated and studied [18, 19], in which expression of mutant constitutively active Kras G12D in mouse pancreas leads to PanINs and then PDAC [20]. Other studies demonstrated that combined Kras activation and loss of tumor suppressor p53 in mice produces distinct phenotypes of pancreatic carcinogenesis, invasion and metastasis that recapitulate the genetic and pathologic profile of human PDAC [21]. All mice used in the studies were Nu/Nu nude mice. The pancreatic cancer cells were placed in the subcutaneous tissues of the flank and grown for 9 days before the treatment was initiated. The tumors are measured using digital calipers. FIG. 2 demonstrates the difference in bioluminescence relative light units between the control tumor and the triple drug combination treated tumors, which confirms the tumor size measurement.

The most widely used animal model is the human tumor xenograft, in which, human tumor cells are transplanted, either under the skin or into the organ type in which the tumor originated, into immuno-compromised mice [22, 23]. Depending on the number of cells injected, the tumor will develop over 1-8 weeks (or longer), and the response to appropriate therapeutic regimes can be studied in vivo [15, 24]. The human tumor xenograft model is used in the illustrative experiments described herein since it is the optimal model for testing the triple drug combination against human pancreatic cancer cells. In the first model, MIA PaCa2 cells were placed subcutaneously so the tumor size could be readily measured over time and could also be imaged. MIA PaCa2 cells are commercially available and are widely used for these types of studies.

The second model is a patient derived xenograft model; one where cancer cells derived from a known patient, whose genome was fully characterized, were used in this model, thus one could say the triple drug combination therapy has been tested in a known patient's pancreatic cancer in vitro as well as in xenograft mice in vivo. High-quality primary tumor tissue with detailed clinical background information offers a valuable resource for tumor biomarker identification, as well as a better alternative for preclinical drug evaluation. Of the 16 patient derived pancreatic cancer cell lines (PDCLs), two have been studied in vitro (#5 and #15) and one has been studied in vivo (#15). PDCL cells from patient #15 were placed subcutaneously so the tumor size could be readily measured over time and could also be imaged.

Example 4: Triple Drug Combination Inhibits Pancreatic Cancer Growth Via Warburg Effect Pancreatic cancer is one of the most deadly cancers known, with an overall 5-year survival rate less than 5% due to the poor early diagnosis and lack of effective therapeutic options. One of the most important observations was that the pancreatic cancer cells predominantly utilize cytosolic aerobic glycolysis and lactate fermentation rather than mitochondrial oxidative phosphorylation of pyruvate for their energy production, which was firstly described as the 'Warburg effect' in 1920s. In our study, we identified a triple drug combination (C3) that significantly decreased cell proliferation and increased cell apoptosis in patient derived cancer cell lines (PDCLs) in vitro. Further transcriptome analysis indicated that the overexpression of Warburg effect related enzymes including hexokinase 2 (HK2), lactate dehydrogenase A and B (LDHA, LDHB), enolase 2 (ENO2) were reversed by treatment of C3 on PDCLs. The treatment of C3 on human xenograft tumor in animal model in vivo further confirmed the inhibitory role of C3 were via Warburg effect, however, further preclinical analysis were still needed to validate the molecular targets and mechanisms of C3 on pancreatic cancers.

Example 5: Cancer Microarray Data Weighted Gene Co-Expression Network Analysis Identifies A Unique Module and Hub Genes Common to 9 Type of Cancers Introduction Cancer, also known as a malignant tumor, is a large family of diseases involving unregulated cell overgrowth with potential invasion and metastases. In 2014, there were more than 1.6 million new cancer cases and over 0.5 million cancer related deaths occurred in the United States [57, 58]. It is known that cancer develops in virtually any of the human body's tissues, but each type of cancer usually has its unique features and different incidence rates. Throughout last decade, tremendous efforts have been made toward the understanding of the biology of the family of disaster diseases. In particular, high-throughput genomic techniques microarray and next-generation sequencing have revealed a series of somatic mutations and differentially expressed genes associated with multiple cancers [59-62]. However, these massive genomic data have yet successfully affected care of patients suffering from these diseases. Therefore, a systematic data analysis strategy to read, understand and translate critical information into effective therapeutic platforms is needed. Our objective was to identify a set of actionable genes for cancers using a novel combination of systematic genomic analysis and published cancer microarray databases.

Several approaches that focus on construction of networks between genes and phenotypes have been proven in revealing the functional pathways, as well as underlying causal genes of complex diseases recently. In particular, The Weighted Gene Co-expression Network Analysis (WGCNA) developed by Horvath and his team has been extensively utilized to analyze whole-genome gene expression profiles of microarray and RNA-Seq data [63-66]. By utilizing the pairwise Pearson's correlation between gene expression values to calculate the connectivity between pairs of genes, WGCNA is able to define gene modules as a group of densely interconnected genes in weighted network analysis from a number of samples. WGCNA has proven its ability to identify biologically relevant gene modules, hub genes and enriched signaling pathways for each module in multiple complex diseases. Herein, we propose to perform WGCNA on gene expression profiles from existing microarray data sets on multiple type of cancers to detect highly interconnected gene modules that is common to all type of cancer in order to accelerate the understanding of cancer biology and promote the translation of a patient's genomic information into potential targeted gene therapies in the near future.

Materials and Methods

Gene Expression Microarray

In this study, we collected and analyzed a total of 12 gene expression microarray datasets that contain 9 type of cancers were downloaded from the Gene Expression Omnibus, including 104 breast cancer [67], 117 brain tumor [68], 32 colon cancer [69], 108 gastric cancer [70, 71], 95 liver cancer, 60 lung cancer [72], 72 pancreatic cancer [73, 74], 72 renal cancer [75], 26 prostate cancer [76, 77] and a total of 330 matching non-tumor control tissue samples.

WGCNA Analysis

A weighted gene co-expression network analysis (WGCNA) was used to construct gene co-expression networks for cancers and to detect specific gene modules for cancers. Weighted Gene Co-expression Network Analysis (WGCNA) was used for scale-free network topology analysis of microarray expression data. The WGCNA R package was used to cluster highly correlated genes and find clusters whose expression was correlated with the traits examined. WGCNA was carried out on data from all 12 gene-expression microarray datasets for a total number of 1016 tumors and matched normal control samples [67, 68, 78]. An adjacency matrix based on expression correlation was created using a soft threshold procedure to allow a scale free topology. The clusters created by WGCNA are called modules, and the minimum number of genes in a module was set to 30. Standard WGCNA parameters were used for analysis, with the exceptions of soft-thresholding power and deep split. A soft-thresholding power of 9 was used for all samples. Modules were validated by bioinformatics analysis for over-represented biological functions (see below).

GO Term Enrichment Analysis

Throughout the analysis, the functional annotation tool DAVID Bioinformatics Resources 6.7 was used to determine gene ontology terms enriched by a list of genes. DAVID analyses were performed on lists of genes corresponding to significant WGCNA modules. WGCNA modules were considered significant for a certain trait when the nominal p-value of the correlation between the ME and the trait of interest was less than 0.10.

Immunoflorescent Staining

Anti-CDK1 (abcam ab193829), BIRC5 (abcam ab175809), TPX2 (ab32795) antibodies were applied to slides with human pancreatic cancer specimens with 1:100 dilution followed by overnight incubation at 4° C. Slides were incubated with FITC-conjugated anti-rabbit or mouse secondary antibody depending on derivation of primary antibodies for one hour, and mounted with cover slides. To visualize the nuclei, VECTASHIELD® Mounting Medium with DAPI was used (10 ul per slide).

Results

WGCNA of a total of 1016 cancer gene expression data revealed specific gene modules for each type of all 9 cancers. Gene co-expression networks were constructed and hub genes for all types of 9 cancers were identified. More importantly, one particular module that contains differentially overexpressed genes across all 9 types of cancers versus their matching non-tumor controls was identified, in which the hub genes BIRC5, TPX2, CDK1, and MKI67 were significantly enriched in cell cycle and cell proliferation pathways and have been previously shown associated with cancers.

The Use of Microarray Datasets to Analyze Gene Expression Differences in Multiple Cancers In this study, we downloaded a selection of 12 gene-expression microarray datasets that contain 9 cancers and are with Affymetrix Human Genome U133 Plus 2.0 Array platform (GPL570) from the Gene Expression Omnibus (GEO) Database. These 12 microarray datasets are all gene expression profiles of human tumor specimens and matching non-tumor control samples, including 104 breast cancer [67], 117 brain tumor [68], 32 colon cancer [69], 108 gastric cancer [70, 71], 95 liver cancer, 60 lung cancer [72], 72 pancreatic cancer [73, 74], 72 renal cancer [75], 26 prostate cancer [76, 77] and a total of 330 matching non-tumor control tissue samples. These 12 microarray datasets were generated in multiple cancer institutes worldwide from 2005 to 2014 (Tables 4A and 4B).

TABLE 4A

| Cancer Type | MicroArray Platform | Year Published | Tumor Samples | Control Samples | Author | Data ID |
|---|---|---|---|---|---|---|
| Breast Cancer | GPL570 | 2013 | 104 | 17 | Colin Clark | GSE42568 |
| Brain Cancer | GPL570 | 2013 | 117 | 13 | Andrew M. Donson | GSE50161 |
| Colon Cancer | GPL570 | 2007 | 32 | 32 | Sabates-Beliver J | GSE8671 |
| Gastric Cancer | GPL570 | 2012 | 70 | 0 | Zhengdeng Lei | GSE35809 |
| Gastric Cancer | GPL570 | 2008 | 38 | 31 | Via potina | GSE13911 |
| Liver Cancer | GPL570 | 2014 | 95 | 39 | Jui-Yu Hseih | GSE45436 |
| Lung Cancer | GPL570 | 2011 | 60 | 60 | Tzu-Pin Lu | GSE19804 |
| Pancreatic Cancer | GPL570 | 2009 | 36 | 36 | Liviu Badea | GSE15471 |
| Pancreatic Cancer | GPL570 | 2009 | 36 | 16 | Huadong Pei | GSE16515 |
| Renal Cancer | GPL570 | 2014 | 72 | 72 | Christina A von Roemeling | GSE53757 |
| Prostate Cancer | GPL570 | 2005 | 13 | 6 | Jianjun Yu | GSE3325 |
| Prostate Cancer | GPL570 | 2014 | 13 | 8 | Arredouani MS | GSE55945 |

TABLE 4B

| Cancer Type | Cancer | Year | Tumor | Control | DataID |
|---|---|---|---|---|---|
| Breast Cancer | Eighty-two were invasive ductal carcinoma, 17 were invasive lobular and five were tumours of special type (two tubular and three mucinous). Eleven tumours were grade 1; 40 were grade 2; and 53 were grade 3. Sixty-seven tumours were oestrogen receptor (ER) positive and 34 were ER negative (ER status was determined by Enzyme Immuno-Assay (EIA) | 2013 | 104 | 17 | GSE42568 |
| Brain Cancer | The gene expression study sample dataset included 15 PA, 46 EPN, 20 GBM, 22 MED and 13 NT brain samples. | 2013 | 117 | 13 | GSE50161 |
| Colon Cancer | colorectal adenomas | 2007 | 32 | 32 | GSE8671 |
| Gastric Cancer | gastric adenocarcinoma | 2012 | 70 | 0 | GSE35809 |
| Liver Cancer | hepatocellular carcinoma | 2014 | 95 | 39 | GSE45436 |
| Lung Cancer | Non-small cell lung carcinoma | 2011 | 60 | 60 | GSE19804 |

TABLE 4B-continued

| Cancer Type | Cancer | Year | Tumor | Control | DataID |
|---|---|---|---|---|---|
| Pancreatic Cancer | pancreatic ductal adenocarcinoma | 2009 | 36 | 36 | GSE15471 |
| Pancreatic Cancer | pancreatic ductal adenocarcinoma | 2009 | 36 | 16 | GSE16515 |
| Renal Cancer | clear cell renal cell carcinoma | 2014 | 72 | 72 | GSE53757 |
| Prostate Cancer | prostate cancer tumors that are benign, clinically localized, or metastatic | 2005 | 13 | 6 | GSE3325 |
| Prostate Cancer | prostate benign and malignant tissue | 2014 | 13 | 8 | GSE55945 |

For analyzing differentially expressed genes (DEGs) between colon cancer versus control samples, we combined two data sets on the Affymetrix HG-U133 Plus 2.0 platform and processed the dataset GSE8671 colon cancer and 32 control tissue gene expression profiles, a list of 2722 probes, which reflect a total of 1914 unique genes with at least two fold change and a P value is less than 1.0E-6, were revealed to be significantly differential expressed. These identified DEGs consist of 968 unique, up-regulated genes (1311 probes) and 946 unique, down-regulated genes (1411 probes) in colon cancer. Using the similar strategy, we further identified DEGs between normal and tumor tissues of breast cancer, gastric cancer, brain cancer, liver cancer, lung cancer, pancreatic cancer, renal cancer and prostate cancer, respectively. FIG. 27 shows the heatmaps and hierarchical clustering of the 100 most significantly differentially up-regulated or down-regulated genes between each type of cancer versus their matching non-tumor normal tissues, respectively. These DEGs could easily distinguish cancer versus their matching non-tumor normal tissues from gene expression patterns (FIG. 27). These results indicated that analysis of gene-expression microarray dataset of individual cancer samples could reveal cancer specific DEGs and these DEGs potentially distinguish cancer versus non-tumor tissues.

WGCNA Analysis Identifies Co-Expressed Genes Whose Expression Pattern was Significantly Correlated with all 9 Cancers Regular Affymetrix microarray data analysis packages can effectively identify DEGs through pair-wise comparisons. However, these tools have limitations when handling whole genome gene expression data with multiple traits in complicated diseases. A new systematic approach WGCNA has proven its ability to identify biologically relevant gene modules, hub genes and enriched signaling pathways for each module and to reveal the biology of complicated diseases. Therefore, to better understand the systematic level organization of the gene expression changes occurring in the tumor specimens versus non-tumor control samples of multiple cancers, we constructed weighted gene co-expression networks using differential gene-expression values between each individual tumor specimen versus the average of gene-expression values of matching non-tumor control specimens by applying WGCNA. This study was based on a collection of published gene-expression microarray datasets from a total of 9 types of cancer, which contains gene expression data from 686 cancers and 330 matching non-tumor control samples. For this study, we restricted the analysis to the 12576 genes with average gene-expression value higher than 5 in the Affymetrix Human Genome U133 Plus 2.0 microarray analysis. Firstly, the differential gene-expression values between each individual tumor specimen versus the average of gene-expression values of matching non-tumor control specimens were calculated and these differential gene-expression values were used to construct networks using WGCNA. In order to do so, the value of Pearson correlation between all pairs of values was calculated and then was used to measure the connection strengths between the gene and all the other genes in the network. Using hierarchical average linkage clustering, WGCNA is able to created 10 unique gene co-expression modules based on the gene expression patterns across all cancer samples and each module was assigned a color label. Among these modules, one module (the red module) was shown to positively correlate with all type of cancers (FIG. 28).

To further determine the biological function of the important module genes, DAVID Gene Ontology (GO) analysis was examined in the gene lists of red and other modules. The red module was significantly enriched for cell cycle related biological functions (FIG. 29). Some of the big "hub genes" in this red module were BIRC5, TPX2, CDK1, and MKI67 respectively (FIG. 30). To validate the over-expression of these hub genes in cancer cells, we performed immunoflorescent staining on human pancreatic cancer specimens. The staining of BIRC5, TPX2 and CDK1 hub genes on pancreatic cancer specimens showed a significant over-expression of all three genes in both pancreatic intraepithelial neoplasia (PanIN) and metastatic pancreatic cancer cells (FIG. 31). These results indicated that genes involving pathways related to cell cycle were highly expressed in pancreatic cancer cells, supporting the idea that tumor cells have a higher proliferating rate compare to normal cells. These data further proved the capacity of using WGCNA to identify biologically relevant gene modules, hub genes and enriched signaling pathways for complicated diseases including multiple cancers.

Conclusions

The systematic genomic analysis utilizing a large collection of cancer gene-expression microarray datasets and WGCNA reveals a set of cancer actionable genes. A shared gene module containing cancer actionable genes involving cell cycle and cell proliferation pathways were identified, supporting the idea that multiple cancers may have a shared core molecular pathway. Specific gene modules for each type of the cancers may provide better understanding of molecular mechanisms for these cancers, and provide potential candidates of therapeutic targets to improve development of novel treatment approaches.

Our main goal of this study was to identify genes common to all 9 types of cancers from existing gene expression microarray data. Comparing gene expression profiles between cancer samples of a single type of cancer versus matching controls could effectively identify DEGs, affected signaling pathways and biological functions. However, these conventional methods have very few successes in analyzing large-scale and complicated data with multiple traits.

Therefore, in this study, systemic differences between 9 types of cancer samples versus their matching non-tumor control tissues were explored using network approach WGCNA on a large-scale gene-expression microarray datasets. Overall, the systematic genomic analysis utilizing a large collection of cancer gene-expression microarray datasets and WGCNA has revealed a shared gene module and a set of hub genes involving cell cycle and cell proliferation pathways, in which, overexpression of BIRC5, TPX2 and CDK1 have been validated using human pancreatic cancer specimens.

SEQUENCE LISTINGS

Baculoviral IAP repeat-containing protein 5 (BIRC5) isoform 1
(SEQ ID NO: 1)

```
  1 mgaptlppaw qpflkdhris tfknwpfleg cactpermae agfihcpten epdlaqcffc
 61 fkelegwepd ddpieehkkh ssgcaflsvk kqfeeltlge flkldrerak nkiaketnnk
121 kkefeetaek vrraieqlaa md
```

Baculoviral IAP repeat-containing 5 (BIRC5), transcript variant 1, mRNA
(SEQ ID NO: 2)

```
    1 cccagaaggc cgcgggggt ggaccgccta agagggcgtg cgctcccgac atgccccgcg
   61 gcgcgccatt aaccgccaga tttgaatcgc gggacccgtt ggcagaggtg gcggcggcgg
  121 catgggtgcc ccgacgttgc ccctgcctg gcagcccttt ctcaaggacc accgcatctc
  181 tacattcaag aactgccct tcttggaggg ctgcgcctgc accccggagc ggatggccga
  241 ggctggcttc atccactgcc ccactgagaa cgagccagac ttggcccagt gtttcttctg
  301 cttcaaggag ctggaaggct gggagccaga tgacgacccc atagaggaac ataaaaagca
  361 ttcgtccggt tgcgctttcc tttctgtcaa gaagcagttt gaagaattaa cccttggtga
  421 attttgaaa ctggacagag aaagagccaa gaacaaaatt gcaaggaaa ccaacaataa
  481 gaagaaagaa tttgaggaaa ctgcggagaa agtgcgccgt gccatcgagc agctggctgc
  541 catggattga ggcctctggc cggagctgcc tggtcccaga gtggctgcac cacttccagg
  601 gtttattccc tggtgccacc agccttcctg tgggccctt agcaatgtct taggaaagga
  661 gatcaacatt tcaaattag atgtttcaac tgtgctcttg ttttgtcttg aaagtggcac
  721 cagaggtgct tctgcctgtg cagcgggtgc tgctggtaac agtggctgct tctctctc
  781 tctctctttt tgggggctc attttttgctg ttttgattcc cgggcttacc aggtgagaag
  841 tgagggagga agaaggcagt gtcccttttg ctagagctga cagctttgtt cgcgtgggca
  901 gagccttcca cagtgaatgt gtctggacct catgttgttg aggctgtcac agtcctgagt
  961 gtggacttgg caggtgcctg ttgaatctga gctgcaggtt ccttatctgt cacacctgtg
 1021 cctcctcaga ggacagtttt tttgttgttg tgttttttttg tttttttttt tttggtagat
 1081 gcatgacttg tgtgtgatga gagaatggag acagagtccc tggctcctct actgtttaac
 1141 aacatggctt tcttatttg tttgaattgt taattcacag aatagcacaa actacaatta
 1201 aaactaagca caaagccatt ctaagtcatt gggggaaacgg ggtgaacttc aggtggatga
 1261 ggagacagaa tagagtgata ggaagcgtct ggcagatact ccttttgcca ctgctgtgtg
 1321 attagacagg cccagtgagc cgcggggcac atgctggccg ctcctccctc agaaaaaggc
 1381 agtggcctaa atcctttta aatgacttgg ctcgatgctg tgggggactg gctgggctgc
 1441 tgcaggccgt gtgtctgtca gcccaacctt cacatctgtc acgttctcca cacggggag
 1501 agacgcagtc cgcccaggtc cccgctttct ttggaggcag cagctcccgc agggctgaag
 1561 tctggcgtaa gatgatggat ttgattcgcc ctcctccctg tcatagagct gcagggtgga
 1621 ttgttacagc ttcgctggaa acctctggag gtcatctcgg ctgttcctga gaaataaaaa
 1681 gcctgtcatt tcaaacactg ctgtggaccc tactgggttt ttaaaatatt gtcagttttt
 1741 catcgtcgtc cctagcctgc aacagccat ctgcccagac agccgcagtg aggatgagcg
 1801 tcctggcaga gacgcagttg tctctgggcg cttgccagag ccacgaaccc cagacctgtt
 1861 tgtatcatcc gggctccttc cgggcagaaa caactgaaaa tgcacttcag cccacttat
 1921 ttctgccaca tctgagtcgg cctgagatag acttttccct ctaaactggg agaatatcac
 1981 agtggttttt gttagcagaa aatgcactcc agcctctgta ctcatctaag ctgcttattt
 2041 ttgatatttg tgtcagtctg taaatggata cttcacttta ataactgttg cttagtaatt
```

```
SEQUENCE LISTINGS 2101  ggctttgtag agaagctgga aaaaaatggt tttgtcttca actcctttgc atgccaggcg 2161  gtgatgtgga tctcggcttc tgtgagcctg tgctgtgggc agggctgagc tggagccgcc 2221  cctctcagcc cgcctgccac ggcctttcct taaaggccat ccttaaaacc agaccctcat 2281  ggctaccagc acctgaaagc ttcctcgaca tctgttaata aagccgtagg cccttgtcta 2341  agtgcaaccg cctagacttt ctttcagata catgtccaca tgtccatttt tcaggttctc 2401  taagttggag tggagtctgg gaagggttgt gaatgaggct tctgggctat gggtgaggtt 2461  ccaatggcag gttagagccc ctcgggccaa ctgccatcct ggaaagtaga gacagcagtg 2521  cccgctgccc agaagagacc agcaagccaa actggagccc ccattgcagg ctgtcgccat 2581  gtggaaagag taactcacaa ttgccaataa agtctcatgt ggttttatct aaaaaaaaaa 2641  aaaaaaaaaa aaaaa
```

Tables 5A-5C

TABLE 5A

Drugs observed to inhibit expression from the BIRC5 promoter.

| Name of Drugs | Category of Drugs |
|---|---|
| Paclitaxel | Chemotherapy |
| Mitoxantrone dihydrochloride | |
| Daunorubicin hydrochloride | |
| Camptothecine (S, +) | |
| Cantharidin | |
| Thapsigargin | Cardiovascular |
| Lanatoside C | |
| Ouabain | |
| Digitoxigenin | |
| Fluvastatin sodium salt | |
| Lovastatin | |
| Niguldipine | |
| A-23187 | Antibiotics |
| Antimycin A | |
| Bergenin Monohydrate | Metabolism |

TABLE 5B

Drugs observed to inhibit expression from the SHIP promoter.

| Name of Drugs | Category of Drugs |
|---|---|
| Doxorubicin hydrochloride | Chemotherapy |
| Mitoxantrone dihydrochloride | |
| Daunorubicin hydrochloride | |
| Camptothecine (S, +) | |
| Proscillaridin A | Cardiovascular |
| Ouabain | |
| Lanatoside C | |
| Digoxin | |
| Digitoxigenin | |
| Fluvastatin sodium salt | |
| Simvastatin | |
| Ethacrynic acid | |
| A-23187 | Antibiotics |
| Thiostrepton | |
| Metformin hydrochloride | Diabetes |

TABLE 5C

Drugs observed to inhibit expression from the LAMC2 promoter.

| Drug Name | Category |
|---|---|
| Daunorubicin hydrochloride | Chemodrug |
| Mitoxantrone dihydrochloride | |
| Doxorubicin hydrochloride | |
| Paclitaxel | |
| Camptothecine (S, +) | |
| Podophyllotoxin | Antitumor derivatives include etoposide, teniposide, and etopophos |
| Proscillaridin A | Cardiovascular drugs |
| Digoxin | |
| Digitoxigenin | |
| Simvastatin | |
| Lovastatin | |
| Digoxigenin | |
| Bergenin monohydrate | |
| Fluvastatin sodium salt | |
| Lanatoside C | |
| ANTIBIOTIC A-23187 | Antibiotics |
| Cycloheximide | |

REFERENCES

Note: This application references a number of different publications as indicated throughout the specification by reference numbers enclosed in brackets, e.g., [x]. A list of these different publications ordered according to these reference numbers can be found below.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

[1] Fokas E, O'Neill E, Gordon-Weeks A, Mukherjee S, McKenna W G, Muschel R J. (2014). Pancreatic ductal adenocarcinoma: From genetics to biology to radiobiology to oncoimmunology and all the way back to the clinic. *Biochimica et biophysica acta,* 1855(1):61-82. doi: 10.1016/j.bbcan.2014.12.001. PubMed PMID: 25489989.

[2] Chang D K, Grimmond S M, Biankin A V. (2014). Pancreatic cancer genomics. *Current opinion in genetics & development*, 24:74-81. doi: 10.1016/j.gde.2013.12.001. PubMed PMID: 24480245.

[3] Gungor C, Hofmann B T, Wolters-Eisfeld G, Bockhorn M. (2014). Pancreatic cancer. *British journal of pharmacology*, 171(4):849-58. doi: 10.1111/bph.12401. PubMed PMID: 24024905; PubMed Central PMCID: PMC3925023.

[4] Preziosi G, Oben J A, Fusai G. (2014). Obesity and pancreatic cancer. *Surgical oncology*, 23(2):61-71. doi: 10.1016/j.suronc.2014.02.003. PubMed PMID: 24746917.

[5] Rustgi A K. (2014). Familial pancreatic cancer: genetic advances. *Genes & development*, 28(1):1-7. doi: 10.1101/gad.228452.113. PubMed PMID: 24395243; PubMed Central PMCID: PMC3894408.

[6] van Kampen J G, Marijnissen-van Zanten M A, Simmer F, van der Graaf W T, Ligtenberg M J, Nagtegaal I D. (2014). Epigenetic targeting in pancreatic cancer. *Cancer treatment reviews*, 40(5):656-64. doi: 10.1016/j.ctrv.2013.12.002. PubMed PMID: 24433955.

[7] Burris H, Storniolo A M. (1997). Assessing clinical benefit in the treatment of pancreas cancer: gemcitabine compared to 5-fluorouracil. *European journal of cancer*, 33 Suppl 1:S18-22. PubMed PMID: 9166095.

[8] Karlic H, Thaler R, Gerner C, Grunt T, Proestling K, Haider F, et al. (2015). Inhibition of the mevalonate pathway affects epigenetic regulation in cancer cells. *Cancer genetics*, 208(5):241-52.

[9] Liu S, Uppal H, Demaria M, Desprez P Y, Campisi J, Kapahi P. (2015). Simvastatin suppresses breast cancer cell proliferation induced by senescent cells. *Scientific reports*, 5:17895.

[10] Fendrich, V., et al. (2013). Simvastatin delay progression of pancreatic intraepithelial neoplasia and cancer formation in a genetically engineered mouse model of pancreatic cancer. *Pancreatology*, 13(5), 502-507.

[11] Kang J I, Hong J Y, Lee H J, Bae S Y, Jung C, Park H J, et al. (2015). Anti-Tumor Activity of Yuanhuacine by Regulating AMPK/mTOR Signaling Pathway and Actin Cytoskeleton Organization in Non-Small Cell Lung Cancer Cells. *PloS one*, 10(12):e0144368.

[12] Ming M, Sinnett-Smith J, Wang J, Soares H P, Young S H, Eibl G, et al. (2014). Dose-Dependent AMPK-Dependent and Independent Mechanisms of Berberine and Metformin Inhibition of mTORC1, ERK, DNA Synthesis and Proliferation in Pancreatic Cancer Cells. *PloS one*, 9(12):e114573.

[13] Saber M M, Galal M A, Ain-Shoka A A, Shouman S A. (2016). Combination of metformin and 5-aminosalicylic acid cooperates to decrease proliferation and induce apoptosis in colorectal cancer cell lines. *BMC cancer*, 16(1):126.

[14] Amador, R. R., et al. (2012). Metformin (dimethylbiguanide) induced DNA damage in mammalian cells. *Genetics and molecular biology*, 35(1), 153-158.

[15] Kisfalvi K, Moro A, Sinnett-Smith J, Eibl G, Rozengurt E. (2013). Metformin inhibits the growth of human pancreatic cancer xenografts. *Pancreas*, 42(5):781-5.

[16] Yan G, Wang Q, Hu S, Wang D, Qiao Y, Ma G, et al. (2015). Digoxin inhibits PDGF-BB-induced VSMC proliferation and migration through an increase in ILK signaling and attenuates neointima formation following carotid injury. *International journal of molecular medicine*, 36(4):1001-11.

[17] Gao, C., et al. (2015). SCF, Regulated by HIF-1α, Promotes Pancreatic Ductal Adenocarcinoma Cell Progression. *PloS one*, 10(3), e0121338.

[18] Andren-Sandberg A. (2011). Pancreatic cancer: Animal model and molecular biology. *North American journal of medical sciences*, 3(10):441-50.

[19] Real F X, Cibrian-Uhalte E, Martinelli P. (2008). Pancreatic cancer development and progression: remodeling the model. *Gastroenterology*, 135(3):724-8.

[20] Cook N, Olive K P, Frese K, Tuveson D A. (2008). K-Ras-driven pancreatic cancer mouse model for anticancer inhibitor analyses. *Methods in enzymology*, 439:73-85.

[21] Sun Q, Feng J, Wei X L, Zhang R, Dong S Z, Shen Q, et al. (2006). Generation and characterization of a transgenic mouse model for pancreatic cancer. *World journal of gastroenterology*, 12(17):2785-8.

[22] Hiroshima Y, Maawy A, Zhang Y, Murakami T, Momiyama M, Mori R, et al. (2014). Metastatic recurrence in a pancreatic cancer patient derived orthotopic xenograft (PDOX) nude mouse model is inhibited by neoadjuvant chemotherapy in combination with fluorescence-guided surgery with an anti-CA 19-9-conjugated fluorophore. *PloS one*, 9(12): e114310.

[23] Ding Y, Cravero J D, Adrian K, Grippo P. (2010). Modeling pancreatic cancer in vivo: from xenograft and carcinogen-induced systems to genetically engineered mice. *Pancreas*, 39(3):283-92.

[24] Yamamura K, Kasuya H, Sahin T T, Tan G, Hotta Y, Tsurumaru N, et al. (2014). Combination treatment of human pancreatic cancer xenograft models with the epidermal growth factor receptor tyrosine kinase inhibitor erlotinib and oncolytic herpes simplex virus HF10. *Annals of surgical oncology*, 21(2):691-8.

[25] Izawa, J., et al. (2015). Metformin and Simvastatin Use in Bladder Cancer. ClinicalTrials.gov. Website: http://clinicaltrials.gov/ct2/show/NCT02360618.

[26] Elbaz, H. A., et al. (2012). Digitoxin and a synthetic monosaccharide analog inhibit cell viability in lung cancer cells. *Toxicology and applied pharmacology*, 258(1), 51-60.

[27] Elbaz, H. A., et al. (2012). Digitoxin and its analogs as novel cancer therapeutics. *Experimental Hematology & Oncology*, 1(4).

[28] Digoxin. (2015). SAAPedia. Website: http://www.saapedia.org/en/saa/?type=detail&id=9856.

[29] Safety Data Sheet—Simvastatin. (2014). Cayman Chemical. Website: http://www.caymanchem.com/msdss/10010344 m.pdf

[30] Kozak, M. M., et al. (2016). Statin and Metformin Use Prolongs Survival in Patients With Resectable Pancreatic Cancer. *Pancreas*, 45(1), 64-70.

[31] Calderón-Montano J, et al. The Cardiac Glycosides Digitoxin, Digoxin and Ouabain Induce a Potent Inhibition of Glycolysis in Lung Cancer Cells. WebmedCentral CANCER 2013; 4(7):WMC004323.

[32] Calderon-Montano, J. M., et al. (2014). The in vivo antitumor activity of cardiac glycosides in mice xenografted with human cancer cells is probably an experimental artifact. *Oncogene*, 33(22), 2947-2948.

[33] Zhang, H., et al. (2008). Digoxin and other cardiac glycosides inhibit HIF-1α synthesis and block tumor growth. *Proceedings of the National Academy of Sciences*, 105(50), 19579-19586.

[34] Platz, E. A., et al. (2011). A novel two-stage, transdisciplinary study identifies digoxin as a possible drug for prostate cancer treatment. *Cancer discovery*, 1(1), 68-77.

[35] Gayed, B. A., et al. (2012). Digoxin Inhibits Blood Vessel Density and HIF-la Expression in Castration-Resistant C4-2 Xenograft Prostate Tumors. *Clinical and translational science*, 5(1), 39-42.

[36] Svensson, A., et al. (2005). Digoxin inhibits neuroblastoma tumor growth in mice. *Anticancer research*, 25(1A), 207-212.

[37] Zhou, G., et al. (2015). Metformin Restrains Pancreatic Duodenal Homeobox-1 (PDX-1) Function by Inhibiting ERK Signaling in Pancreatic Ductal Adenocarcinoma. *Current molecular medicine*, 16(1), 83-90.

[38] Kordes, S., et al. (2015). Metformin in patients with advanced pancreatic cancer: a double-blind, randomised, placebo-controlled phase 2 trial. *The Lancet Oncology*, 16(7), 839-847.

[39] Kisfalvi, K., et al. (2009). Metformin disrupts crosstalk between G protein—coupled receptor and insulin receptor signaling systems and inhibits pancreatic cancer growth. *Cancer research*, 69(16), 6539-6545.

[40] Aung, K. L., & Moore, M. J. (2015). Metformin for pancreatic cancer. *The Lancet Oncology*, 16(7), 748-749.

[41] Rozengurt, E., et al. (2014). Suppression of feedback loops mediated by PI3K/mTOR induces multiple overactivation of compensatory pathways: an unintended consequence leading to drug resistance. *Molecular cancer therapeutics*, 13(11), 2477-2488.

[42] Ferrannini, E. (2014). The Target of Metformin in Type 2 Diabetes. *New England Journal of Medicine*, 371(16), 1547-1548.

[43] Pietras, R., et al. WO 2013/188452.

[44] Zhou, G., et al. (2015). Metformin Restrains Pancreatic Duodenal Homeobox-1 (PDX-1) Function by Inhibiting ERK Signaling in Pancreatic Ductal Adenocarcinoma. *Current molecular medicine*, 16(1), 83-90.

[45] Hirsch, H. A., et al. (2009). Metformin selectively targets cancer stem cells, and acts together with chemotherapy to block tumor growth and prolong remission. *Cancer research*, 69(19), 7507-7511.

[46] Iliopoulos, D., et al. (2011). Metformin decreases the dose of chemotherapy for prolonging tumor remission in mouse xenografts involving multiple cancer cell types. *Cancer research*, 71(9), 3196-3201.

[47] Hwang, K. E., et al. (2011). Apoptotic induction by simvastatin in human lung cancer A549 cells via Akt signaling dependent down-regulation of survivin. *Investigational new drugs*, 29(5), 945-952.

[48] Corcos et al., U.S. Publication No. 2014/0200269.

[49] Cui, X., et al. (2012). Statin use and risk of pancreatic cancer: a meta-analysis. *Cancer Causes & Control*, 23(7), 1099-1111.

[50] Wong, W. W. L., Dimitroulakos, J., Minden, M. D., & Penn, L. Z. (2002). HMG-CoA reductase inhibitors and the malignant cell: the statin family of drugs as triggers of tumor-specific apoptosis. *Leukemia*, 16(4), 508-519.

[51] Hughes, D. (2013). Statins and Cancer: Myriad Trials Exploring Prevention, Mortality Reduction. Website: http://www.cancertherapyadvisor.com/oncology-features/statins-and-cancer-myriad-trials-exploring-prevention-mortality-reduction/article/303292/.

[52] Donnelly, L. (2015). Statins can halve patient's risks of dying from cancer. Web site: http://www.telegraph.co.uk/news/health/11647600/Statins-can-halve-patients-risk-of-dying-from-cancer.html

[53] Hindler, K., Cleeland, C. S., Rivera, E., & Collard, C. D. (2006). The role of statins in cancer therapy. *The Oncologist*, 11(3), 306-315.

[54] Lee, C. K., et al. (2016). Cumulative metformin use and its impact on survival in gastric cancer patients after gastrectomy. *Annals of surgery*, 263(1), 96-102.

[55] Liu, S., et al. (2008). PDX-1 Acts as a Potential Molecular Target for Treatment of Human Pancreatic Cancer. *Pancreas*, 37(2), 210-220.

[56] Liu, S.-H., et al. (2012) PDX-1 Is a Therapeutic Target for Pancreatic Cancer, Insulinoma and Islet Neoplasia Using a Novel RNA Interference Platform. *PLoS ONE*, 7(8): e40452. doi:10.1371/journal.pone.0040452.

[57] Siegel R, Ma J, Zou Z, Jemal A. (2014). Cancer statistics, 2014. *CA: a cancer journal for clinicians*, 64(1): 9-29.

[58] Siegel R L, Miller K D, Jemal A. (2015). Cancer statistics, 2015. *CA: a cancer journal for clinicians*, 65(1):5-29.

[59] Levin J Z, Berger M F, Adiconis X, Rogov P, Melnikov A, Fennell T, et al. (2009). Targeted next-generation sequencing of a cancer transcriptome enhances detection of sequence variants and novel fusion transcripts. *Genome biology*, 10(10):R115.

[60] Ding L, Wendl M C, Koboldt D C, Mardis E R. (2010). Analysis of next-generation genomic data in cancer: accomplishments and challenges. *Human molecular genetics*, 19(R2):R188-96.

[61] Prensner J R, Iyer M K, Balbin O A, Dhanasekaran S M, Cao Q, Brenner J C, et al. (2011). Transcriptome sequencing across a prostate cancer cohort identifies PCAT-1, an unannotated lincRNA implicated in disease progression. *Nature biotechnology*, 29(8):742-9.

[62] Fendler B, Atwal G. (2012). Systematic deciphering of cancer genome networks. *The Yale journal of biology and medicine*, 85(3):339-45.

[63] Fuller T F, Ghazalpour A, Aten J E, Drake T A, Lusis A J, Horvath S. (2007). Weighted gene coexpression network analysis strategies applied to mouse weight. *Mammalian genome: official journal of the International Mammalian Genome Society*, 18(6-7):463-72.

[64] Langfelder P, Horvath S. (2008). WGCNA: an R package for weighted correlation network analysis. *BMC bioinformatics*, 9:559.

[65] Presson A P, Sobel E M, Papp J C, Suarez C J, Whistler T, Rajeevan M S, et al. (2008). Integrated weighted gene co-expression network analysis with an application to chronic fatigue syndrome. *BMC systems biology*, 2:95.

[66] Zhang B, Horvath S. (2005). A general framework for weighted gene co-expression network analysis. *Statistical applications in genetics and molecular biology*, 4:Article17.

[67] Clarke C, Madden S F, Doolan P, Aherne S T, Joyce H, O'Driscoll L, et al. (2013). Correlating transcriptional networks to breast cancer survival: a large-scale coexpression analysis. *Carcinogenesis*, 34(10):2300-8.

[68] Griesinger A M, Birks D K, Donson A M, Amani V, Hoffman L M, Waziri A, et al. (2013). Characterization of distinct immunophenotypes across pediatric brain tumor types. *Journal of immunology*, 191(9):4880-8.

[69] Sabates-Bellver J, Van der Flier L G, de Palo M, Cattaneo E, Maake C, Rehrauer H, et al. (2007). Transcriptome profile of human colorectal adenomas. *Molecular cancer research*, 5(12):1263-75.

[70] D'Errico M, de Rinaldis E, Blasi M F, Viti V, Falchetti M, Calcagnile A, et al. (2009). Genome-wide expression profile of sporadic gastric cancers with microsatellite instability. *European journal of cancer*, 45(3):461-9.

[71] Lei Z, Tan I B, Das K, Deng N, Zouridis H, Pattison S, et al. (2013). Identification of molecular subtypes of gastric cancer with different responses to PI3-kinase inhibitors and 5-fluorouracil. *Gastroenterology,* 145(3): 554-65.

[72] Lu T P, Tsai M R, Lee J M, Hsu C P, Chen P C, Lin C W, et al. (2010). Identification of a novel biomarker, SEMA5A, for non-small cell lung carcinoma in non-smoking women. *Cancer epidemiology, biomarkers & prevention: a publication of the American Association for Cancer Research, cosponsored by the American Society of Preventive Oncology,* 19(10):2590-7.

[73] Badea L, Herlea V, Dima S O, Dumitrascu T, Popescu I. (2008). Combined gene expression analysis of whole-tissue and microdissected pancreatic ductal adenocarcinoma identifies genes specifically overexpressed in tumor epithelia. *Hepato-gastroenterology,* 55(88):2016-27.

[74] Pei H, Li L, Fridley B L, Jenkins G D, Kalari K R, Lingle W, et al. (2009). FKBP51 affects cancer cell response to chemotherapy by negatively regulating Akt. *Cancer cell,* 16(3):259-66.

[75] von Roemeling C A, Radisky D C, Marlow L A, Cooper S J, Grebe S K, Anastasiadis P Z, et al. (2014). Neuronal pentraxin 2 supports clear cell renal cell carcinoma by activating the AMPA-selective glutamate receptor-4. *Cancer research,* 74(17):4796-810.

[76] Varambally S, Yu J, Laxman B, Rhodes D R, Mehra R, Tomlins S A, et al. (2005). Integrative genomic and proteomic analysis of prostate cancer reveals signatures of metastatic progression. *Cancer cell,* 8(5):393-406.

[77] Arredouani M S, Lu B, Bhasin M, Eljanne M, Yue W, Mosquera J M, et al. (2009). Identification of the transcription factor single-minded homologue 2 as a potential biomarker and immunotherapy target in prostate cancer. *Clinical cancer research: an official journal of the American Association for Cancer Research,* 15(18):5794-802.

[78] Birks D K, Donson A M, Patel P R, Sufit A, Algar E M, Dunham C, et al. (2013). Pediatric rhabdoid tumors of kidney and brain show many differences in gene expression but share dysregulation of cell cycle and epigenetic effector genes. *Pediatric blood & cancer,* 60(7): 1095-102.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A composition of matter comprising a combination of:
   metformin or a metformin analog;
   at least one statin selected from the group consisting of: simvastatin, atorvastatin, rosuvastatin, fluvastatin, lovastatin, pitavastatin, pravastatin, and prosuvastatin; and
   a cardiac glycoside; wherein the composition comprises amounts of metformin, simvastatin, and digoxin sufficient to inhibit in vivo growth of a human pancreatic ductal adenocarcinoma cell when administered to a patient diagnosed with pancreatic ductal adenocarcinoma.

2. The composition of claim 1, further comprising a pharmaceutically acceptable carrier selected to be compatible with metformin, simvastatin, and digoxin.

3. The composition of claim 2, wherein the composition is formed as a time release formulation.

4. The composition of claim 3, wherein the composition is disposed in a capsule or tablet.

5. The composition of claim 1, wherein the composition comprises:
   5-80 milligrams of simvastatin;
   500-2550 milligrams of metformin; and
   0.125-0.250 milligrams of digoxin.

6. A composition of matter comprising a combination of:
   metformin, simvastatin and digoxin;
   wherein the composition comprises amounts of metformin, simvastatin, and digoxin sufficient to inhibit in vivo growth of a human pancreatic ductal adenocarcinoma cell when administered to a patient diagnosed with pancreatic ductal adenocarcinoma.

7. The composition of claim 6, wherein the composition comprises:
   between 5-80 milligrams of simvastatin;
   between 500-2550 milligrams of metformin; and
   between 62.5 micrograms of digoxin and 0.250 milligrams of digoxin.

8. The composition of claim 7, further comprising a pharmaceutically acceptable carrier selected to be compatible with metformin, simvastatin, and digoxin.

9. The composition of claim 7, wherein the composition is formed as a time release formulation.

10. The composition of claim 7, wherein the composition is disposed in a capsule or tablet.

* * * * *